US007928222B2

(12) United States Patent
Kobuke et al.

(10) Patent No.: US 7,928,222 B2
(45) Date of Patent: Apr. 19, 2011

(54) PORPHYRIN COMPOUND, PROCESS FOR PRODUCING PORPHYRIN COMPOUND, THREE-DIMENSIONAL OPTICAL RECORDING MATERIAL, AND THREE-DIMENSIONAL OPTICAL RECORDING MEDIUM

(75) Inventors: Yoshiaki Kobuke, Ikoma (JP); Kazuya Ogawa, Ikoma (JP)

(73) Assignee: National University Corporation Nara Institute of Science and Technology, Ikoma-shi (JP)

( * ) Notice: Subject to any disclaimer, the term of this patent is extended or adjusted under 35 U.S.C. 154(b) by 1133 days.

(21) Appl. No.: 11/649,380

(22) Filed: Jan. 4, 2007

(65) Prior Publication Data

US 2007/0224529 A1 Sep. 27, 2007

(30) Foreign Application Priority Data

Mar. 27, 2006 (JP) ................................. 2006-084749

(51) Int. Cl.
*C07D 487/22* (2006.01)
(52) U.S. Cl. ...................................................... 540/145
(58) Field of Classification Search .................. 540/145
See application file for complete search history.

(56) References Cited

U.S. PATENT DOCUMENTS 7,022,840 B2 4/2006 Kobuke et al.

OTHER PUBLICATIONS

D. Parthenopoulos & P. Rentzepis; *Three-Dimensional Optical Storage Memory*, (Aug. 25, 1989) vol. 245, pp. 843-845.
A. Dvornikov, Y. Liang, C. Cruse & P. Rentzepis; Spectroscopy and Kinetics of a Molecular Memory with Nondestructive Readout for Use in 2D and 3D Storage Systems; *Phys. Chem. B.*, (2004) vol. 108, No. 25; pp. 8652-8658.
K. Ogawa, J. Dy & Y. Kobuke; Substituent effect on two-photon absorption properties of conjugated porphyrins; *Journal of Porphyrins and Phthalocyanines*, (2005) 9: pp. 735-744.
J. Laha, S. Dhanalekshmi, M. Taniguchi, A. Ambroise & J. Lindsey; A Scalable Synthesis of Meso-Substituted Dipyrromethanes; *Organic Process & Research Development*, (2003) vol. 7, No. 6; pp. 799-812.
J. Leavitt; Dyes, Fluorescent Whitening Agents, and Photosensitizers; *Chemical Abstracts*, (1971) vol. 74; pp. 50-51.
J. Rabai; *3-Mercaptopropionic Acid: A New Tool in the Synthesis of Symmetrical Diaryl Sulfides from Unactivated Aryl Iodides as Substitute for Anhydrous Sodium Sulfide*; Synthesis, (Jul. 1989) pp. 523-525.
R. Bailey, P. Card, & H. Shechter; Chemistry of 8-Substituted 1-Naphythylmethylenes and 2-Substituted Benzylidenes. A Simple Entry to 1H-Cyclobuta [de]naphthalenes, *Journal American Chemical Society*, (1983) vol. 105, pp. 6096-6103.
K. Ogawa, A. Ohashi, Y. Kobuke, K. Kamada, & K. Ohta; Two-Photon Absorption Properties of Self-Assemblies of Butadiyne-Linked Bis(Imidazolylporphyrin); *J. Phys. Chem.*, (2005), vol. 109, pp. 22003-22012.
*Chemical Abstracts* (1969); vol. 70, p. 328.

*Primary Examiner* — James O Wilson
*Assistant Examiner* — Brian McDowell
(74) *Attorney, Agent, or Firm* — Posz Law Group, PLC

(57) ABSTRACT

Compounds described herein are suitable for use in three-dimensional optical recording materials, etc. The compounds each have a structure that allows pi-electron conjugation to be achieved by linking a porphyrin ring and a perinaphthothio-indigo ring to each other with a straight-chain atomic group. The compounds are suitable for use in three-dimensional optical recording materials, etc. since they have a high two-photon absorption efficiency and undergo photochromism effectively through optical absorption. The compounds include those represented by the following formula (1):

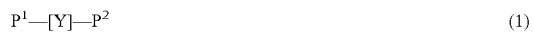

$$P^1-[Y]-P^2 \qquad (1)$$

where $P^1$ corresponds to a porphyrin ring; $P^2$ corresponds to a perinaphthothioindigo ring a hydrogen atom, or a halogen atom; and Y is a group that links $P^1$ and $P^2$.

8 Claims, 12 Drawing Sheets

PORPHYRIN COMPOUND, PROCESS FOR PRODUCING PORPHYRIN COMPOUND, THREE-DIMENSIONAL OPTICAL RECORDING MATERIAL, AND THREE-DIMENSIONAL OPTICAL RECORDING MEDIUM

CROSS REFERENCE TO RELATED APPLICATION

This patent application claims priority based on Japanese Patent Application No. JP2006-084749 (filed on Mar. 27, 2006), the contents of which are incorporated herein by reference in its entirety.

BACKGROUND OF THE INVENTION

1. Field of the Invention

The present invention relates to porphyrin compounds, processes for producing porphyrin compounds, and three-dimensional optical recording materials and three-dimensional optical recording media containing porphyrin compounds.

2. Description of the Related Art

Information recording media are used for various applications including business, home, and personal uses. Accordingly, information recording media are very important in modern industries and societies. Among the information recording media, currently, optical recording media on which information is recorded optically are used particularly widely. This is because the optical recording media have ease of information recording, a large recording capacity, etc. Examples of mainstream optical recording media include CDs, MOs, DVDs, etc. These optical recording media contain suitable optical recording materials and thereby allow information to be recorded thereon. In order to further increase the recording capacities of the optical recording media, research and development of better optical recording materials have been proceeding.

An example of the aforementioned optical recording materials is a material that allows information to be recorded by a recording method that is referred to as a "heat mode". The heat mode is a method in which the change in refractive index is used. The change in refractive index is caused in the optical recording material by a thermal effect generated upon light irradiation. However, the heat mode has a limitation in recording capacity due to the diffraction limit of light. Hence, a study for recording or erasing information by a recording method that is referred to as a "photon mode" is being made. This photon mode allows a larger volume of information to be recorded as compared to the heat mode. For the photon mode, a photochromic material containing a photochromic compound (photochromic molecule) is used as an optical recording material. The photon mode allows information to be recorded by utilizing the isomerization of the photochromic compound that is caused by photon absorption.

The photochromic compound (photochromic molecule) is a compound (molecule) that exhibits photochromism. The photochromic material is an optical recording material that is formed of the photochromic compound and allows information to be recorded or erased by photochromism. The photochromism is a phenomenon in which a chemical species is isomerized reversibly between two states that are different in absorption spectrum, by light irradiation. Examples of the method of using the photochromic material include a method in which light irradiation is carried out repeatedly with the irradiation wavelength being varied. For example, this method makes it possible to repeat information recording and erasing by repeating bleaching and coloring that result from isomerization (photochromism) of the photochromic compound. Various compounds are being studied to be used practically as such a photochromic material. Among the photochromic compounds, recently, particularly organic compounds are being researched and developed actively.

Examples of currently known photochromic compounds include azobenzenes, diarylethenes, spiropyrans, fulgides, indigos, etc. However, with these conventional photochromic compounds, two-dimensional recording can be achieved but three-dimensional recording is difficult. This is because the photoisomerization reaction is caused by one-photon absorption in those conventional photochromic compounds. Accordingly, optical recording media such as CDs, MOs, DVDs, etc. that are used mainly at present are two-dimensional optical recording media (two-dimensional optical memory media). In the case of the two-dimensional optical recording media, information is recorded two-dimensionally, but the thickness direction of the media is not utilized. Thus, the thickness direction of the optical recording media cannot be utilized for information recording and this poses a limitation on recording capacity.

In order to solve this problem, construction of three-dimensional optical recording media (three-dimensional optical memory media) can be considered. In the three-dimensional optical recording media, information is written in the inner part thereof while being superposed in a plurality of layers. Accordingly, with the three-dimensional optical recording media, a considerable increase in recording capacity can be expected. In order to construct the three-dimensional optical recording media, the use of a photochromic compound that is isomerized by two-photon absorption is considered to be useful.

The two-photon absorption denotes that two photons in the wavelength range where one-photon absorption does not occur are absorbed simultaneously. Two-photon absorption makes it possible to generate an excitation state corresponding to the sum of energy of two photons. Accordingly, two-photon absorption can be caused selectively only at a position with a higher optical density such as a focal point in an optical recording material. Hence, two-photon absorption allows optical absorption to be controlled, with the three-dimensional position being selected in the optical recording material. It therefore is possible to carry out three-dimensional recording in which the thickness direction of the optical recording material also is utilized. Thus, when a photochromic compound (photochromic molecule) with a high two-photon absorption efficiency is developed and is used as an optical recording material, three-dimensional optical recording media can be produced.

Photochromic materials that utilize two-photon absorption also have been proposed in the past (see, for instance, D. A. Parthenopoulos, P. M. Rentzepis, Science 245 (1989) 843, and A. S. Dvornikov, Y. Liang, C. S. Cruse, P. M. Rentzepis, J. Phys. Chem. B 108 (2004) 8652). However, these photochromic materials are far from practical use since the two-photon absorption efficiency thereof is low (i.e. the two-photon absorption cross section is small).

The present inventors have invented a compound in which a porphyrin compound is linked using an ethynylene group (JP2004-168690A). This compound has a two-photon absorption efficiency that has been improved by two orders of magnitude or more as compared to those of conventional compounds. However, although this compound has a high two-photon absorption efficiency, the compound is difficult to undergo isomerization (photochromism) by optical absorption. Accordingly, the compound described in JP2004-168690A has a problem when being used as an optical recording material.

SUMMARY

The present invention is concerned with compounds that are suitable to be used for three-dimensional optical recording materials. A compound of the invention includes a porphyrin compound, a tautomer or stereoisomer thereof, or a salt thereof.

DETAILED DESCRIPTION

Figure 1:
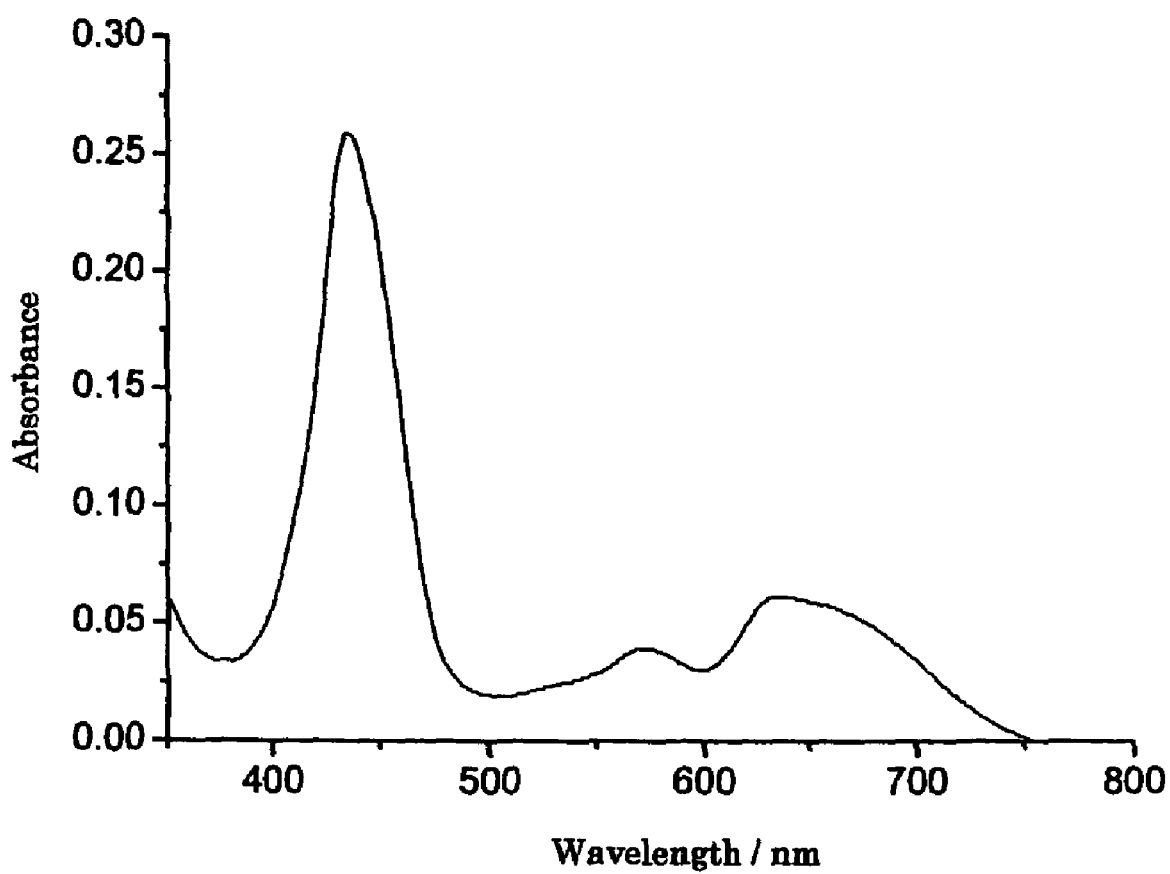
FIG. 1 is a graph showing a visible/ultraviolet absorption spectrum of a compound (3) according to an example (in a tetrahydrofuran (THF) solution).

Hereinafter, the present invention is described in detail.

The present inventors made keen studies assiduously to solve the aforementioned problems. That is, the present inventors studied to invent a compound that has a high two-photon absorption efficiency and undergoes photochromism effectively by optical absorption. The present inventors linked a porphyrin ring and a perinaphthothioindigo ring to each other with a straight-chain atomic group. As a result, the present inventors invented a compound that can have pi-electron conjugation between the porphyrin ring and the perinaphthothioindigo ring. The perinaphthothioindigo is changed from a trans form to a cis form by irradiation of light with a wavelength of about 620 nm, while it reverts from the cis form to the trans form by irradiation of light with a wavelength of about 508 nm (Scheme 1 shown below), for example. In this manner, light with a relatively long wavelength allows perinaphthothioindigo to undergo a photoisomerization reaction (photochromism). However, no study has been made in which the perinaphthothioindigo structure is used for improving the two-photon absorption efficiency.

Scheme 1

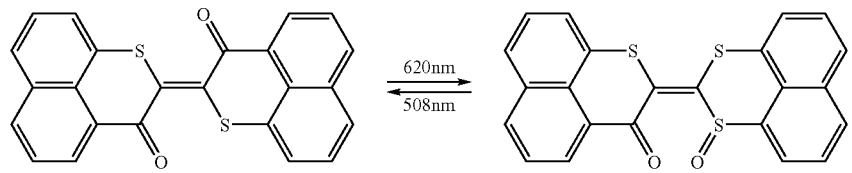

A compound of the present invention is a porphyrin compound, a tautomer or stereoisomer thereof, or a salt thereof. The porphyrin compound is represented by the following formula (1) and contains one or a plurality of porphyrin rings and one or a plurality of perinaphthothioindigo rings.

$$P^1\text{—}[Y]\text{—}P^2 \tag{1}$$

In the formula (1), $P^1$ denotes an atomic group represented by the following formula ($a^1$), ($b^1$), or ($c^1$),

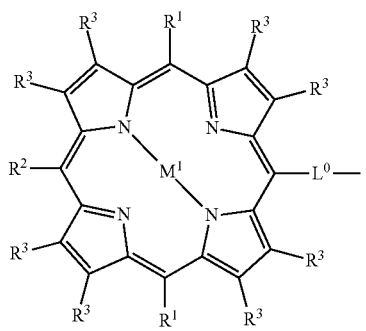
(a¹)
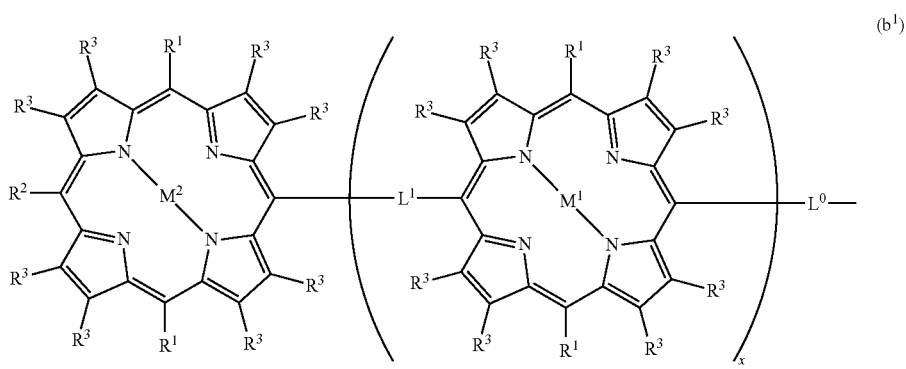
(b¹)
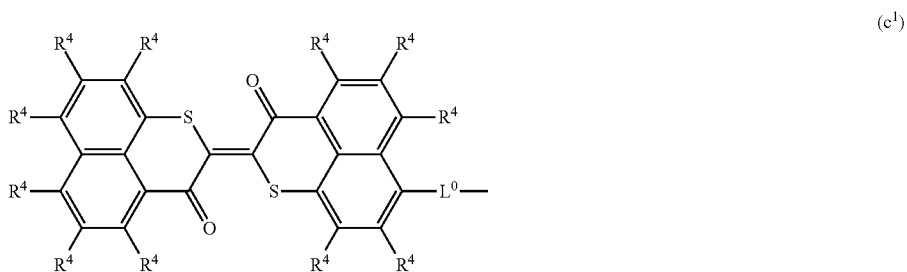
(c¹)
[Y] denotes an atomic group represented by the following formula (a²), (b²), or (c²), and
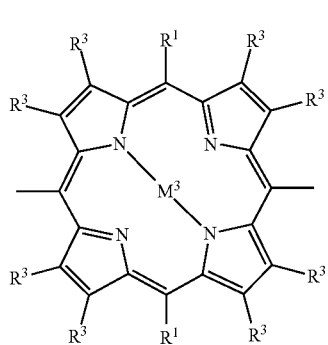
(a²)

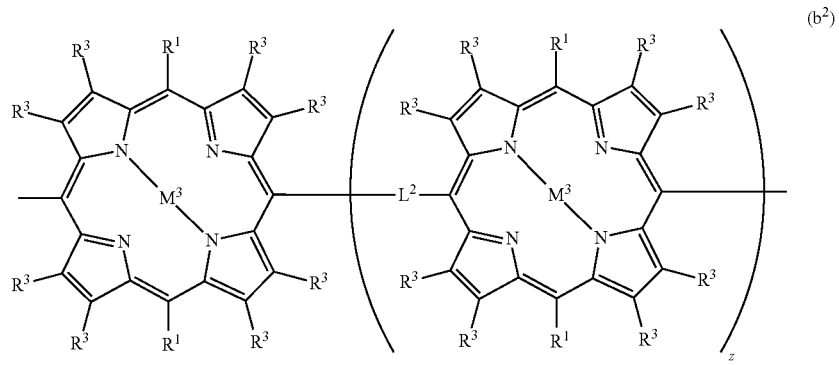
(b²)
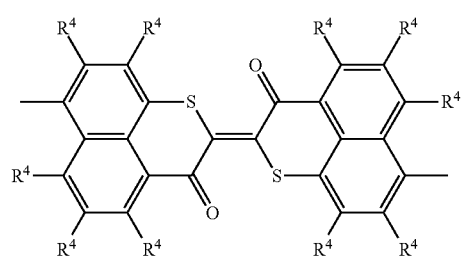
(c²)
P² denotes a hydrogen atom, a halogen, or an atomic group represented by the following formula (a³), (b³), or (c³).
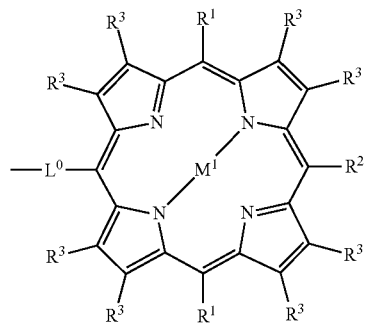
(a³)
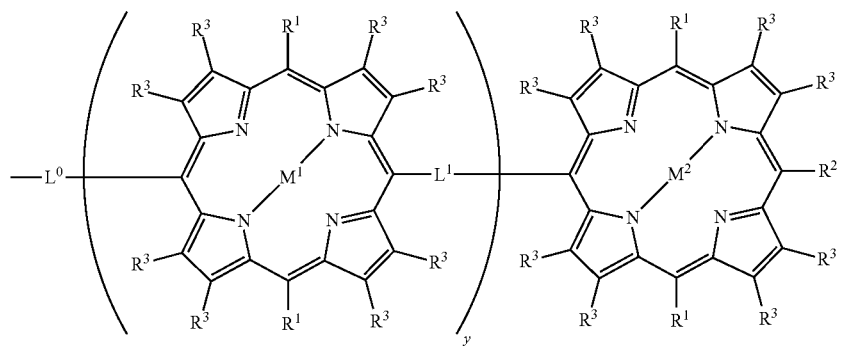
(b³)

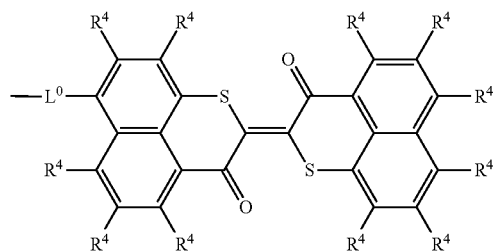

(c³)

In the formulae (a¹), (b¹), (a²), (b²), (a³), and (b³), $R^1$s each indicate a hydrogen atom, a substituted or non-substituted alkyl group, or a substituted or non-substituted aryl group, the substituted or non-substituted alkyl group can be of a straight-chain or a branched-chain or can be cyclic (a substituted or non-substituted cycloalkyl group), the substituted alkyl group can contain one or a plurality of substituents, in the case of the plurality of substituents, they can be identical to or different from each other, and the substituted or non-substituted aryl group can be of a monocycle or a condensed ring and can contain a hetero atom or no hetero atom, the substituted aryl group can contain one or a plurality of substituents, in the case of the plurality of substituents, they can be identical to or different from each other, and the respective $R^1$s can be identical to or different from each other, and $R^3$s each indicate a hydrogen atom, a substituted or non-substituted alkyl group, or a substituted or non-substituted aryl group, the substituted or non-substituted alkyl group can be of a straight-chain or a branched-chain or can be cyclic (a substituted or non-substituted cycloalkyl group), the substituted alkyl group can contain one or a plurality of substituents, in the case of the plurality of substituents, they can be identical to or different from each other, the substituted or non-substituted aryl group can be of a monocycle or a condensed ring and can contain a hetero atom or no hetero atom, the substituted aryl group can contain one or a plurality of substituents, in the case of the plurality of substituents, they can be identical to or different from each other, and the respective $R^3$s can be identical to or different from each other.

In the formulae (a¹), (b¹), (c¹), (a³), (b³), and (c³), $L^0$ denotes a straight-chain atomic group that can conjugate with each of the rings bonded to both ends of $L^0$, and when the formula (1) contains a plurality of $L^0$s, the respective $L^0$s can be identical to or different from each other.

In the formulae (a¹), (b¹), (a³), and (b³), $R^2$s each indicate a hydrogen atom, a substituted or non-substituted alkyl group, a substituted or non-substituted aryl group, a five- or six-membered nitrogen-containing coordinating heteroaromatic ring, or a halogen, the substituted or non-substituted alkyl group can be of a straight-chain or a branched-chain or can be cyclic (a substituted or non-substituted cycloalkyl group), the substituted alkyl group can contain one or a plurality of substituents, in the case of the plurality of substituents, they can be identical to or different from each other, the substituted or non-substituted aryl group can be of a monocycle or a condensed ring and can contain a hetero atom or no hetero atom, the substituted aryl group can contain one or a plurality of substituents, in the case of the plurality of substituents, they can be identical to or different from each other, and when the formula (1) contains a plurality of $R^2$s, the respective $R^2$s can be identical to or different from each other, and $M^1$ indicates metal, metal halide, metal oxide, metal hydroxide, Si, Ge, or P, or two hydrogen atoms, and when the formula (1) contains a plurality of $M^1$s, the respective $M^1$s can be identical to or different from each other.

In the formula (b¹), x denotes a positive integer.

In the formula (b³), y denotes a positive integer.

In the formulae (b¹) and (b³), $M^2$ indicates metal, metal halide, metal oxide, metal hydroxide, Si, Ge, or P, or two hydrogen atoms, $M^1$ and $M^2$ can be identical to or different from each other, and when the formula (1) contains a plurality of $M^2$s, the respective $M^2$s can be identical to or different from each other, and $L^1$ denotes a straight-chain atomic group that can conjugate with each of the porphyrin rings bonded to both ends of $L^1$, $L^0$ and $L^1$ can be identical to or different from each other, and when the formula (1) contains a plurality of $L^1$s, the respective $L^1$s can be identical to or different from each other.

In the formulae (a²) and (b²), $M^3$ indicates metal, metal halide, metal oxide, metal hydroxide, Si, Ge, or P, or two hydrogen atoms, $M^3$ can be identical to or different from the aforementioned $M^1$ and $M^2$, and when the formula (1) contains a plurality of $M^3$s, the respective $M^3$s can be identical to or different from each other.

In the formula (b²), z denotes a positive integer, and $L^2$ denotes a straight-chain atomic group that can conjugate with each of the porphyrin rings bonded to both ends of $L^2$, $L^2$ can be identical to or different from the $L^0$ and $L^1$, and when a plurality of $L^2$s are present, the respective $L^2$s can be identical to or different from each other.

In the formulae (c¹), (c²), and (C³), $R^4$s each denote a hydrogen atom or a halogen, and the respective $R^4$s can be identical to or different from each other.

A three-dimensional optical recording material of the present invention is a three-dimensional optical recording material containing a compound of the present invention.

Furthermore, a three-dimensional optical recording medium of the present invention is a three-dimensional optical recording medium having a recording layer in which information can be recorded. The recording layer contains the three-dimensional optical recording material of the present invention.

The compound of the present invention has a high two-photon absorption efficiency and undergoes photochromism effectively by optical absorption. Accordingly, the compound of the present invention is suitable to be used for a three-dimensional optical recording material, etc. The three-dimensional optical recording material of the present invention contains a compound of the present invention and thereby allows three-dimensional recording to be carried out. That is, the three-dimensional recording can be carried out by a method including isomerizing the compound of the present invention through two-photon absorption by irradiating the compound with light. In addition, the three-dimensional optical recording medium of the present invention allows large-volume recording to be carried out since the three-dimensional optical recording material of the present invention is contained therein.

Furthermore, the use of a compound according to the present invention is not limited to three-dimensional optical recording materials and three-dimensional optical recording media. For instance, optical recording can be carried out by a method including isomerizing a compound of the present invention through one-photon absorption by irradiating the compound with light. This also allows a compound of the present invention to be used for conventional two-dimensional optical recording materials or two-dimensional optical recording media. Specifically, an optical recording material of the present invention is an optical recording material containing a compound of the present invention. Furthermore, an optical recording medium of the present invention is an optical recording medium having a recording layer in which information can be recorded. The recording layer contains an optical recording material of the present invention. Moreover, the compound of the present invention can be used for optical recording materials and any applications other than the optical recording materials. For instance, a compound of the present invention can be used, as pigments, for applications other than the optical recording materials.

In the present invention, the term "halogen" denotes an arbitrary halogen element. Examples of the halogen include fluorine, chlorine, bromine, and iodine. In the present invention, the "alkyl group" is not particularly limited. Examples of the alkyl group include a methyl group, an ethyl group, an n-propyl group, an isopropyl group, an n-butyl group, an isobutyl group, a sec-butyl group, a tert-butyl group, etc. The same applies to groups each containing an alkyl group in its structure or groups derived from alkyl groups (an alkoxy group, a carboxyalkyl group, an alkoxycarbonylalkyl group, an alkoxyalkyl group, an alkenoxyalkyl group, etc.).

When, for instance, a substituent etc. is a group having a chain structure (for example, an alkyl group, an alkoxy group, a carboxyalkyl group, an alkoxycarbonylalkyl group, an alkoxyalkyl group, an alkenoxyalkyl group, etc.) it can be of a straight-chain or a branched-chain unless otherwise limited. The same applies to the case when a chain structure is contained in a part of a substituent etc., for example, where the substituent in a substituted alkyl group or substituted aryl group contains a chain structure. When, for example, the substituent etc. contains an isomer, it can be any isomer unless otherwise limited. For instance, when a term referred to simply as a "propyl group" is used, it can be either an n-propyl group or an isopropyl group. When a term referred to simply as a "butyl group" is used, it can be any one of an n-butyl group, an isobutyl group, a sec-butyl group, and a tert-butyl group. When a term referred to simply as a "naphthyl group" is used, it can be either a 1-naphthyl group or a 2-naphthyl group. Furthermore, in the present invention, when the scope of the present invention is limited by numerical values, it should be understood that the present invention embraces not only the cases obtained in the strict range of the numerical values but also the cases obtained in the approximate range of the numerical values. For instance, in the case of "20° C. to 30° C.", the present invention embraces not only the case of strictly 20° C. to 30° C. but also the case of approximately 20° C. to 30° C. Moreover, for instance, when the number of carbon atoms is "1 to 24", the present invention embraces both the case of strictly 1 to 24 and the case of approximately 1 to 24.

[Compounds of the Present Invention]

As described above, in a compound of the present invention, when the formula (1) contains a plurality of $L^0$s, the respective $L^0$s can be identical to or different from each other. In the formula (1), it is preferable that $L^0$ be represented by the following formula ($L^{100}$).

In the formula ($L^{100}$), n denotes an integer of 1 to 3. From the viewpoints of easy production, yield, etc. of the compound of the present invention, it is more preferable that the formula ($L^{100}$) be an ethynylene group (—C≡C—) (n=1). $L^0$ can be a polyacetylene group with the polymerization degree n exceeding 3 or another group. Preferably, $L^0$ is a group that provides the compound of the present invention with a photochromic property that allows it to be used practically as a three-dimensional optical recording material.

As described above, in the formula (1), when the formula (1) contains a plurality of $L^1$s, $L^1$s in the formulae ($b^1$) and ($b^3$) can be identical to or different from each other. In the formulae ($b^1$) and ($b^3$), it is preferable that $L^1$ be represented by the following formula ($L^{200}$).

In the formula ($L^{200}$), m denotes an integer of 1 to 3. It is more preferable that the formula ($L^{200}$) be an ethynylene group (—C≡C—) (m=1). $L^1$ can be a polyacetylene group with the polymerization degree m exceeding 3 or another group. Preferably, $L^1$ is a group that provides the compound of the present invention with a photochromic property that allows it to be used practically as a three-dimensional optical recording material.

As described above, in the formula (1), when the formula (1) contains a plurality of $L^2$s, $L^2$s in the formula ($b^2$) can be identical to or different from each other. In the formula ($b^2$), it is preferable that $L^2$ be represented by the following formula ($L^{300}$).

In the formula ($L^{300}$), l denotes an integer of 1 to 3. It is more preferable that the formula ($L^{300}$) be an ethynylene group (—C≡C—) (l=1). $L^2$ can be a polyacetylene group with the polymerization degree l exceeding 3 or another group. Preferably, $L^2$ is a group that provides the compound of the present invention with a photochromic property that allows it to be used practically as a three-dimensional optical recording material.

In the compounds of the present invention, the number of perinaphthothioindigo rings can be one or plural. The number of perinaphthothioindigo rings is preferably one from the viewpoint of simplification of the photochromism. Among the compounds of the present invention in which the number of perinaphthothioindigo rings is one, the following compounds (i) to (v) are more preferable, for example.

(i) Compound in which in the formula (1), [Y] is represented by the formula ($c^2$), $P^1$ is represented by the formula ($a^1$), and $P^2$ is a hydrogen atom.

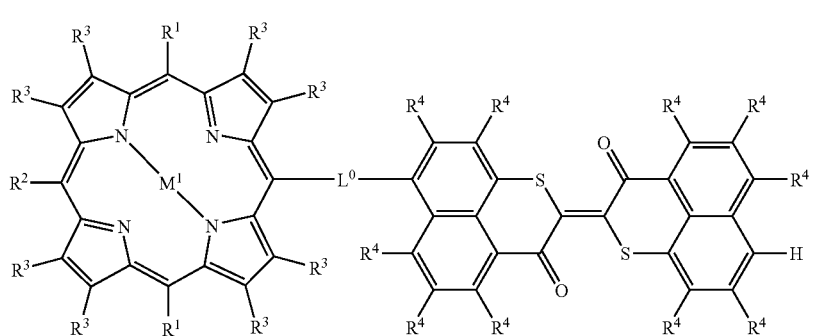

(ii) Compound in which in the formula (1), [Y] is represented by the formula ($c^2$), $P^1$ is represented by the formula ($b^1$), the formula ($b^1$) has a polymerization degree x of 1, and $P^2$ is a hydrogen atom.

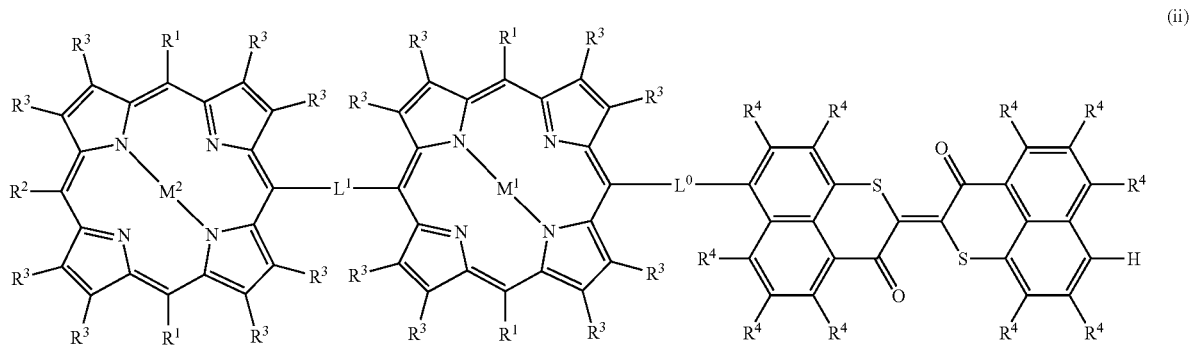

(iii) Compound in which in the formula (1), [Y] is represented by the formula ($c^2$), $P^1$ is represented by the formula ($a^1$), and $p^2$ is represented by the formula ($a^3$).

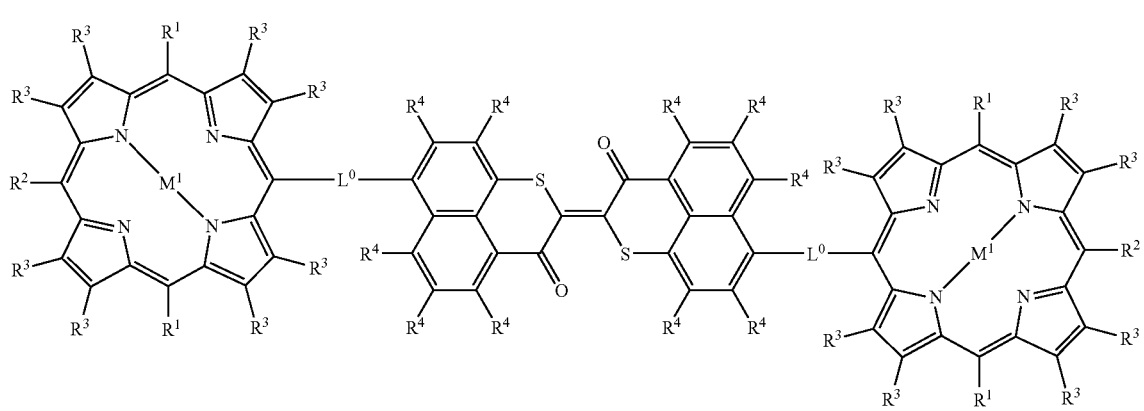

(iv) Compound in which in the formula (1), [Y] is represented by the formula ($c^2$), $P^1$ is represented by the formula ($b^1$), the formula ($b^1$) has a polymerization degree x of 1, $P^2$ is represented by the formula ($b^3$), and the formula ($b^3$) has a polymerization degree y of 1.

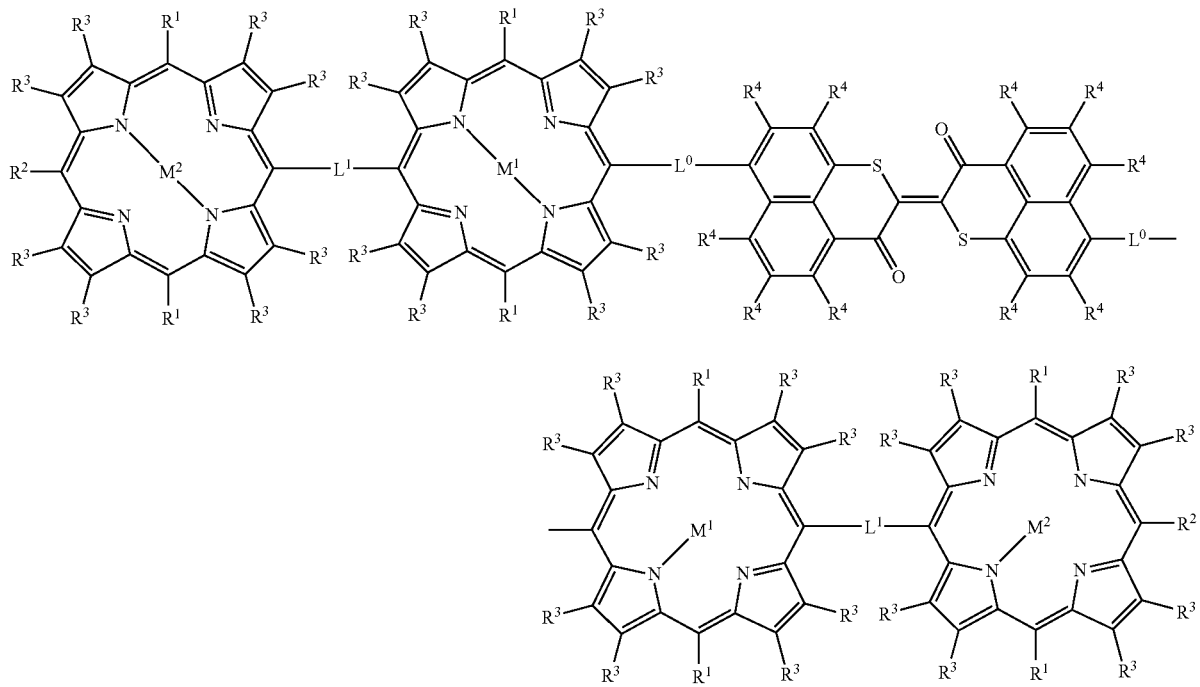

(iv)

(v) Compound in which in the formula (1), [Y] is represented by the formula ($c^2$), $P^1$ is represented by the formula ($a^1$), $P^2$ is represented by the formula ($b^3$), and the formula ($b^3$) has a polymerization degree y of 1.

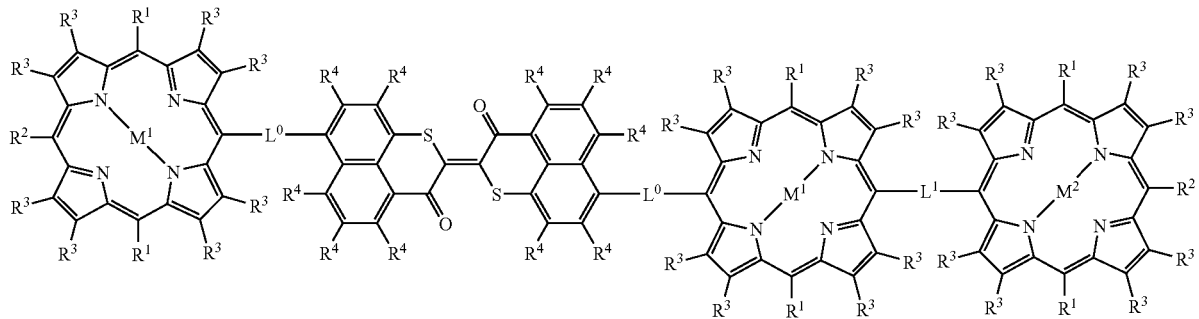

(v)

More preferably, a compound of the present invention having the structure (i), (ii), (iii), (iv), or (v) is, for example, a porphyrin compound, a tautomer or stereoisomer thereof, or a salt thereof, with the porphyrin compound being represented by one of the following formulae (xi) to (xv) in which in the formulae ($a^1$), ($b^1$), ($a^3$), and ($b^3$), $R^3$s are all hydrogen atoms and $L^0$ denotes an ethynylene group, in the formulae ($b^1$) and ($b^3$), $L^1$ is represented by the formula ($L^{200}$), and when the formula (1) contains a plurality of $L^1$s, the respective $L^1$s can be identical to or different from each other, and in the formula (c²), R⁴s are all hydrogen atoms.
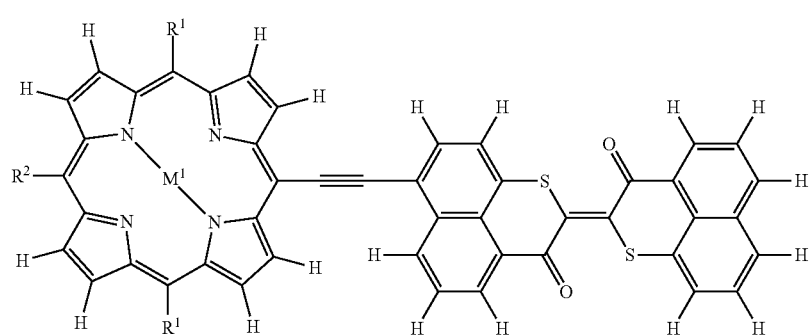
(xi)
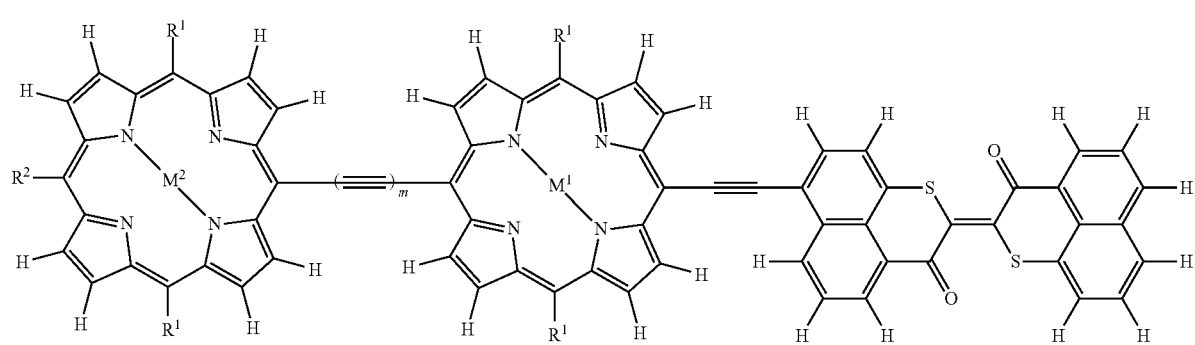
(xii)
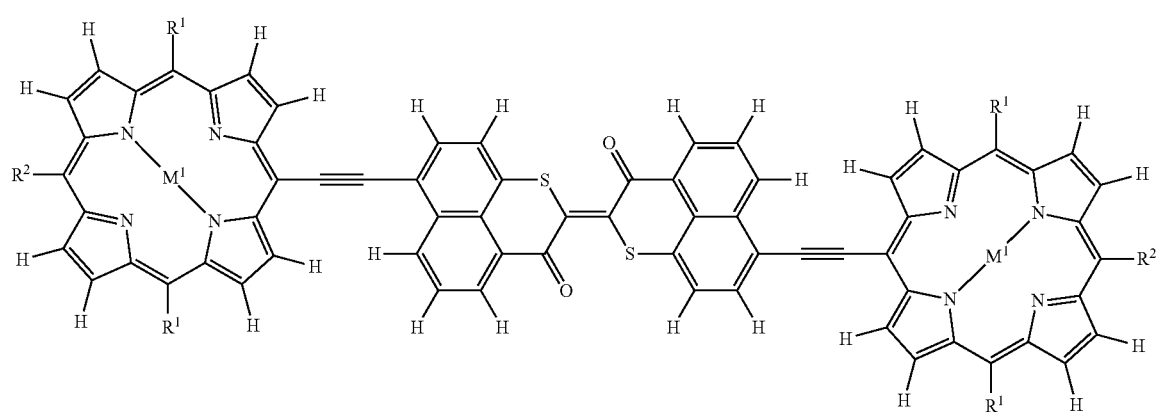
(xiii)
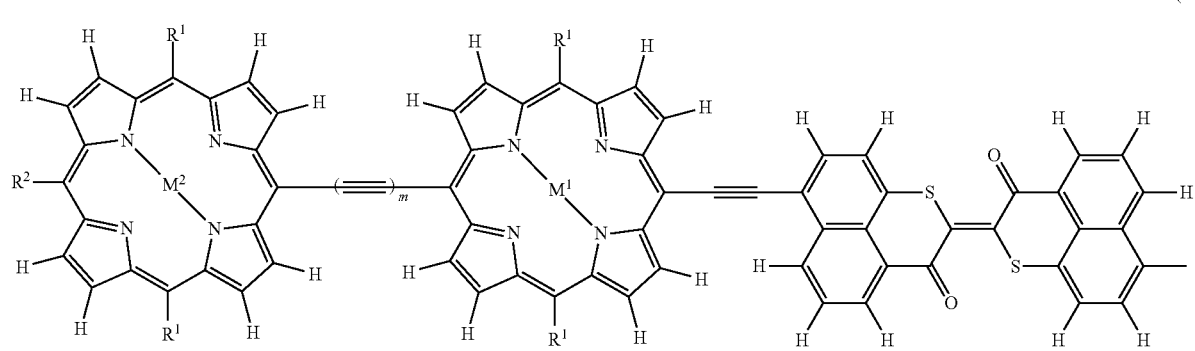
(xiv)

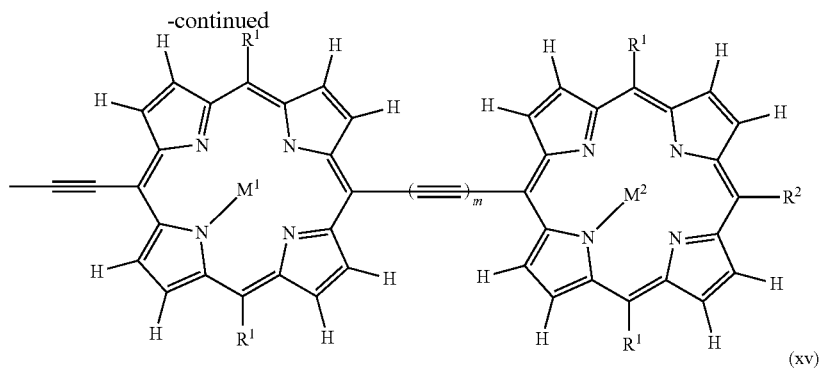

(xv)

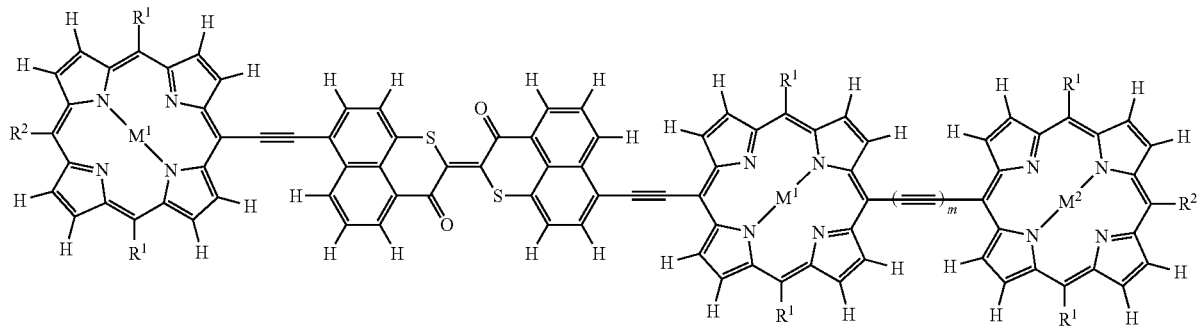

In the formulae (xi) to (xv),

M¹ denotes a metal ion or two hydrogen atoms, and when the formula (1) contains a plurality of M¹s, the respective M¹s can be identical to or different from each other.

In the formulae (xii), (xiv), and (xv),

M² denotes a metal ion or two hydrogen atoms, M¹ and M² can be identical to or different from each other, and when the formula (1) contains a plurality of M²s, the respective M²s can be identical to or different from each other.

Further preferably, a compound of the present invention having the structure (i), (ii), (iii), (iv), or (v) is, for example, a porphyrin compound, a tautomer or stereoisomer thereof, or a salt thereof, with the porphyrin compound being represented by one of the following formulae (xxi) to (xxv) in which in the formulae $(a^1)$, $(b^1)$, $(a^3)$, and $(b^3)$, $L^0$ denotes an ethynylene group, $R^2$s are all hydrogen atoms, and $R^3$s are all hydrogen atoms, in the formulae $(b^1)$ and $(b^3)$, $L^1$ is an ethynylene group, and in the formula $(c^2)$, $R^4$s are all hydrogen atoms.

(xxi)

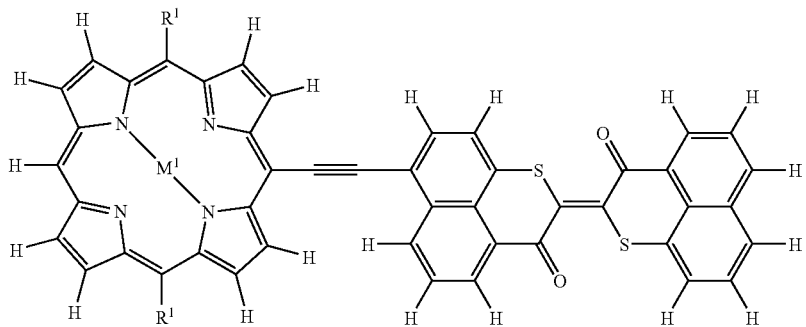

(xxii)

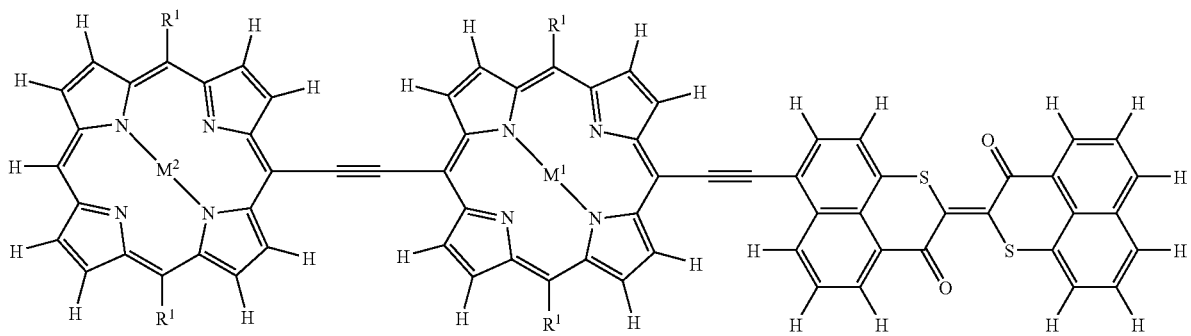

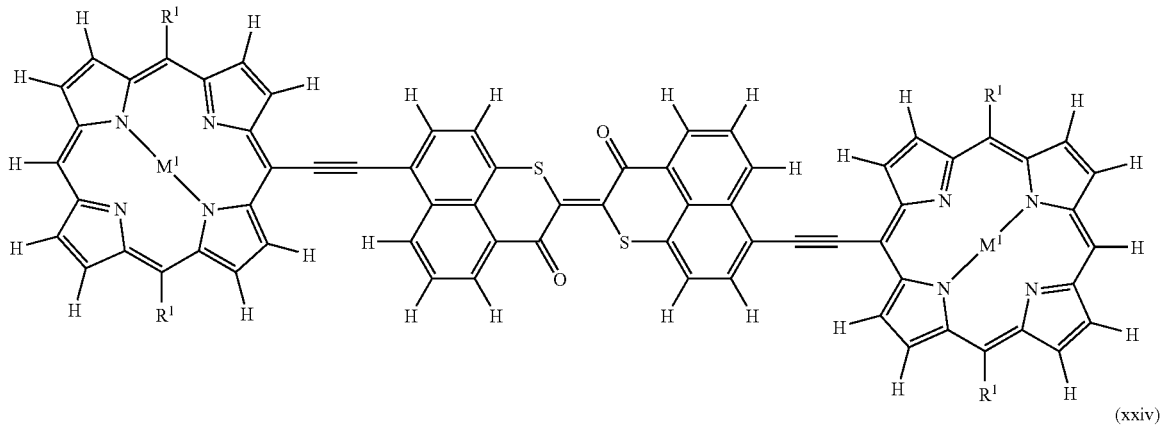

(xxiii)

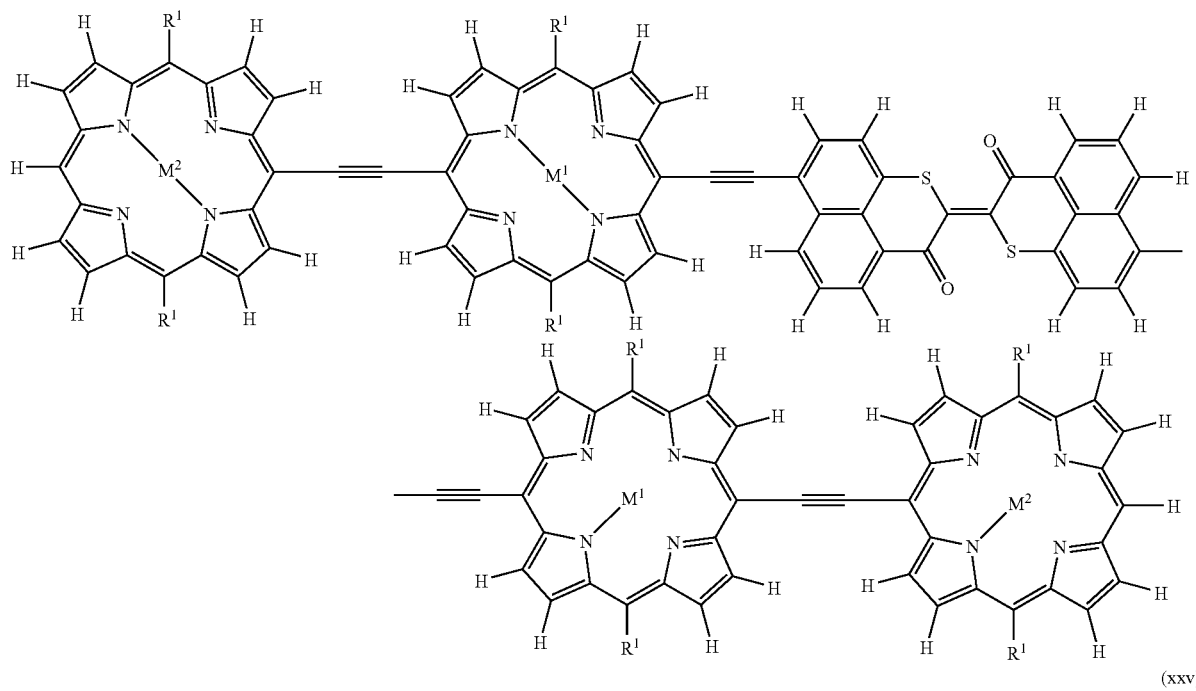

(xxiv)

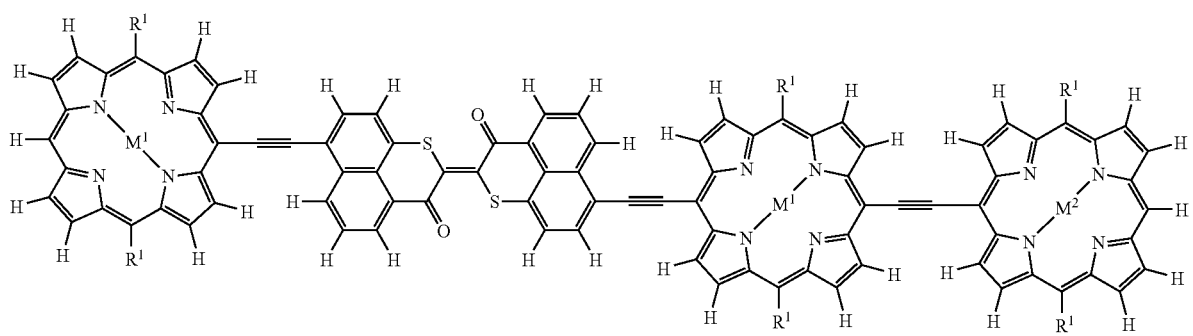

(xxv)

In the formulae (xxi) to (xxv), $R^1$s each are at least one selected from the group consisting of a hydrogen atom, a methyl group, an ethyl group, an n-propyl group, an isopropyl group, an n-butyl group, a sec-butyl group, an isobutyl group, a tert-butyl group, a pentyl group, a hexyl group, a phenyl group, a 4-methoxycarbonylphenyl group, a 3,5-bis(methoxycarbonyl)phenyl group, a 4-ethoxycarbonylphenyl group, and a 3,5-bis(ethoxycarbonyl)phenyl group, and the respective $R^1$s can be identical to or different from each other, and $M^1$ denotes Zn(II), Ga(III), Fe(II), Fe(III), Co(II), Co(III), Ru(II), Ru(III), or two hydrogen atoms, and when the formula (1) contains a plurality of $M^1$s, the respective $M^1$s can be identical to or different from each other.

In the formulae (xxii), (xxiv), and (xxv),
$M^2$ denotes Zn(II), Ga(III), Fe(II), Fe(III), Co(II), Co(III), Ru(II), Ru(III), or two hydrogen atoms, $M^1$ and $M^2$ can be identical to or different from each other, and when the formula (1) contains a plurality of $M^2$s, the respective $M^2$s can be identical to or different from each other.

Among the compounds of the present invention having the structure (i), (ii), (iii), (iv), or (v), particularly preferable compounds are porphyrin compounds that are indicated by the compound numbers 1001 to 1012 in the following compound number table, tautomers or stereoisomers thereof, or salts thereof, for example. However, the aforementioned particularly preferable compounds are not limited thereto. In the following compound number table, the column "structure" indicates which one of the structures (i), (ii), (iii), (iv), and (v) each of the porphyrin compounds indicated by the compound numbers 1001 to 1012 has. The columns "$R^1$", "$R^2$", "$R^3$", "$R^4$", "$M^1$", "$M^2$", "$L^0$", and "$L^1$" indicate the structures of respective atomic groups.

perinaphthothioindigo rings is preferably 2 to 6 from the viewpoints of ease of production, handling, and use as a three-dimensional optical recording material, for example. The reason why the ease of use as a three-dimensional optical recording material can be obtained when the total number of porphyrin rings and perinaphthothioindigo rings is in the aforementioned range, is because the wavelength of one-photon absorption tends not to overlap with that of two-photon absorption. The total number of porphyrin rings and perinaphthothioindigo rings is more preferably 2 to 5, further preferably 2 to 4, and particularly preferably 3 or less (2 or 3). Conceivably, the two-photon absorption wavelength in the compounds of the present invention is in the near-infrared region, for example. More particularly, it is conceivable that the two-photon absorption wavelength is in the range around 860 to 890 nm that is about twice the wavelength of the Soret band of porphyrin. However, the present invention is not limited by this supposition. Examples of the compounds of the present invention in which the total number of porphyrin

TABLE 1

<Compound Number Table>

| Compound No. | Structure | $R^1$ | $R^2$ | $R^3$ | $R^4$ | $M^1$ | $M^2$ | $L^0$ | $L^1$ |
|---|---|---|---|---|---|---|---|---|---|
| 1001 | (i) | 4-(methoxy-carbonyl)-phenyl groups | hydrogen atom | hydrogen atoms | hydrogen atoms | Zn(II) | none | ethynylene group | none |
| 1002 | (ii) | 4-(methoxy-carbonyl)-phenyl groups | hydrogen atom | hydrogen atoms | hydrogen atoms | Zn(II) | Zn(II) | ethynylene group | ethynylene group |
| 1003 | (i) | 4-(ethoxycarbonyl)-phenyl groups | hydrogen atom | hydrogen atoms | hydrogen atoms | Zn(II) | none | ethynylene group | none |
| 1004 | (ii) | 4-(ethoxycarbonyl)-phenyl groups | hydrogen atom | hydrogen atoms | hydrogen atoms | Zn(II) | Zn(II) | ethynylene group | ethynylene group |
| 1005 | (i) | 2-ethyl-n-pentyl groups | hydrogen atom | hydrogen atoms | hydrogen atoms | Zn(II) | none | ethynylene group | none |
| 1006 | (ii) | 2-ethyl-n-pentyl groups | hydrogen atom | hydrogen atoms | hydrogen atoms | Zn(II) | Zn(II) | ethynylene group | ethynylene group |
| 1007 | (i) | n-heptyl groups | hydrogen atom | hydrogen atoms | hydrogen atoms | Zn(II) | none | ethynylene group | none |
| 1008 | (ii) | n-heptyl groups | hydrogen atom | hydrogen atoms | hydrogen atoms | Zn(II) | Zn(II) | ethynylene group | ethynylene group |
| 1009 | (ii) | 4-(methoxy-carbonyl)-phenyl groups | hydrogen atom | hydrogen atoms | hydrogen atoms | Zn(II) | two hydrogen atoms | ethynylene group | ethynylene group |
| 1010 | (ii) | 4-(ethoxycarbonyl)-phenyl groups | hydrogen atom | hydrogen atoms | hydrogen atoms | Zn(II) | two hydrogen atoms | ethynylene group | ethynylene group |
| 1011 | (ii) | 2-ethyl-n-pentyl groups | hydrogen atom | hydrogen atoms | hydrogen atoms | Zn(II) | two hydrogen atoms | ethynylene group | ethynylene group |
| 1012 | (ii) | n-heptyl groups | hydrogen atom | hydrogen atoms | hydrogen atoms | Zn(II) | two hydrogen atoms | ethynylene group | ethynylene group |

In the compounds of the present invention, the total number of porphyrin rings and perinaphthothioindigo rings is not particularly limited. The total number of porphyrin rings and rings and perinaphthothioindigo rings is 3 or less include the following (vi) and (vii) in addition to the aforementioned (i) to (iii).

(vi) Compound in which P¹ is represented by the formula (c¹), [Y] is represented by the formula (c²), and P² is represented by the formula (a³)

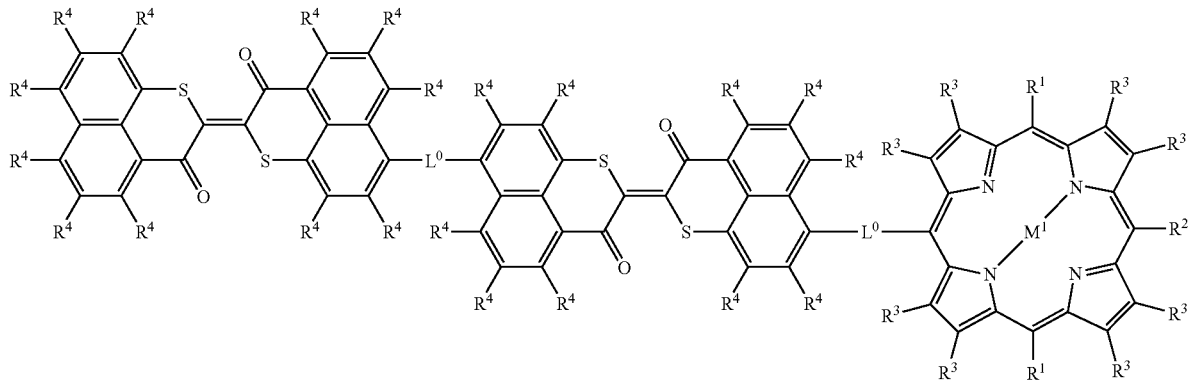

(vii) Compound in which P¹ is represented by the formula (c¹), [Y] is represented by the formula (a²), and P² is represented by the formula (c³)

atoms, for example. The metal ion is not particularly limited. However, the metal ion is more preferably an ion of zinc, iron, cobalt, ruthenium, or gallium, and further preferably Zn(II), (vi)

Ga(III), Fe(II), Fe(III), Co(II), Co(III), Ru(II), or Ru(III). When the formula (1) contains a plurality of $M^2$s, the respective $M^2$s can be identical to or different from each other.

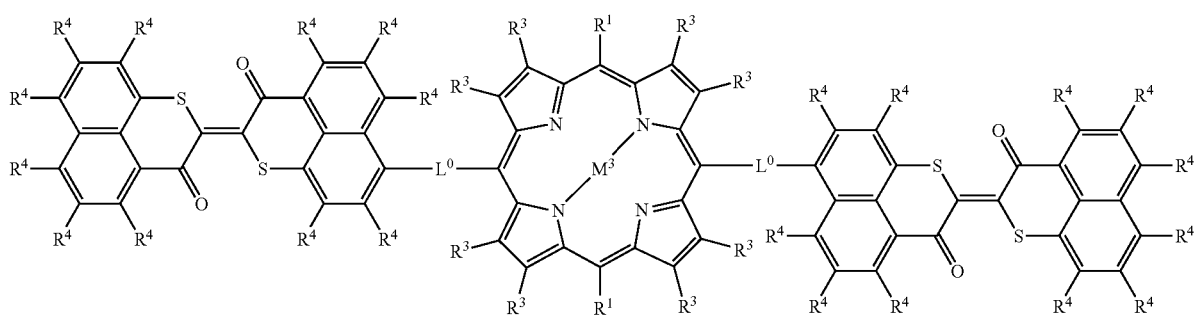

(vii)

Furthermore, in the compounds of the present invention each having the structure (i), (ii), (iii), (iv), (v), (vi), or (vii), particularly preferably, $R^3$ and $R^4$ are all hydrogen atoms, $M^1$ denotes a metal ion or two hydrogen atoms, when $M^2$ is present, $M^2$ denotes a metal ion or two hydrogen atoms, $L^0$ denotes an ethynylene group (—C≡C—), and $L^1$ is represented by the aforementioned formula ($L^{200}$), for example.

As described above, in the formula (1), each $M^1$ in the aforementioned formulae (a¹), (b¹), (a³), and (b³) indicates metal, metal halide, metal oxide, metal hydroxide, Si, Ge, or P, or two hydrogen atoms. $M^1$ can be electroneutral or in the ionic state, for example. Each $M^1$ denotes preferably a metal ion or two hydrogen atoms, for example. The metal ion is not particularly limited. However, the metal ion is more preferably an ion of zinc, iron, cobalt, ruthenium, or gallium, and further preferably Zn(II), Ga(III), Fe(II), Fe(III), Co(II), Co(III), Ru(II), or Ru(III). When the formula (1) contains a plurality of $M^1$s, the respective $M^1$s can be identical to or different from each other.

As described above, in the formula (1), each $M^2$ in the formulae (b¹) and (b³) denotes metal, metal halide, metal oxide, metal hydroxide, Si, Ge, or P, or two hydrogen atoms. $M^2$ can be electroneutral or in the ionic state, for example. Each $M^2$ denotes preferably a metal ion or two hydrogen Furthermore, as described above, in the formula (1), each $M^3$ in the formulae (a²) and (b²) denotes metal, metal halide, metal oxide, metal hydroxide, Si, Ge, or P, or two hydrogen atoms. $M^3$ can be electroneutral or in the ionic state, for example. Each $M^3$ denotes preferably a metal ion or two hydrogen atoms, for example. The metal ion is not particularly limited. However, the metal ion is more preferably an ion of zinc, iron, cobalt, ruthenium, or gallium, and further preferably Zn(II), Ga(III), Fe(II), Fe(III), Co(II), Co(III), Ru(II), or Ru(III). When a plurality of $M^3$s are present, the respective $M^3$s can be identical to or different from each other.

The state of bonding between each $M^1$, each $M^2$, or each $M^3$ and a nitrogen atom of a porphyrin ring (pyrrole nucleus) is not particularly limited. When each $M^1$, each $M^2$, or each $M^3$ denotes two hydrogen atoms, the state of bonding is preferably a covalent bond, for example. On the other hand, when each $M^1$, each $M^2$, or each $M^3$ denotes other than two hydrogen atoms, for example, metal, the state of bonding is preferably a coordinate bond, for example.

Preferable examples of $R^1$ in the formulae (a¹), (b¹), (a²), (b²), (a³), and (b³) in the formula (1) are indicated below. In addition, preferable examples of $R^3$ as well as $R^2$ in the formulae (a¹), (b¹), (a³), and (b³) also are indicated below.

In $R^1$, the substituted alkyl group is not particularly limited. Preferably, the substituted alkyl group is at least one selected from the group consisting of an alkoxycarbonylalkyl group, an alkoxyalkyl group, an alkenoxyalkyl group, an alkenoxycarbonylalkyl group, and a carboxyalkyl group. The same applies to the substituted alkyl groups in $R^2$ and $R^3$. As described above, it should be understood that "a substituted or non-substituted alkyl group" in $R^1$, $R^2$, and $R^3$ in the formula (1) also embraces one with a cyclic structure, i.e. a substituted or non-substituted cycloalkyl group.

In $R^1$, the number of carbon atoms of an alkyl residue in the substituted or non-substituted alkyl group is not particularly limited. From the viewpoints of ease of production, solubility, etc. of the compounds according to the present invention, the number of carbon atoms of an alkyl residue is preferably 1 to 24, more preferably 2 to 10, and further preferably 3 to 8. The same applies in $R^2$. From the same viewpoints, in $R^1$, the number of carbon atoms of a substituent in the substituted alkyl group is preferably 1 to 24, more preferably 1 to 10, and further preferably 1 to 5. The same applies in $R^2$. Furthermore, from the same viewpoints, in $R^1$, the total number of carbon atoms of the substituted or non-substituted alkyl group is preferably 1 to 24, more preferably 4 to 18, and further preferably 4 to 13. The same applies in $R^2$ and $R^3$.

The non-substituted alkyl group in $R^1$ is not particularly limited. However, the non-substituted alkyl group is particularly preferably at least one selected from the group consisting of a methyl group, an ethyl group, an n-propyl group, an isopropyl group, an n-butyl group, a sec-butyl group, an isobutyl group, a tert-butyl group, a pentyl group, a hexyl group, an n-heptyl group, and a 2-ethyl-n-pentyl group, for example. The same applies in $R^2$ and $R^3$.

The substituted alkyl group in $R^1$ is not particularly limited. The substituted alkyl group is particularly preferably at least one selected from the group consisting of a carboxymethyl group, a carboxyethyl group, a carboxy-n-propyl group, a carboxyisopropyl group, a carboxy-n-butyl group, a carboxy-sec-butyl group, a carboxyisobutyl group, a carboxy-tert-butyl group, a carboxypentyl group, a carboxyhexyl group, a methoxycarbonyl group, a methoxycarbonylethyl group, a methoxycarbonylethyl-n-propyl group, an ethoxycarbonylethyl group, an ethoxycarbonylethylpropyl group, an allyloxycarbonylethyl group, an allyloxycarbonylethyl-n-propyl group, an allyloxypropyl group, an allyloxyethyl group, and an allyloxybutyl group, for example. The same applies in $R^2$ and $R^3$.

In $R^1$, the aryl residue in the substituted or non-substituted aryl group is not particularly limited. The aryl residue is preferably at least one selected from the group consisting of a phenyl group, a naphthyl group, a pyridyl group, an azulenyl group, and an anthracenyl group, for example. The same applies in $R^2$ and $R^3$.

In $R^1$, the number of carbon atoms of the aryl residue in the substituted or non-substituted aryl group is not particularly limited. From the viewpoints of ease of production, solubility, etc. of the compounds according to the present invention, the number of carbon atoms of the aryl residue is preferably 5 to 24 and more preferably 5 to 10. The same applies in $R^2$ and $R^3$.

In $R^1$, the number of carbon atoms of the substituent in the substituted aryl group is not particularly limited. From the viewpoints of ease of production, solubility, etc. of the compounds according to the present invention, the number of carbon atoms of the substituent is preferably 1 to 40. Compounds of the present invention in which the number of carbon atoms of the substituent in the substituted aryl group is in the above-mentioned range are relatively easy to produce. The number of carbon atoms of the substituent in the substituted aryl group is preferably 1 to 20 and further preferably 1 to 10. The same applies in $R^2$ and $R^3$.

In $R^1$, the total number of carbon atoms of the substituted or non-substituted aryl group is not particularly limited. From the viewpoints of ease of production, solubility, etc. of the compounds according to the present invention, the total number of carbon atoms is preferably 5 to 24 and more preferably 5 to 10. The same applies in $R^2$ and $R^3$.

In $R^1$, the substituted aryl group is not particularly limited. The substituted aryl group is preferably at least one selected from the group consisting of an alkylaryl group, an alkoxyaryl group, an alkoxycarbonylaryl group, an alkenoxyaryl group, a carboxyaryl group, and an alkenoxycarbonylaryl group. The same applies to the substituted aryl groups in $R^2$ and $R^3$.

In $R^1$, the substituent in the substituted aryl group is not particularly limited. The substituent is particularly preferably at least one selected from the group consisting of a methyl group, an ethyl group, an n-propyl group, an isopropyl group, an n-butyl group, a sec-butyl group, an isobutyl group, a tert-butyl group, a pentyl group, a hexyl group, a methoxy group, an ethoxy group, an n-propoxy group, an isopropoxy group, an n-butoxy group, a sec-butoxy group, an isobutoxy group, a tert-butoxy group, a pentyloxy group, a hexyloxy group, a carboxymethyl group, a carboxyethyl group, a carboxy-n-propyl group, a carboxyisopropyl group, a carboxy-n-butyl group, a carboxy-sec-butyl group, a carboxyisobutyl group, a carboxy-tert-butyl group, a carboxypentyl group, a carboxyhexyl group, a methoxycarbonyl group, an ethoxycarbonyl group, an n-propoxycarbonyl group, an isopropoxycarbonyl group, an n-butoxycarbonyl group, a sec-butoxycarbonyl group, an isobutoxycarbonyl group, a tert-butoxycarbonyl group, a pentyloxycarbonyl group, and a hexyloxycarbonyl group. The same applies in $R^2$ and $R^3$.

In $R^1$, the substituted aryl group is particularly preferably at least one selected from the group consisting of a 4-carboxyphenyl group, a 3,5-dicarboxyphenyl group, a 4-carboxy-2,6-bis(carboxymethoxy)phenyl group, a 3,5-bis(tris(carboxyethyl)methylcarboxyamide)phenyl group, a 4-(tris(carboxyethyl)methylcarboxyamide)-2,6-bis(tris(carboxyethyl)methyl-carboxyamidemethoxy)phenyl group, a 4-methoxycarbonylphenyl group, a 3,5-bis(methoxycarbonyl)phenyl group, a 4-ethoxycarbonylphenyl group, and a 3,5-bis(ethoxycarbonyl)phenyl group, for example. The same applies in $R^2$ and $R^3$.

$R^1$s in each of the formulae ($a^1$), ($b^1$), ($a^2$), ($b^2$), ($a^3$), and ($b^3$) can be identical to or different from each other. For example, from the viewpoint of ease of production of the compounds according to the present invention, all the $R^1$s in the formula ($a^1$) are preferably identical to each other. The same applies in the formulae ($b^1$), ($a^2$), ($b^2$), ($a^3$), and ($b^3$). When the formula (1) contains a plurality of $R^2$s, they can be identical to or different from each other. For example, all the $R^2$s are preferably identical to each other in the formula (1) and are more preferably hydrogen atoms.

Furthermore, in $R^2$, the number of carbon atoms of a ring in the five- or six-membered nitrogen-containing coordinating heteroaromatic ring is not particularly limited. From the viewpoints of ease of production, solubility, etc. of the compounds according to the present invention, the number of carbon atoms is preferably 3 to 5. In $R^2$, the number of nitrogen atoms of a ring in the five- or six-membered nitrogen-containing coordinating heteroaromatic ring is not particularly limited. From the viewpoints of ease of production, etc. of the compounds according to the present invention, the number of nitrogen atoms is preferably 1 to 2.

In $R^2$, the five- or six-membered nitrogen-containing coordinating heteroaromatic ring is not particularly limited. The five- or six-membered nitrogen-containing coordinating heteroaromatic ring is at least one selected from the group consisting of imidazole, N-methylimidazole, pyridine, pyrazole, and pyrimidine, for example.

In the formula (1), $R^3$s in the formulae ($a^1$), ($b^1$), ($a^2$), ($b^2$), ($a^3$), and ($b^3$) are not particularly limited. From the viewpoints of ease of production, solubility, etc. of the compounds according to the present invention, all the $R^3$s are preferably identical to each other and are more preferably hydrogen atoms.

In the formula (1), $R^4$s in the formulae ($c^1$), ($c^2$), and ($c^3$) are not particularly limited. From the viewpoints of ease of production, solubility, etc. of the compounds according to the present invention, all the $R^4$s are preferably hydrogen atoms, for example.

When isomers of the porphyrin compound represented by the formula (1) exist including a tautomer, a stereoisomer, etc, these isomers also are included in the compounds of the present invention. More specifically, examples of the isomers include a geometrical isomer, a conformational isomer, an optical isomer, etc. For example, the perinaphthothioindigo ring indicated in the formula (1) has a trans configuration. However, a compound in which the perinaphthothioindigo ring has been isomerized into a cis configuration in the formula (1) also is included in the compounds of the present invention. Furthermore, for example, when a compound of the present invention has an enantiomer, both the R-form and S-form thereof are included in the compounds of the present invention. In addition, when a porphyrin compound represented by the formula (1) or an isomer thereof can form a salt, the salt also is included in the compounds of the present invention. In the salt, the counterion of the porphyrin compound represented by the formula (1) is not particularly limited. The counterion can be either a positive ion or a negative ion, for example. Examples of the negative ion include a phosphoric acid hexafluoride ion ($PF_6^-$), a tetrafluoroborate ion ($BF_4^-$), a hydroxide ion ($OH^-$), an acetate ion, a carbonate ion, a phosphate ion, a sulphate ion, a nitrate ion, halide ions (for instance, a fluoride ion ($F^-$), a chloride ion ($Cl^-$), a bromide ion ($Br^-$), an iodide ion ($I^-$), etc.), hypohalous acid ions (for instance, a hypofluorous acid ion, a hypochlorous acid ion, a hypobromous acid ion, a hypoiodous acid ion, etc.), halorous acid ions (for instance, a fluorous acid ion, a chlorous acid ion, a bromous acid ion, an iodous acid ion, etc.), halogenic acid ions (for instance, a fluoric acid ion, a chloric acid ion, a bromic acid ion, an iodic acid ion, etc.), perhalogenate ions (for instance, a perfluorate ion, a perchlorate ion, a perbromate ion, a periodate ion, etc.), a trifluoromethanesulfonate ion ($OSO_2CF_3-$), a tetrakispentafluorophenylborate ion $[B(C_6F_5)_4-]$, etc. The positive ion is not particularly limited. Examples thereof include a hydrogen ion and various metal ions such as a lithium ion, a magnesium ion, a sodium ion, a potassium ion, a calcium ion, a barium ion, a strontium ion, an yttrium ion, a scandium ion, a lanthanoid ion, etc. These counterions may be of one type, or two types or more of them may be present in combination.

A particularly preferred compound as a compound of the present invention is, for instance, a porphyrin compound represented by the following formula (2) or (3), a tautomer or stereoisomer thereof, or a salt thereof. As described above, for instance, a porphyrin compound indicated by any one of the compound numbers 1001 to 1012 in the compound number table, a tautomer or stereoisomer thereof, or a salt thereof also is particularly preferred as a compound of the present invention.

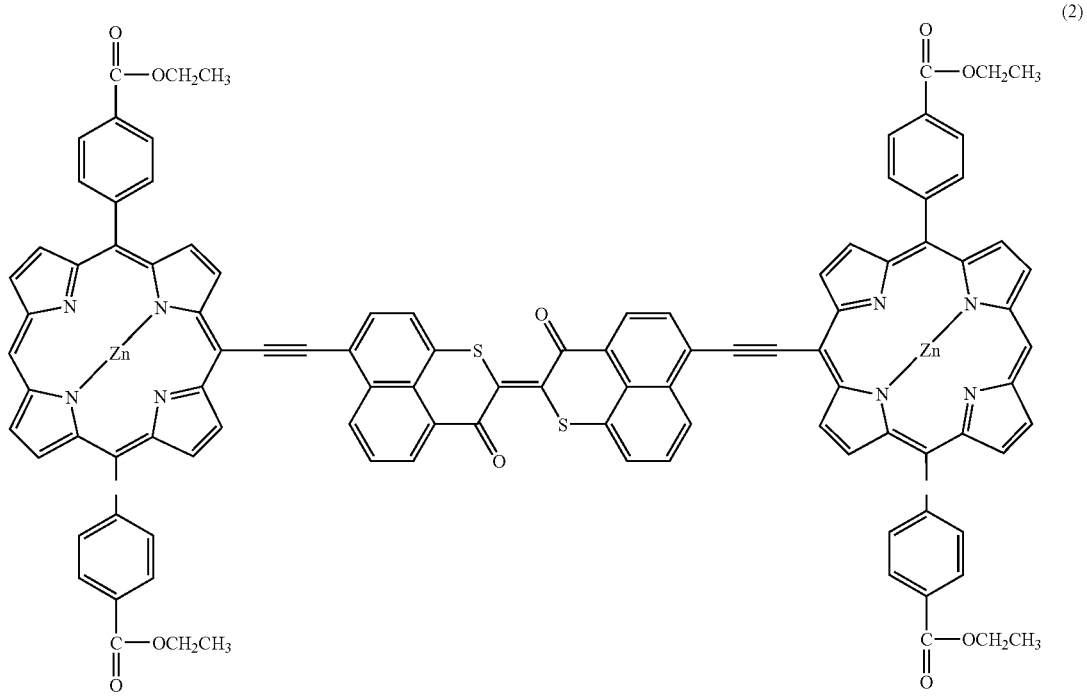

(3)

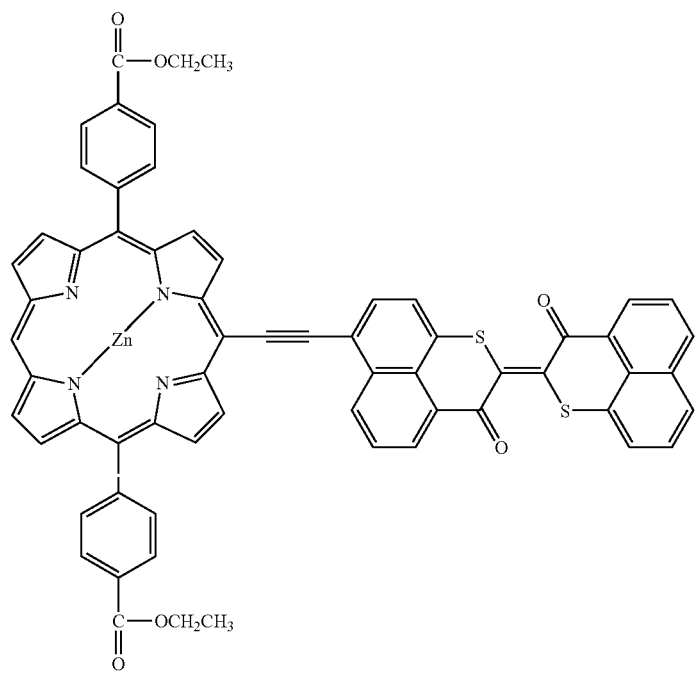

[Process for Producing a Compound of the Present Invention]

Next, a process for producing a compound of the present invention is described.

The process for producing a compound of the present invention is not particularly limited. That is, the compound of the present invention can be produced by any processes. Preferably, the compound of the present invention is produced by a production process of the present invention described below, for example.

The production process of the present invention is a process for producing a porphyrin compound represented by the formula (1), a tautomer or stereoisomer thereof, or a salt thereof. More particularly, the production process of the present invention include allowing a porphyrin derivative and a perinaphthothioindigo halide derivative to undergo a coupling reaction therebetween, the porphyrin derivative is a derivative in which at least one of hydrogen atoms that are bonded to carbons located at positions 5, 10, 15, and 20 of a porphyrin ring has been substituted by a substituent -L⁰-H, and the L⁰ is identical to the L⁰ according to claim 1, and the perinaphthothioindigo halide derivative is a derivative in which a para position carbon of a carbon bonded to a S atom has been halogenated in at least one of two naphthalene rings in a perinaphthothioindigo ring.

In this case, "a para position carbon of a carbon bonded to a S atom" in the perinaphthothioindigo halide derivative denotes a carbon atom indicated with the mark * in the following formula (100). In the formula (100), $X^1$ and $X^2$ can be identical to or different from each other. At least one of $X^1$ and $X^2$ is a halogen. The formula (100) is a mere example of the structure of the perinaphthothioindigo halide derivative. As described above, in the present invention, the perinaphthothioindigo halide derivative is a derivative in which a para position carbon of a carbon bonded to a S atom has been halogenated in at least one of two naphthalene rings in a perinaphthothioindigo ring. Other than that, the structure of the perinaphthothioindigo halide derivative is not particularly limited. Examples of the structure of the perinaphthothioindigo halide derivative include a structure represented by the following formula (200). In the formula (200), $X^1$ and $X^2$ can be identical to or different from each other. At least one of $X^1$ and $X^2$ is a halogen. $R^4$ is the same as that in the formulae ($c^1$), ($c^2$), and ($c^3$).

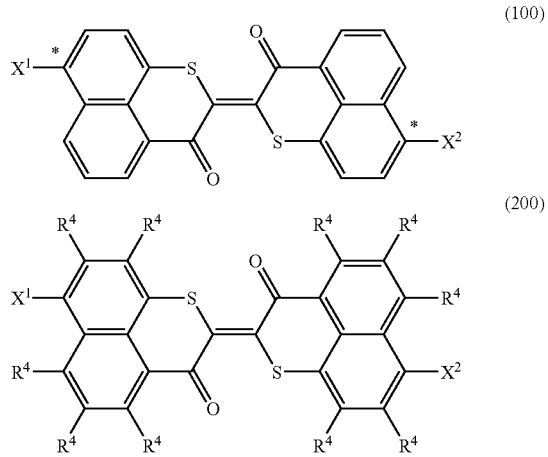

In the aforementioned porphyrin derivative, "carbons located at positions 5, 10, 15, and 20 of a porphyrin ring" denote carbon atoms indicated with numerals 5, 10, 15, and 20 in the following formula (300), respectively. The following formula (300) is a diagram simply showing the basic skeleton of a porphyrin ring. The structure of the porphyrin derivative in the present invention is not limited by the formula (300). As described above, in the present invention, the porphyrin derivative is a derivative in which at least one of hydrogen atoms that are bonded to carbons located at positions 5, 10, 15, and 20 of a porphyrin ring has been substituted by a substituent -L⁰-H. The L⁰ is identical to the L⁰ described in claim 1. Other than that, the structure of the porphyrin derivative is not particularly limited.

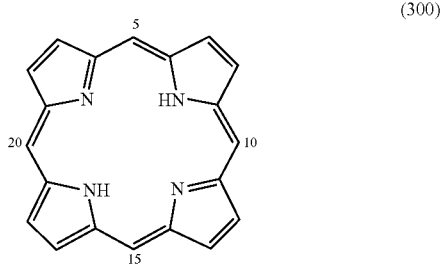

(300)

In Scheme 2 shown below, an example of the production process of the present invention is shown. Scheme 2 is a scheme showing an example of the process of producing a porphyrin compound (a compound (600) in Scheme 2, which is identical to the compound represented by the formula (i)) selected from the porphyrin compounds represented by the formula (1), wherein in the aforementioned porphyrin compound, [Y] is represented by the formula (c²), P¹ is represented by the formula (a¹), and P² denotes a hydrogen atom. As shown in Scheme 2, this porphyrin compound can be produced through a coupling reaction between a porphyrin derivative (400) and a perinaphthothioindigo halide derivative (500). In Scheme 2, R¹, R², R³, M¹, and L⁰ are the same as those in the formula (a¹), R⁴ is the same as that in the formula (c²), and X¹ denotes a halogen. Among porphyrin compounds represented by the formula (1), porphyrin compounds having other structures also can be produced according to the process described above. That is, any person skilled in the art of the present invention can produce the compounds of the present invention based on the illustration shown in Scheme 2 below and the structures of the compounds of the present invention described above, without carrying out an excessive amount of trial and error, complicated and sophisticated experiments, etc. Specifically, among the porphyrin compounds represented by the formula (1), the other compounds each also contain a porphyrin ring and a perinaphthothioindigo ring that are bonded to each other with L⁰ as in the following compound (600). Accordingly, the aforementioned other compounds also can be produced using the similar coupling reaction to that shown in Scheme 2. Furthermore, for example, a compound in which a plurality of porphyrin rings are linked to each other with the L¹ or L² can be used as a raw material instead of the compound (400). This makes it possible to produce a compound in which at least one of the formulae (b¹), (b²), and (b³) is contained in the formula (1). Any person skilled in the art can produce the raw material compound in which a plurality of porphyrin rings are linked to each other with the L¹ or L², based on the description of the present specification (in consideration of common knowledge in the art of the present invention in some cases) without carrying out an excessive amount of trial and error, complicated and sophisticated experiments, etc. Such compounds are disclosed in JP2004-168690A, for example. Hence, the compounds can be produced by, for instance, the process disclosed in JP2004-168690A.

Scheme 2

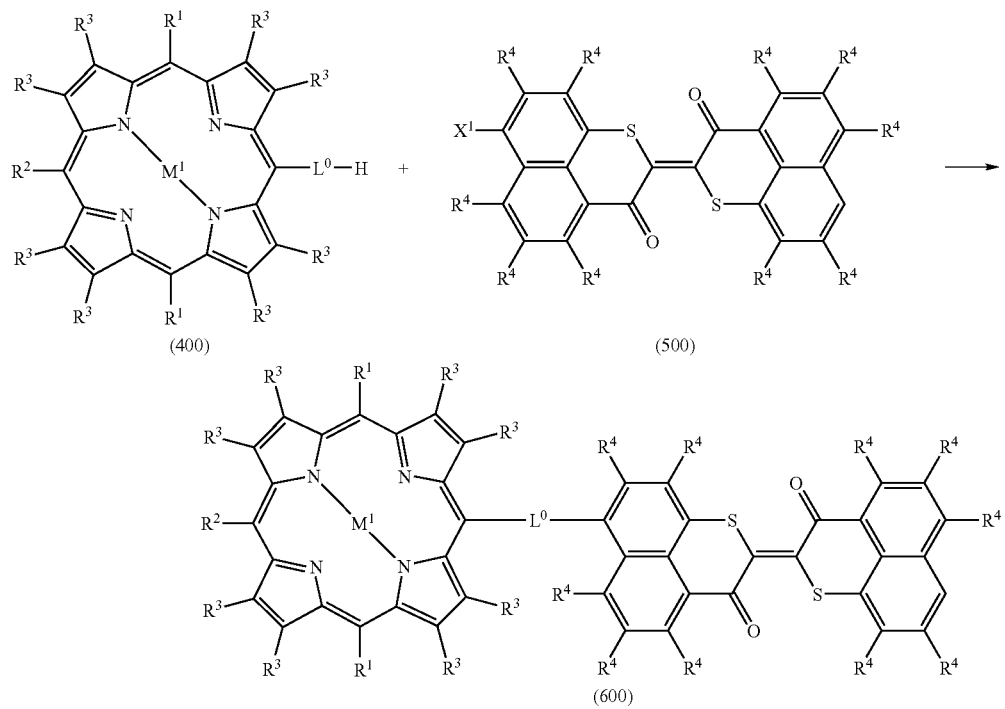

The production process of the present invention is not limited to the process of Scheme 2. For instance, the respective substituents have been introduced before the coupling reaction in Scheme 2. However, the respective substituents may be introduced, converted, protected, or deprotected suitably after the coupling reaction, for example. Furthermore, for instance, in Scheme 2, the perinaphthothioindigo halide derivative (500) may be replaced by a perinaphthothioindigo halide derivative represented by the formula (200). This allows a compound of the present invention represented by the formula (ii) to be obtained, for example. Moreover, even if using the perinaphthothioindigo halide derivative (200) as described above, a porphyrin derivative of the present invention represented by the formula (600) (the formula (i)) can be obtained depending on the reaction conditions.

Furthermore, the conditions for the coupling reaction also are not limited in the production process of the present invention. For instance, the conditions such as the reaction solvent, temperature, reaction time, etc. for the coupling reaction may be determined suitably with reference to known similar reactions. The reaction solvent for the coupling reaction can be water or an organic solvent, for example. Examples of the organic solvent include: nitriles such as benzonitrile, acetonitrile, butyronitrile, etc.; halogenated solvents such as chloroform, dichloromethane, dichloroethane, carbon tetrachloride, tetrachloroethane, etc.; ethers such as THF (tetrahydrofuran), diethyl ether, diethylene glycol monomethyl ether, diethylene glycol dimethyl ether, diethylene glycol monoethyl ether, diethylene glycol diethyl ether, etc.; amides such as DMF (dimethylformamide), DMA (dimethylacetamide), etc.; sulfoxides such as DMSO (dimethylsulfoxide), etc.; ketones such as acetone, methyl ethyl ketone, methyl isobutyl ketone, etc.; and alcohols such as methanol, ethanol, n-propanol, etc. These solvents can be used individually or two or more of them can be used in combination. Furthermore, the reaction temperature and reaction time for the coupling reaction can be determined suitably according to the structures of the porphyrin derivative and perinaphthothioindigo halide derivative that are used as raw materials, for example. The reaction temperature is, for instance, −50 to 200° C., preferably 0 to 120° C., and more preferably 20 to 100° C. The reaction time is, for example, 1 to 20,000 minutes, preferably 1 to 1,500 minutes, and more preferably 30 to 1,000 minutes. Any person skilled in the art can easily produce the porphyrin derivative and perinaphthothioindigo halide derivative that are used as raw materials for the compounds of the present invention, based on the description of the present specification (in consideration of common knowledge in the art of the present invention in some cases) without carrying out an excessive amount of trial and error, complicated and sophisticated experiments, etc. Alternatively, they are commercially available. For instance, they can be synthesized from commercial products with reference to known documents, etc.

In the production process of the present invention, $L^0$ in the porphyrin compound is not particularly limited. From the viewpoint of the reaction efficiency in the coupling reaction with the perinaphthothioindigo halide derivative, it is particularly preferable that $L^0$ be an ethynylene group, for example. The halogen in the perinaphthothioindigo halide derivative is not particularly limited. From the viewpoint of the reaction efficiency in the coupling reaction with the porphyrin compound, it is particularly preferable that the halogen be bromine or iodine.

The production process of the present invention is described further in detail using examples of synthesizing (producing) compounds represented by the formulae (2) and (3). The compounds represented by the formulae (2) and (3) can be synthesized according to Scheme 3 shown below, for example. However, the process for producing the compounds represented by the formulae (2) and (3) is not limited to Scheme 3. In the compound represented by the formula (2), in the formula (1), [Y] is represented by the formula ($c^2$), $P^1$ is represented by the structural formula ($a^1$), $P^2$ is represented by the structural formula ($a^3$), R's are all 4-ethoxycarbonylphenyl groups, $R^2$, $R^3$, and $R^4$ are all hydrogen atoms, $M^1$ denotes zinc, and $L^0$ indicates an ethynylene group. The compound represented by the formula (3) is identical to the compound represented by the formula (2) except that $P^2$ denotes a hydrogen atom. Compounds having the other structures in the formula (1) also can be produced according to Scheme 3, for example.

Scheme 3

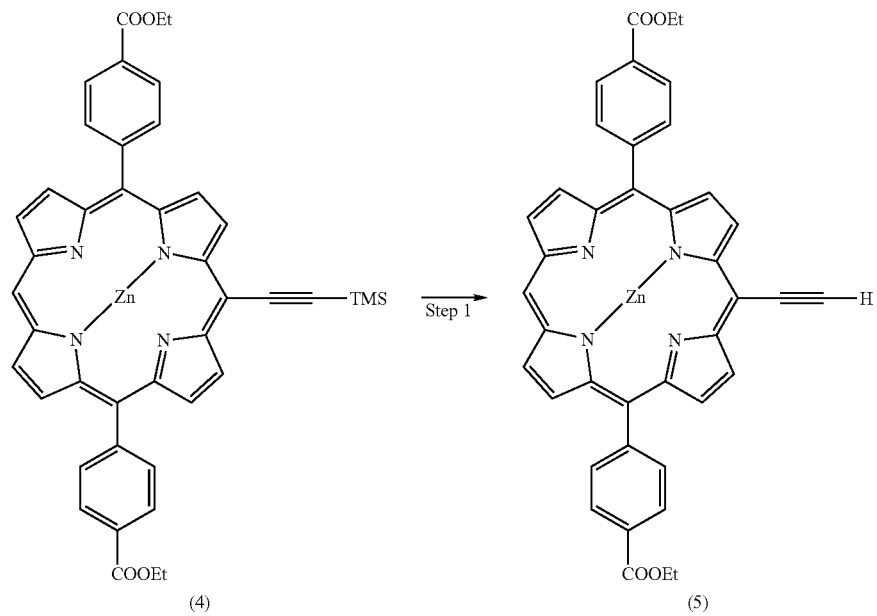

-continued
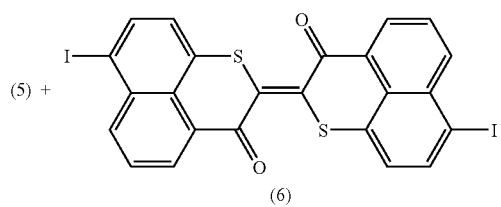
Step 2
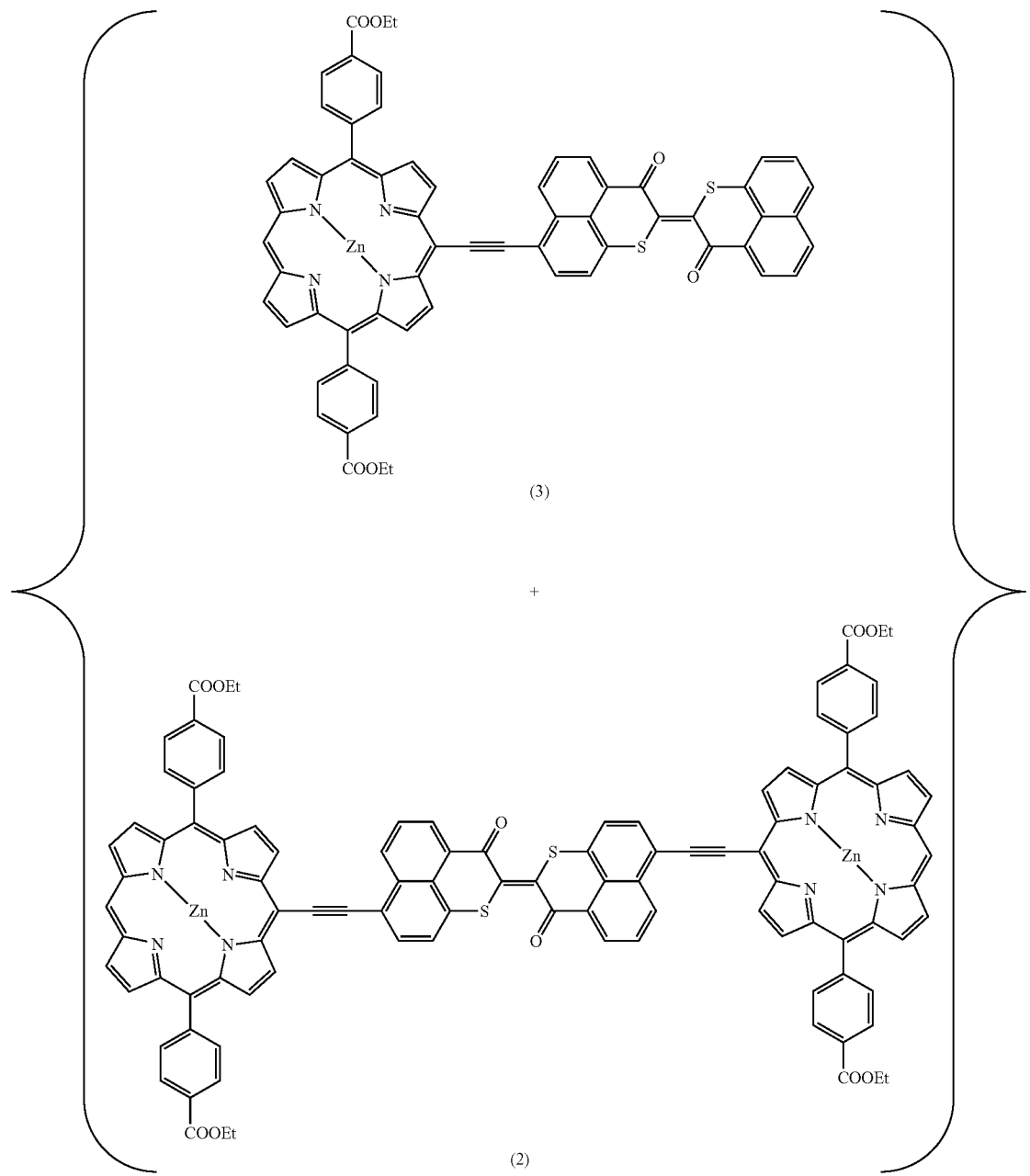

Hereinafter, Scheme 3 is described in detail. Various conditions such as the temperature, reaction time, amount of raw materials to be used, amount of solvents to be used, etc. are not limited by the following descriptions.

Step 1 shown above is a deprotection reaction of a TMS group (trimethylsilyl group). In this reaction, it is preferable that, for instance, 1 mL to 1000 mL of chloroform be used as a reaction solvent with respect to 32.0 mg of a compound (4). When consideration is given to the yield of the reaction, it is particularly preferable that the amount of chloroform to be used be 5 mL to 20 mL. The reaction solvent is not particularly limited as long as the deprotection reaction proceeds. For the reaction solvent, tetrahydrofuran (THF), methylene chloride, etc. can be used instead of chloroform. The deprotecting agent is not particularly limited. When consideration is given to the yield of the reaction, it is particularly preferable that the deprotecting agent be tetrabutylammonium fluoride. The equivalent number of the deprotecting agent with respect to the TMS group also is not particularly limited. When consideration is given to the yield of the reaction, the equivalent number is preferably 3 equivalents to 5 equivalents. The reaction temperature is not particularly limited. When consideration is given to the yield of the reaction, the reaction temperature is preferably 20° C. to 30° C.

Step 2 shown above is a coupling reaction between an aryl halide and an ethynyl group and is known as a Sonogashira reaction. In the Sonogashira reaction, it is preferable that 1 mL to 1000 mL of tetrahydrofuran (THF) be used as a reaction solvent with respect to 1.9 mg of the compound (6), for example. When consideration is given to the yield of the reaction, it is particularly preferable that the amount of THF to be used be 5 mL to 20 mL. The reaction solvent is not particularly limited as long as the reaction proceeds. For the reaction solvent, chloroform, methylene chloride, etc. can be used instead of THF. The base is not particularly limited. When consideration is given to the yield of the reaction, it is particularly preferable that the base be triethylamine. The amount of triethylamine is not particularly limited. For example, the amount of triethylamine is preferably 0.1 mL to 5 mL and more preferably 0.5 mL to 2 mL, with respect to 1.9 mg of the compound (6). The reaction catalyst is not particularly limited. A reaction catalyst can be used alone or a plurality of reaction catalysts can be used in combination. It is particularly preferable that for example, $Pd_2(dba)_3$ and $AsPh_3$ (dba=dibenzylideneacetone) be used in combination for the reaction catalyst. The equivalent number of $Pd_2(dba)_3$ with respect to the compound (6) is not particularly limited. When consideration is given to the yield of the reaction, the equivalent number is preferably 0.1 equivalent to 5 equivalents and more preferably 0.1 equivalent to 1 equivalent. The equivalent number of $AsPh_3$ with respect to the compound (6) is not particularly limited. When consideration is given to the yield of the reaction, the equivalent number is preferably 0.8 equivalent to 25 equivalents and more preferably 0.8 equivalent to 5 equivalents. The reaction temperature is not particularly limited. When consideration is given to the yield of the reaction, it is particularly preferable that the reaction temperature be 20° C. to 30° C.

Any person skilled in the art also can easily produce compounds having structures other than those described above among the compounds of the present invention, based on the description of the present specification (in consideration of common knowledge in the art of the present invention in some cases) without carrying out an excessive amount of trial and error as well as complicated and sophisticated experiments. For example, general porphyrin compounds represented by the formula (1) can be produced through the coupling reaction between a porphyrin derivative and a perinaphthothioindigo halide derivative based on the description above (in consideration of common knowledge in the art of the present invention in some cases). Specifically, it also is possible to produce them according to Scheme 3, for example. Furthermore, salts of the porphyrin compounds represented by the formula (1) can be produced by suitably adding appropriate acid or base to the porphyrin compounds that are represented by the formula (1) and that have been produced.

[Uses of the Compounds According to the Present Invention]

As described above, in the compounds of the present invention, a porphyrin ring and a perinaphthothioindigo ring are linked to each other with a straight-chain atomic group. The compounds of the present invention each can have pi-electron conjugation between the porphyrin ring and the perinaphthothioindigo ring. This allows the compounds of the present invention to have a high two-photon absorption efficiency and to effectively undergo photochromism by optical absorption. It also is possible for the compounds of the present invention to have a two-photon absorption cross section as large as 10000 GM or more when using a nanosecond pulsed laser, for example. The compounds of the present invention have such a high two-photon absorption efficiency. However, the aforementioned value, 10000 GM or more, does not limit the present invention in any way. The two-photon absorption cross section, the two-photon absorption efficiency, etc. vary according to the structures of the compounds of the present invention and measurement conditions. They are not particularly limited.

The compounds of the present invention undergo isomerization, i.e. photochromism, by two-photon absorption and thereby can be used as three-dimensional optical recording materials. Specifically, for instance, it is preferable that the compounds of the present invention can be isomerized in a solid state by two-photon absorption. However, the compounds of the present invention can be used as three-dimensional optical recording materials even when they can be isomerized in a solution state by two-photon absorption, for example. The two-photon absorption generates a high excitation state by simultaneously absorbing two photons of low energy in a near-infrared wavelength range where one-photon absorption does not occur. Accordingly, as described above, this allows two-photon absorption to selectively occur only in a position with a high optical density such as a focal point in an optical recording material. Hence, two-photon absorption allows optical absorption to be controlled, with the three-dimensional position being selected in the optical recording material. Thus, three-dimensional recording is possible that also utilizes the thickness direction of the optical recording material. When a compound of the present invention is used as a three-dimensional optical recording material, it can be used by being irradiated with a laser beam with a wavelength at which two-photon absorption occurs but one-photon absorption does not occur, for example.

As described above, examples of the use of the compounds according to the present invention include three-dimensional optical recording materials and three-dimensional optical recording media. Specifically, for example, a medium for a rewritable three-dimensional optical memory can be provided. Furthermore, in case the compounds of the present invention each have a two-photon absorption cross section as large as 10000 GM or more as described above, for instance, it is possible to record information with high density, specifically 1 terabit per 1 $cm^3$ (equivalent to 100,000 Floppy Disks®). Since the three-dimensional optical recording medium of the present invention has such a large recording capacity, it can be expected to become the next-generation memory medium.

In addition, as described above, the use of the compounds according to the present invention is not limited to the three-dimensional optical recording materials and three-dimensional optical recording media. That is, the compounds of the present invention can be used for any applications. For instance, the compounds of the present invention also can be used for two-dimensional optical recording materials or two-dimensional optical recording media as described above. Moreover, the compounds of the present invention can be used, as pigments, for applications other than optical recording materials.

EXAMPLES

Next, examples of the present invention are described. However, the present invention is not limited to the following examples.

In the following examples, the nuclear magnetic resonance (NMR) spectra were measured using an apparatus JNM EX270 (trade name) manufactured by JEOL Ltd. (270 MHz during $^1$H measurement), an apparatus JNM EPC500 (trade name) manufactured by JEOL Ltd. (500 MHz during $^1$H measurement), or an apparatus JNM EPC600 (trade name) manufactured by JEOL Ltd. (600 MHz during $^1$H measurement). The chemical shift is indicated by part per million (ppm). For the internal standard, 0 ppm, tetramethylsilane (TMS) was used. The coupling constant (J) is indicated in hertz. Abbreviations s, d, t, q, m, and br denote singlet, doublet, triplet, quartet, multiplet, and broad, respectively. The mass spectrometric analysis (MS, Mass) was carried out by the MALDI-TOF method using an apparatus Voyager DE-STR or AXIMA-LNR (trade name) manufactured by PerSeptive Biosystems or Shimadzu Corporation (Shimadzu/KRATOS). The visible/ultraviolet absorption spectrum was measured using an apparatus UV-3100PC (trade name) or UV-1650PC (trade name) manufactured by Shimadzu Corporation. An apparatus Surelight I-10(trade name) manufactured by Continuum was used in combination with Continuum Surelight OPO (trade name) for laser irradiation. The fluorescence spectrum was measured using an apparatus F-4500 (trade name) manufactured by Hitachi, Ltd. All chemical substances were of reagent grade and were purchased from Wako Pure Chemical Industries, Ltd. or NACALAI TESQUE, INC.

Example 1

Production of porphyrin Compounds (2) and (3)

According to Scheme 3, porphyrin compounds represented by the formulae (2) and (3) were synthesized (produced). The details are described below.
1) Synthesis of Raw Materials The compound (4) that was a starting material used in Scheme 3 was synthesized according to the description in a reference, K. Ogawa, J. Dy, and Y. Kobuke, Journal of Porphyrins and Phthalocyanine 9, 735-744 (2005). The details are described below. First, dipyrromethane (167.4 mg, 1.14 mmol), 4-ethoxycarbonylbenzaldehyde (204 mg, 1.14 mmol), and chloroform (200 mL) were placed in a 500-mL three neck flask. Then nitrogen gas bubbling was carried out therein for three minutes and thereby a nitrogen gas atmosphere was obtained. Thereafter, trifluoroacetic acid (88.2 μL, 1.14 mmol) was added thereto. This was stirred at room temperature under a light-shielded condition for 20 hours. Then triethylamine (0.5 mL, 3.56 mmol) and chloranil (884 mg, 3.4 mmol) were added thereto and this was refluxed at 70° C. for 1.5 hours. Then the solvent was distilled away and purification was carried out by silica gel column chromatography (solvent:chloroform). Thus the compound (4) was obtained as a purplish-red solid (141.1 mg, 40.9%). The instrumental analysis data of the compound (4) is indicated below.
Compound (4):
$^1$H-NMR (270 MHz, CDCl$_3$) δ 10.332 (s, 2H, meso), 9.405 (d, 4H, J=4.7 Hz, β), 9.033 (d, 4H, J=4.7 Hz, B), 8.490 (d, 4H, J=8.1 Hz, Ph), 8.351 (d, 4H, J=8.1 Hz, ph), 4.607 (q, 4H, J=3.5 Hz, —CH$_2$—), 1.342 (t, 6H, J=3.5 Hz, —CH$_3$), MALDI-TOF mass (matrix:dithranol), m/z 606.90, calcd for C$_{38}$H$_{30}$N$_4$O$_4$ 606.23.

A starting material of the compound (4), 4-ethoxycarbonylbenzaldehyde, was synthesized according to the description in the reference, K. Ogawa, J. Dy, and Y. Kobuke, Journal of Porphyrins and Phthalocyanine 9, 735-744 (2005). The details are described below. First, terephthalaldehydic acid (5.5 g, 36.6 mmol), strong sulfuric acid (0.91 mL), and ethanol (166.6 mL) were added to a 300-mL recovery flask and then were heated to be refluxed for 18 hours. Then this was returned to room temperature and then the organic solvent was distilled away. Thereafter, this was dissolved in ethyl acetate (100 mL). Then it was washed with saturated sodium bicarbonate (200 mL×2), a saturated saline solution (200 mL×2), and distilled water (200 mL×2), and then was dried with anhydrous sodium sulfate. Thus enrichment and drying were carried out (5.42 g, 83.1%). The instrumental analysis data of this product is indicated below.
4-ethoxycarbonylbenzaldehyde
$^1$H-NMR (270 MHz, CDCl$_3$), δ 10.10 (s, 1H, —CHO), 8.15 (d, 2H, J=8.1 Hz), 7.94 (d, 2 h, J=8.1 Hz), 4.42 (q, 2H, J=3.5 Hz, —CH$_2$—), 1.42 (t, 2H, J=3.5 Hz, —CH$_3$)

A starting material of the compound (4), dipyrromethane, was synthesized according to the description in the reference, J. K. Laha, S. Dhanalekshmi, M. Taniguchi, A. Ambroise and J. S. Lindsey, Org. Process Res. Dev. 2003; 7: 799-812. The details are described below. First, pyrrole (120 mL, 1.71 mol), paraformaldehyde (1.21 g, 40 mmol) that had been ground well in a mortar, methanol (60.7 mL), and acetic acid (158.8 mL) were added to a 1000-mL recovery flask in this order. Then nitrogen gas bubbling was carried out in the recovery flask for ten minutes. This was stirred in a nitrogen gas atmosphere at room temperature for 24 hours. Thereafter, this was diluted with chloroform (50 mL) and then was neutralized with a saturated sodium bicarbonate aqueous solution. Further, this was extracted with chloroform (50 mL). This was dried with anhydrous sodium sulfate and an organic layer was distilled away. Then distillation was carried out to recover pyrrole (30° C., 7.3 kpa) and thereafter, dipyrromethane (120° C., 0.1 kpa) was obtained. This was purified by silica gel column chromatography (solvent:chloroform:hexane: ethyl acetate=7:2:1) and thereby white crystals (1.36 g, 25.6%) were obtained. The instrumental analysis data of this product is indicated below.
Dipyrromethane:
$^1$H-NMR (270 MHz, CDCl$_3$) δ 7.78 (brs, 2H, NH), 6.62 (m, 2H), 6.14 (dd, 2H, J=2.7, 5.9 Hz), 6.03 (m, 2H), 3.95 (s, 2H, meso).

A compound (6) that was a starting material was synthesized according to a reference, J. Leavitt, Chemical Abstract, 1971, 74, 113187n. The details are described below. First, 7-iodo-benzo-thiochromen-3-one (650 mg, 275 mmol, 1.0 eq) and EtOH (103 mL) were added to a 500-mL three neck flask. This was sonicated for one minute to be brought into a suspended state. Then a 10% NaOH solution (168 mL, 288 mol) was added thereto. This was refluxed at 70° C. for eight hours while being subjected to air bubbling. Then filtration was carried out to separate a solid. This was washed with methanol and chloroform. Thus a blue solid (243.3 mg, 75.3%) was obtained. This solid was insoluble in various solvents (chloroform, methanol, ethanol, ethyl acetate, acetone, benzene, pyridine, hexane, and toluene). The solid was dissolved slightly in THF but the measurement of NMR was not possible. The instrumental analysis data of the solid (compound (6)) is indicated below.
Compound (6):
MALDI-TOF mass (matrix:dithranol), m/z 648.777 [as M+H], calcd for C$_{38}$H$_{30}$N$_4$O$_4$ 647.8 [as M]

A starting material of the compound (6), 7-iodo-benzothiochromen-3-one, was synthesized according to a reference, J. Leavitt, Chemical Abstract, 1971, 74, 113187n. The details are described below. First, 3-methoxycarbonyl-7-iodo-benzothiochromen (700 mg, 1.9 mmol) and acetic acid (82 mL) were added to a 200-mL recovery flask. This was sonicated for one minute to be brought into a suspended state. Then 35% acetic acid (11.1 mL, 95 mmol) was added thereto and nitrogen gas babbling was carried out therein for two minutes. This was heated and stirred in a nitrogen gas atmosphere at 40° C. for 4.5 hours. Ice was placed in a 300-mL Erlenmeyer flask and then the reaction solution was placed therein to be cooled. As a result, a brownish yellow precipitate was deposited. Then filtration was carried out to separate the precipitate. This was dissolved in chloroform (100 mL). Then this was washed with a saturated sodium bicarbonate aqueous solution (200 mL×2) and water (200 mL×2). Thereafter, it was dried with anhydrous sodium sulfate, and an organic layer was removed. Then enrichment and drying were carried out. Thus a brown solid (666 mg, 98%) was obtained. The instrumental analysis data of the solid is indicated below.

7-iodo-benzo-thiochromen-3-one $^1$H-NMR (270 MHz, CDCl$_3$) δ 8.397 (dd, 1H, J=1.1, 8.6 Hz), 8.251 (dd, 1H, J=1.1 7.3 Hz), 8.003 (d, 1H, J=8.6), 7.682 (dd, 1H, J=7.3 Hz), 7.298 (d, 1H, J=7.3 Hz)

Furthermore, a starting material of 7-iodo-benzo-thiochromen-3-one, 3-methoxycarbonyl-7-iodo-benzothiochromen, was synthesized according to the reference, J. Leavitt, Chemical Abstract, 1971, 74, 113187n. The details are described below. First, 8-carboxymethylsulfenyl-5-iodo-naphthalene-1-carboxylic acid (370 mg, 0.95 mmol), sodium acetate (100 mg, 1.2 mmol), and acetic anhydride (20 mL) were placed in a 100-mL recovery flask. This was heated and refluxed at 140° C. for two hours. It was cooled and then chloroform (100 mL) was added thereto. This was neutralized by gradually adding a saturated sodium bicarbonate aqueous solution thereto. Then this was washed with a saturated sodium bicarbonate aqueous solution (200 mL×2) and water (200 mL×2). Thereafter, it was dried with anhydrous sodium sulfate, and an organic layer was removed. Then drying and enrichment were carried out. Thus a brown solid (349 mg, 99.9%) was obtained. The instrumental analysis data of the solid is indicated below.

3-methoxycarbonyl-7-iodo-benzothiochromen

Melting point 114.2-115.7° C. (reference value: 112.5-113° C.), $^1$H-NMR (270 MHz, CDCl$_3$) δ 7.744 (d, 1H, J=8.1 Hz), 7.727 (d, 1H, J=7.6 Hz), 7.303 (t, 1H, J=7.6 Hz), 6.942 (d, 1H, J=7.6 Hz), 6.795 (d, 1H, J=8.1 Hz), 2.342 (s, 3H)

Furthermore, a starting material of 3-methoxycarbonyl-7-iodo-benzothiochromen, 8-carboxymethylsulfenyl-5-iodo-naphthalene-1-carboxylic acid, was synthesized according to a reference, Chemical Abstract, 1969, 70, 3615k. The details are described below. First, 6-iodonaptho[1,8-bc]thiophen-2-one (242 mg, 0.68 mmol, 1.0 eq) and 5% NaOH (11 mL) were placed in a 50-mL recovery flask. This was heated and stirred at 80° C. for one hour. Thereafter, chloroacetic acid (200 mg, 2.1 mmol, 3.9 eq) was added thereto. This further was heated and stirred at 80° C. for one hour. Then the generation of an intended product was confirmed by TLC. It was cooled to room temperature and then hydrochloric acid was added thereto until the pH thereof became 1. As a result, a yellow precipitate was generated. Then the precipitate was separated by filtration. The solid thus obtained was washed with chloroform and then was dried. Thus a yellow solid (298 mg, 98.2%) was obtained. The instrumental analysis data of this solid is indicated below.

8-carboxymethylsulfenyl-5-iodo-naphthalene-1-carboxylic acid $^1$H-NMR (270 MHz, CDCl$_3$) δ 8.182 (d, 1H, J=8.1 Hz), 8.174 (d, 1H, J=8.1 Hz), 7.726 (d, 1H, J=7.3 Hz), 7.670 (t, 1H, J=7.3, 8.1 Hz), 7.583 (d, 1H, J=8.1 Hz), 3.661 (s, 2H)

A starting material of 8-carboxymethylsulfenyl-5-iodo-naphthalene-1-carboxylic acid, 6-iodonaptho[1,8-bc]thiophen-2-one, was synthesized according to a reference, Chemical Abstract, 1969, 70, 3615k. The details are described below. First, naphtho[1,8-bc]thiophen-2-one (0.7 g, 375 mmol), acetic acid (10 mL), and ICl (5.5 g, 34 mmol) were placed in a 50-mL recovery flask and were refluxed for three hours. Thereafter, water (60 mL) was added thereto and then a saturated sodium thiosulfate aqueous solution was added thereto. As a result, a yellow-green precipitate was deposited. The precipitate was separated by filtration and then was dissolved in chloroform (100 mL). This was washed with a saturated sodium thiosulfate aqueous solution (200 mL×2) and water (200 mL×2), and then was dried with anhydrous sodium sulfate. Then enrichment and drying were carried out, and then recrystallization was performed with ethanol. Thus a yellow solid (226 mg, 51.8%) was obtained. The instrumental analysis data of the solid is indicated below.

6-iodonaptho[1,8-bc]thiophen-2-one $^1$H-NMR (270 MHz, CDCl$_3$) δ 8.240 (d, 1H, J=8.1 Hz), 8.212 (d, 1H, J=7.3 Hz), 8.128 (d, 1H, J=7.3 Hz), 7.845 (dd, 1H, J=8.1 Hz), 7.344 (d, 1H, J=7.3 Hz)

A starting material of 6-iodonaptho[1,8-bc]thiophen-2-one, naphtho[1,8-bc]thiophen-2-one, was synthesized according to a reference, Synthesis, 1989, 7, 523. The details are described below. First, 8-iodo-1-naphthoic acid (2.8 g, 9.39 mmol) was added to 7N KOH (7.1 mL). This was stirred until 8-Iodo-1-naphthoic acid was dissolved. Then mercaptopropionic acid (2.5 mL, 23.3 mmol) and powdered Cu (94 mg, 1.48 mmol) were mixed into the solution. After nitrogen gas bubbling was carried out therein for about one minute, it was refluxed in an argon atmosphere for five hours. Then 7N KOH (2 mL) further was added thereto and then it was refluxed for two hours. Water (4.9 mL) was added thereto and filtration was carried out. Then 6N HCl (2.1 mL) was added to the filtrate to allow the reaction system to be acid (pH 1). As a result, a yellow precipitate was deposited. The precipitate was separated by filtration and was dissolved in chloroform (100 mL). This was washed with a saturated sodium bicarbonate aqueous solution (200 mL×2) and water (200 mL×2) and then was dried with anhydrous sodium sulfate. Then enrichment and drying were carried out. Thus a yellow solid (1.76 g, 99%) was obtained. The instrumental analysis data of the solid is indicated below.

Naphtho[1,8-bc]thiophen-2-one $^1$H-NMR (270 MHz, CDCl$_3$) δ 8.188 (d, 1H, J=7.3 Hz), 8.160 (d, 1H, J=8.1 Hz), 7.852 (dd, 1H, J=3.8, 4.6 Hz), 7.784 (dd, 1H, J=4.6, 7.3 Hz), 7.635 (d, 1H, J=3.8 Hz), 7.629 (d, 1H, J=7.3 Hz)

A starting material of naphtho[1,8-bc]thiophen-2-one, 8-iodo-1-naphthoic acid, was synthesized according to a reference, Baily, R. J.; Card, P. J.; Shechter, H.; J. Am. Chem. Soc. 1983, 105, 6096-6103. The details are described below. First, I2 (12.0 g, 47.6 mmol) and anhydro-8-(hydroxymercuri)-1-naphthoic acid (17.0 g, 45.9 mmol) were added to a KI aqueous solution (32.4 g/162 mL). The mixture was refluxed for 15 hours. Then it was cooled and filtrated. Hydrochloric acid was added to the filtrate to allow it to be acid (pH 1). As a result, a milky yellow precipitate was obtained. Then the precipitate was separated by filtration and was dissolved in chloroform (100 mL). This was washed with a saturated sodium thiosulfate aqueous solution (200 mL×2) and water (200 mL×2), and then was dried with anhydrous sodium sulfate. Then the light yellow organic layers were collected and enrichment and drying were carried out. Thus a yellow solid (5.70 g, 42.2%) was obtained. The instrumental analysis data of this solid is indicated below.
8-Iodo-1-naphthoic acid $^1$H-NMR (270 MHz, CDCl$_3$) δ 8.271 (dd, 1H, J=7.6, 8.1 Hz), 7.915 (m, 3H), 7.6 (dd, 1H, J=7.6, 8.1 Hz), 7.222 (dd, 1H, J=7.6, 8.1 Hz)

A starting material of 8-iodo-1-naphthoic acid, anhydro-8-(hydroxymercuri)-1-naphthoic acid, was synthesized according to the reference, Baily, R. J.; Card, P. J.; Shechter, H.; J. Am. Chem. Soc. 1983, 105, 6096-6103. The details are described below. First, commercial 1,8-naphthalic anhydride (0.991 g, 5 mmol) and a sodium hydroxide aqueous solution (0.7 g/30 mL, 17.5 mmol) were added to a 200-mL recovery flask. This was stirred and was refluxed until the solid was dissolved (one hour). This was neutralized with acetic acid (0.5 mL, 8.3 mmol). Then a mercuric acetate solution was added thereto that was obtained by dissolving mercuric oxide (1.1 g, 5.1 mmol) in boiling acetic acid (2.5 mL, 41.5 mmol) and diluting it with 18 mL of water. This was refluxed for 30 minutes and then acetic acid (0.9 mL, 14.9 mmol) was added thereto. This was refluxed for 48 hours. A precipitate thus generated was separated by filtration and then was washed with methanol and water. This was dried in vacuum at 105° C. for 15 hours. Thus yellowish brown powder (1.363 g, 74.0%) was obtained. Since this powder was insoluble in water and organic solvents, it was not analyzed but was used for the next reaction (the synthesis of 8-Iodo-1-naphthoic acid). The aforementioned reference also does not indicate any instrumental analysis data of anhydro-8-(hydroxymercuri)-1-naphthoic acid.

2) Step 1
Synthesis of Compound (5)

Step 1 (synthesis of the compound (5)) in Scheme 3 was carried out as follows. First, the compound (4) (32.0 mg, 41.8 μmol, 1.0 eq) and chloroform (10 mL) were placed in a 100-mL recovery flask. Then tetrabutylammonium fluoride (1M in THF) (144 μL, 144 μmol, 3.45 eq) was added to the solution. This was stirred at room temperature for ten minutes. Thereafter, the disappearance of raw materials from the solution was confirmed by TLC and mass spectrum. Subsequently, chloroform (10 mL) was added to the solution. This was washed with a saturated sodium bicarbonate aqueous solution (50 mL×2) and water (50 mL×2) and then an organic layer was separated to be removed. This was dried with sodium sulfate and then enrichment and drying (distillation of the solvent) were carried out. The residue thus obtained was purified by silica gel column chromatography (solvent:Hex/AcOH=4/1). Thus an intended compound (5) was obtained as a purple solid. The yield amount was 20.7 mg and the yield ratio was 73.0%. The instrumental analysis data of this compound (5) is indicated below. In the $^1$H-NMR data of the compound (5) described below, the marks "a", "b", "c", "d", "e", "f", and "β" indicate positions of carbon atoms to which the respective protons (H) were bonded. The positions in the compound (5) of those respective carbon atoms are indicated with corresponding marks in the following chemical formula.
Compound (5):

TLC (CHCl$_3$) Rf=0.12; $^1$H-NMR (270 MHz, CDCl$_3$), δ 10.204 (s, 1H, f), 9.800 (d, 2H, J=2.16, B), 9.339 (d, 2H, J=2.16, β), 8.993 (d, 2H, J=2.16, β), 8.953 (d, 2H, J=2.16, B), 8.442 (d, 4H, J=3.78, e), 8.283 (d, 4H, J=3.78, d), 4.565 (q, 4H, J=3.24, c), 3.476 (s, 1H, a), 1.560(t, 6H, J=3.24, b); MALDI-TOF mass (dithranol), m/z 693.44 (M+H)$^+$, calcd for C$_{38}$H$_{30}$N$_4$O$_4$ 692.1

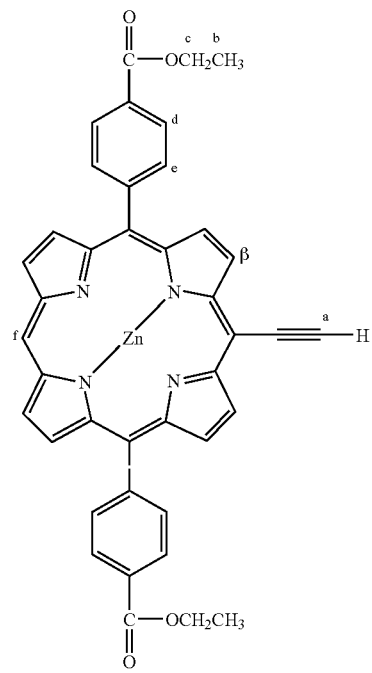

(5)

3) Step 2
Synthesis of Compounds (2) and (3)

Step 2 in Scheme 3 was carried out as follows. First, the inside of a 100-mL Schlenk flask was allowed to be an Ar atmosphere. Then the compound (6) (1.9 mg, 2.9 μmol, 4 eq) and dry THF (9 mL) were added thereinto. This was sonicated for five minutes to be brought into a suspended state. Thereafter, triethylamine (1 mL) and the compound (5) (0.5 mg, 1.4 μmol, 1 eq) were added to the suspension. This was subjected to Ar bubbling for 10 minutes to be deoxidized. Subsequently, Pd$_2$(dba)$_3$ (0.2 mg, 0.27 μmol, 0.12 eq) and AsPh$_3$ (0.6 mg, 1.8 μmol, 0.8 eq) were added thereto (dba=dibenzylideneacetone). This was stirred at room temperature under a light-shielded condition. The reaction was traced by MALDI-TOF mass spectrum. Disappearance of the raw material (5) and generation of the compounds (2) and (3) were confirmed four hours after the start of the reaction. Then the reaction was stopped. Thereafter, water (20 mL) was added to quench it and the solvent was distilled away. Chroloform (10 mL) was added to the residue thus obtained. This was washed with a saturated ammonium chloride aqueous solution (50 mL×2) and water (50 mL×2) and then the organic layer was separated to be removed. This was dried with anhydrous sodium sulfate and further enrichment and drying were carried out. The residue thus obtained was purified by GPC for recycle separation (solvent:pyridine). Thus intended porphyrin compounds (2) and (3) were obtained. For the GPC for recycle separation, LC-9101 (trade name) manufactured by Japan Analytical Industry Co., Ltd. was used. The retention time Rt of the compound (2) was 25 minutes, while that of the compound (3) was 26 minutes. The compound (2) thus obtained was a dark green solid and had a yield ratio of 20% and a yield amount of 0.2 mg. The compound (3) thus obtained was a dark green solid and had a yield ratio of 40% and a yield amount of 0.3 mg. The instrumental analysis data of the intended compounds (2) and (3) is indicated below. In the $^1$H-NMR data of the compounds (2) and (3) described below, the marks "a", "b", "c", "d", "e", and "B" indicate positions of carbon atoms to which the respective protons (H) were bonded. The positions in the compounds (2) and (3) of those respective carbon atoms are indicated with corresponding marks in the following chemical formulae. Furthermore, in the $^1$H-NMR data described below, "PNI" denotes a proton signal of a perinaphthothioindigo ring. The perinaphthothioindigo rings in the compounds (2) and (3) are indicated with a mark "PNI" in the chemical formulae below.

Compound (3):

$^1$H-NMR (500 MHz, tetrachloroethane-d$_2$/Pyridine-d$_5$), δ 10.07 (s, 1H, a), 9.81 (d, J=4.5 Hz, 2H, B), 9.31 (d, J=8 Hz, 1H, PNI), 9.23 (d, J=4.5 Hz, 2H, β), 8.92 (d, J=4.5 Hz, 2H, β), 8.83 (d, J=4.5 Hz, 2H, β), 8.69 (d, J=8 Hz, 1H, PNI), 8.54 (d, J=8 Hz, 1H, PNI), 8.37 (d, J=8 Hz, 4H, e), 8.24 (d, J=8 Hz, 4H, d), 8.20 (d, J=8 Hz, 1H, PNI), 8.08 (d, J=8 Hz, 1H, PNI), 7.98 (t, J=8 Hz, 1H, PNI), 7.77 (d, J=8 Hz, 1H, PNI), 7.70 (d, J=8 Hz, 1H, PNI), 7.68 (t, J=8 Hz, 1H, PNI), 7.62 (PNI, overlaps with pyridine peak), 7.46 (t, J=8 Hz, 1H, PNI), 4.49(q, J=7.5 Hz, 4H, c), 1.48 (t, J=7.5 Hz, 6H, b); MALDI-TOF mass (dithranol), m/z 1086.5(M+H)$^+$, calcd for C$_{64}$H$_{38}$N$_4$O$_6$S$_2$Zn 1086.2

Compound (2):

$^1$H-NMR (600 MHz, tetrachloroethane-d$_2$), δ 10.14 (s, 2H, a), 9.80 (br, 2H, β), 9.29 (d, J=8 Hz, 2H, PNI), 9.29 (br, 2H, β), 8.90 (br, 2H, β), 8.83 (br, 2H, β), 8.70 (d, J=8 Hz, 2H, PNI), 8.37 (d, J=8 Hz, 8H, e), 8.24 (d, J=8 Hz, 8H, d), 8.20 (d, J=8 Hz, 2H, PNI), 7.98 (br, 2H, PNI), 7.73 (d, J=8 Hz, 2H, PNI), 4.59 (q, J=7.5 Hz, 8H, c), 1.48 (t, J=7.5 Hz, 12H, b); MALDI-TOF mass (dithranol), m/z 1781.8(M+H)$^+$, calcd for C$_{104}$H$_{64}$N$_8$O$_{10}$S$_2$Zn$_2$ 1780.2

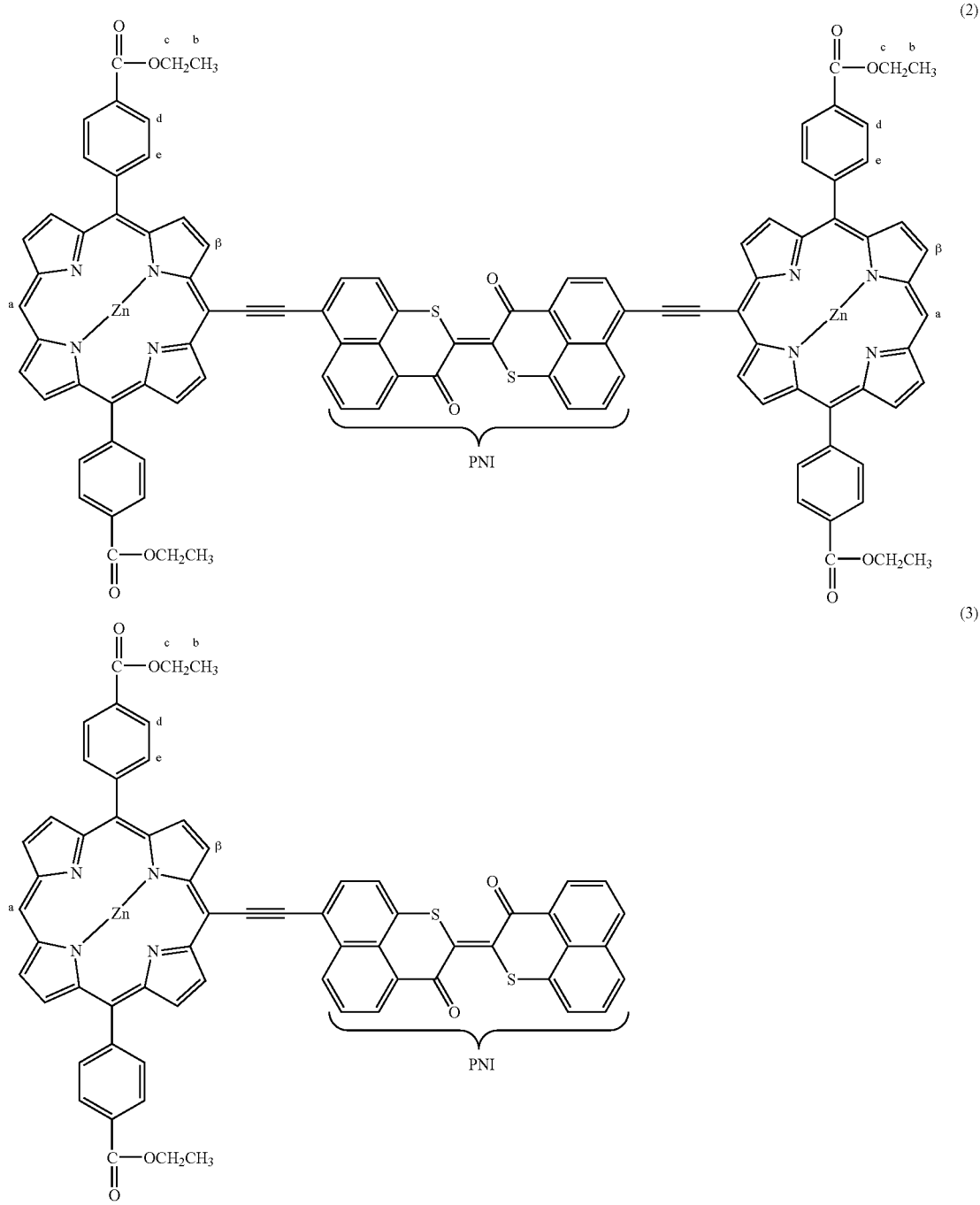

Example 2

Production of cis porphyrin Compound (3')

FIG. 1 shows a visible/ultraviolet absorption spectrum of a porphyrin compound (3) that is a new photochromic molecule obtained in Example 1. In FIG. 1, the vertical axis indicates the absorbance, while the horizontal axis indicates the wavelength. This spectrum was measured using a 2.2-μM concentration solution obtained by dissolving the compound (3) in tetrahydrofuran (THF). As shown in FIG. 1, absorption in the Soret band that is peculiar to porphyrin is observed around 440 nm. On the other hand, absorption that originates from the trans configuration of a perinaphthothioindigo site is observed from 650 nm to 750 nm.

As shown in Scheme 4 below, the photoisomerization (photochromism) property of the compound (3) was confirmed. The compound (3') was produced though this isomerization.

Scheme 4

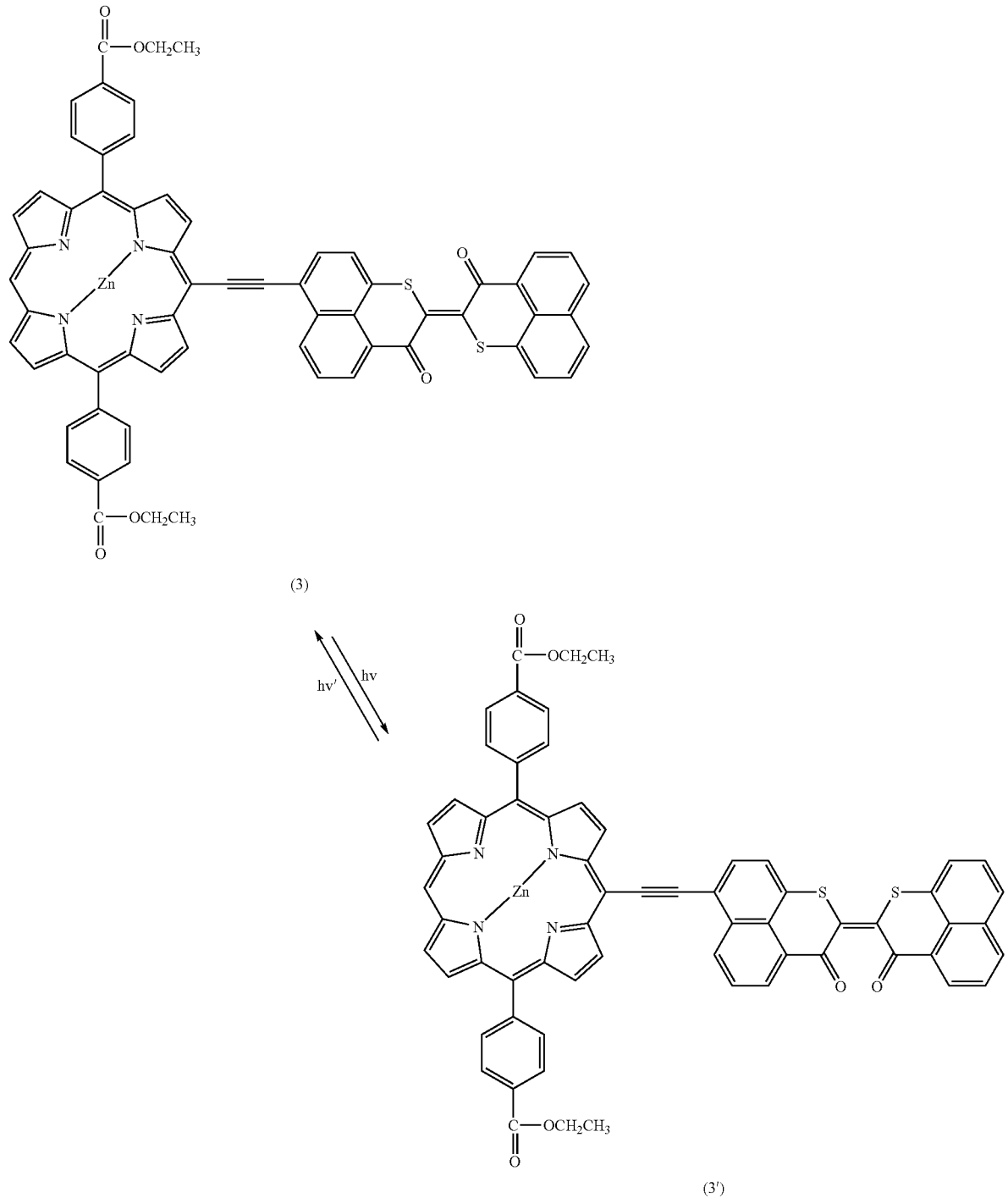

As shown in Scheme 4 above, the compound (3) is a porphyrin compound with a perinaphthothioindigo site having a trans configuration (hereinafter may be referred to as a "trans porphyrin compound" or simply as a "trans form"). This compound (3) was irradiated with light and thereby was allowed to undergo photochromism. Thus a porphyrin compound with a perinaphthothioindigo site having a cis configuration (hereinafter may be referred to as a "cis porphyrin compound" or simply as a "cis form") (3') was produced. Furthermore, the cis porphyrin compound (3') was irradiated with light and thereby it was confirmed that it was reverted to the trans porphyrin compound (3) through photochromism. The details are described below.

Figure 2:
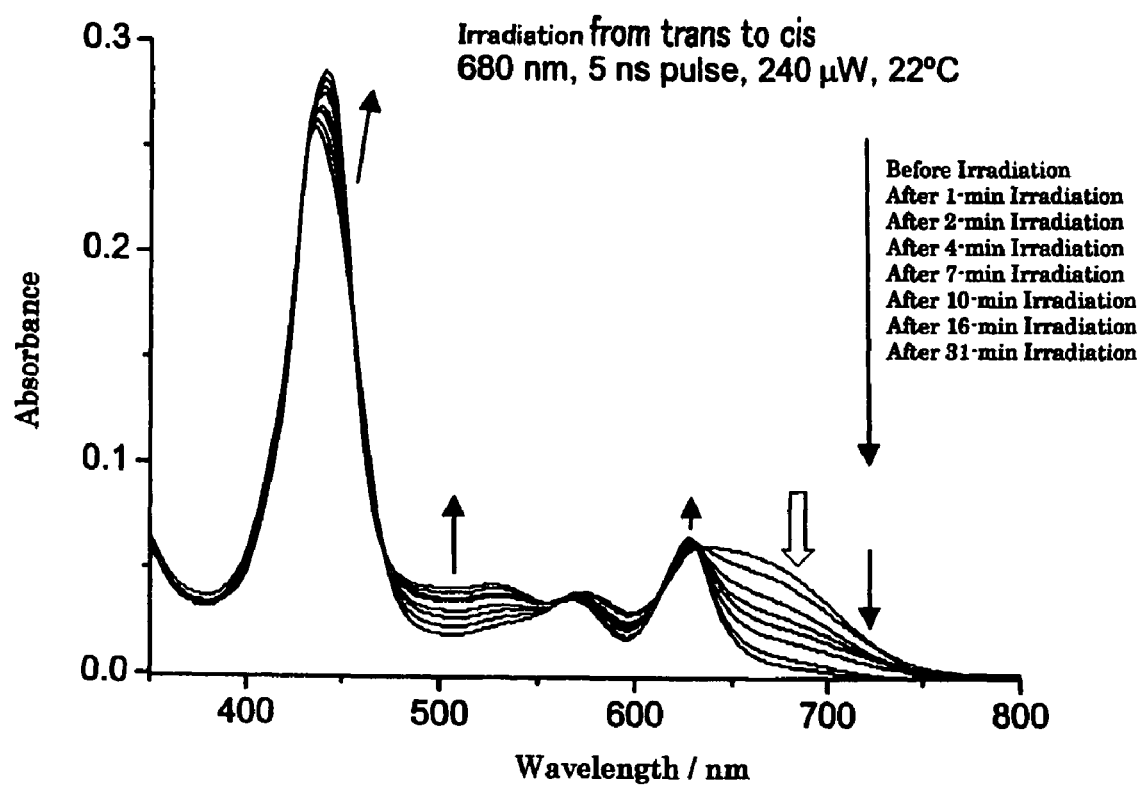
FIG. 2 is a graph showing the change in visible/ultraviolet absorption spectrum that is caused when the compound (3) of the example is allowed to undergo a photoisomerization reaction from a trans form to a cis form at room temperature (in the THF solution).

That is, first, a trans porphyrin compound (3) synthesized in Example 1 was dissolved in tetrahydrofuran (THF) and thereby a 2.2 μM solution was prepared. This solution was subjected to laser irradiation at room temperature (22° C.), and thereby the perinaphthothioindigo site of the compound (3) was excited. The change with time in visible/ultraviolet absorption spectrum of the compound (3) was measured. The irradiation wavelength was 680 nm, the laser beam used herein was a Nd:YAG-OPO laser with a pulse width of 5 ns, and the average power was 240 μW. The change with time in the visible/ultraviolet absorption spectrum is shown in the graph in FIG. 2. In FIG. 2, the vertical axis indicates the absorbance, while the horizontal axis indicates the wavelength. The spectra are those obtained before the laser beam irradiation and 1, 2, 4, 7, 10, 16, and 31 minutes after the start of irradiation. In FIG. 2, the outline arrow (⇒) indicates the position of 680 nm that is a wavelength of the irradiated laser beam. The black arrows (→) attached to the respective absorption bands each denote an increase or decrease in absorption accompanying the laser beam irradiation in the respective absorption bands. As shown in FIG. 2, the absorption in the range of 650 nm to 750 nm that originates from the perinaphthothioindigo site of the trans form (3) decreased with light irradiation. At the same time, the absorption in the range of 480 nm to 550 nm that originates from the perinaphthothioindigo site of the cis form (3') increased. The change in spectrum almost stopped after 31 minutes of irradiation and the trans form was changed to the cis form (3') completely. A solution of this cis form (3') was allowed to stand still under a light-shielded condition at room temperature (22° C.) for 12 hours, and the spectrum was measured. The result of the spectrum measurement coincided with the spectrum obtained after 31 minutes of irradiation. This result indicates that the state of the cis form (3') was maintained even after the solution subjected to irradiation for 31 minutes was allowed to stand still for 12 hours. As described above, the trans porphyrin compound (3) was irradiated with a laser beam to be isomerized and thereby the cis porphyrin compound (3') was produced.

Figure 3:
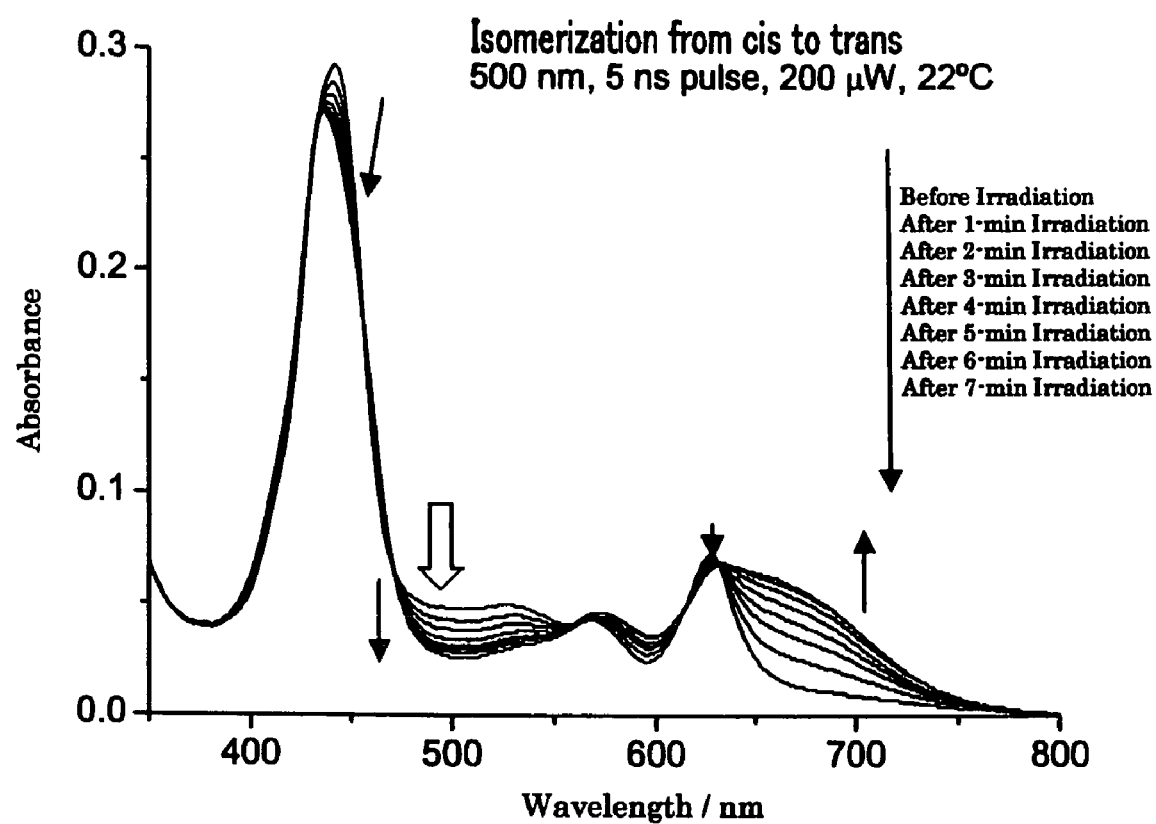
FIG. 3 shows the change in visible/ultraviolet absorption spectrum that is caused when the compound (3') of the example is allowed to undergo a photoisomerization reaction from a cis form to a trans form at room temperature (in the THF solution).

Furthermore, this cis form (3') solution was irradiated with a laser beam at room temperature (22° C.), and thereby the perinaphthothioindigo site of the cis form (3') was excited. Then the change with time in the visible/ultraviolet absorption spectrum of the compound (3') was measured. The irradiation wavelength was 500 nm, the laser beam used herein was a Nd:YAG-OPO laser with a pulse width of 5 ns, and the average power was 200 μW. The change with time in the visible/ultraviolet absorption spectrum is shown in the graph in FIG. 3. In FIG. 3, the vertical axis indicates the absorbance, while the horizontal axis indicates the wavelength. The spectra are those obtained before the irradiation and 1, 2, 3, 4, 5, 6, and 7 minutes after the start of irradiation. In FIG. 3, the outline arrow (⇒) indicates the position of 500 nm that is a wavelength of the irradiated laser beam. The black arrows (→) attached to the respective absorption bands each denote an increase or decrease in absorption accompanying the laser beam irradiation in the respective absorption bands. As shown in FIG. 3, the absorption in the range of 650 nm to 750 nm that originates from the perinaphthothioindigo site of the trans form (3) increased with light irradiation. At the same time, the absorption in the range of 480 nm to 550 nm that originates from the perinaphthothioindigo site of the cis form (3') decreased. The change in spectrum almost stopped after 7 minutes of irradiation and a photostationary state was obtained.

As described above, the trans porphyrin compound (3) was isomerized and thereby the cis porphyrin compound (3') was produced. At the same time, the photochromism of the trans form (3) and the cis form (3') also was confirmed.

Example 3

Production of cis porphyrin Compound (2')

Figure 9:
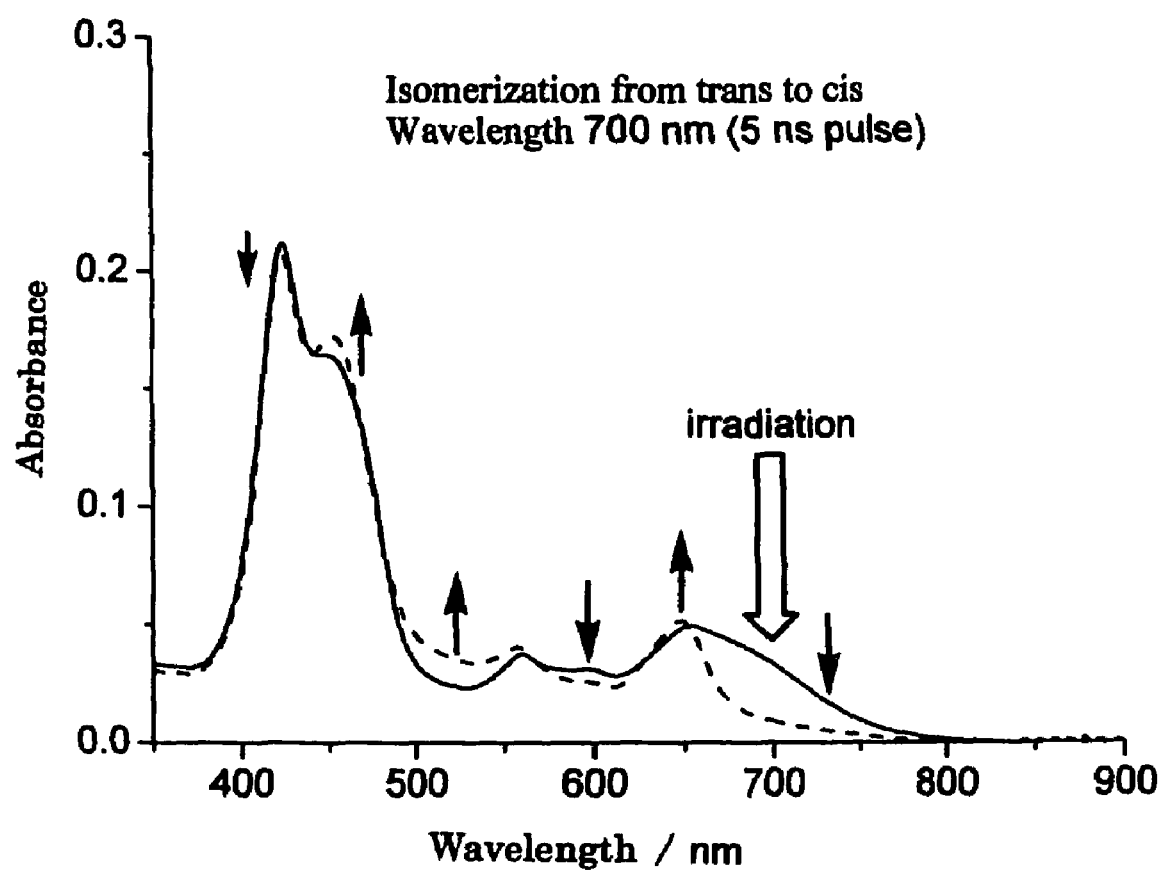
FIG. 9 is a graph showing the change in visible/ultraviolet absorption spectrum that is caused when the compound (2) of the example undergoes a photoisomerization reaction from a trans form to a cis form (in the THF solution).

FIG. 9 shows a visible/ultraviolet absorption spectrum of a porphyrin compound (2) that is a new photochromic molecule obtained in Example 1. In FIG. 9, the vertical axis indicates the absorbance, while the horizontal axis indicates the wavelength. In FIG. 9, the solid curved line indicates the spectrum of the porphyrin compound (2). This spectrum was measured in the same manner as in Example 2 using a 1.8 μM concentration solution obtained by dissolving the compound (2) in tetrahydrofuran (THF). As shown in FIG. 9, absorption in the Soret band that is peculiar to porphyrin is observed around 420 nm to 460 nm, while absorption that originates from the trans perinaphthothioindigo site is observed from 650 nm to 750 nm.

As shown in Scheme 5 below, the photoisomerization (photochromism) property of the compound (2) was confirmed. The compound (2') was produced though this isomerization.

Scheme 5

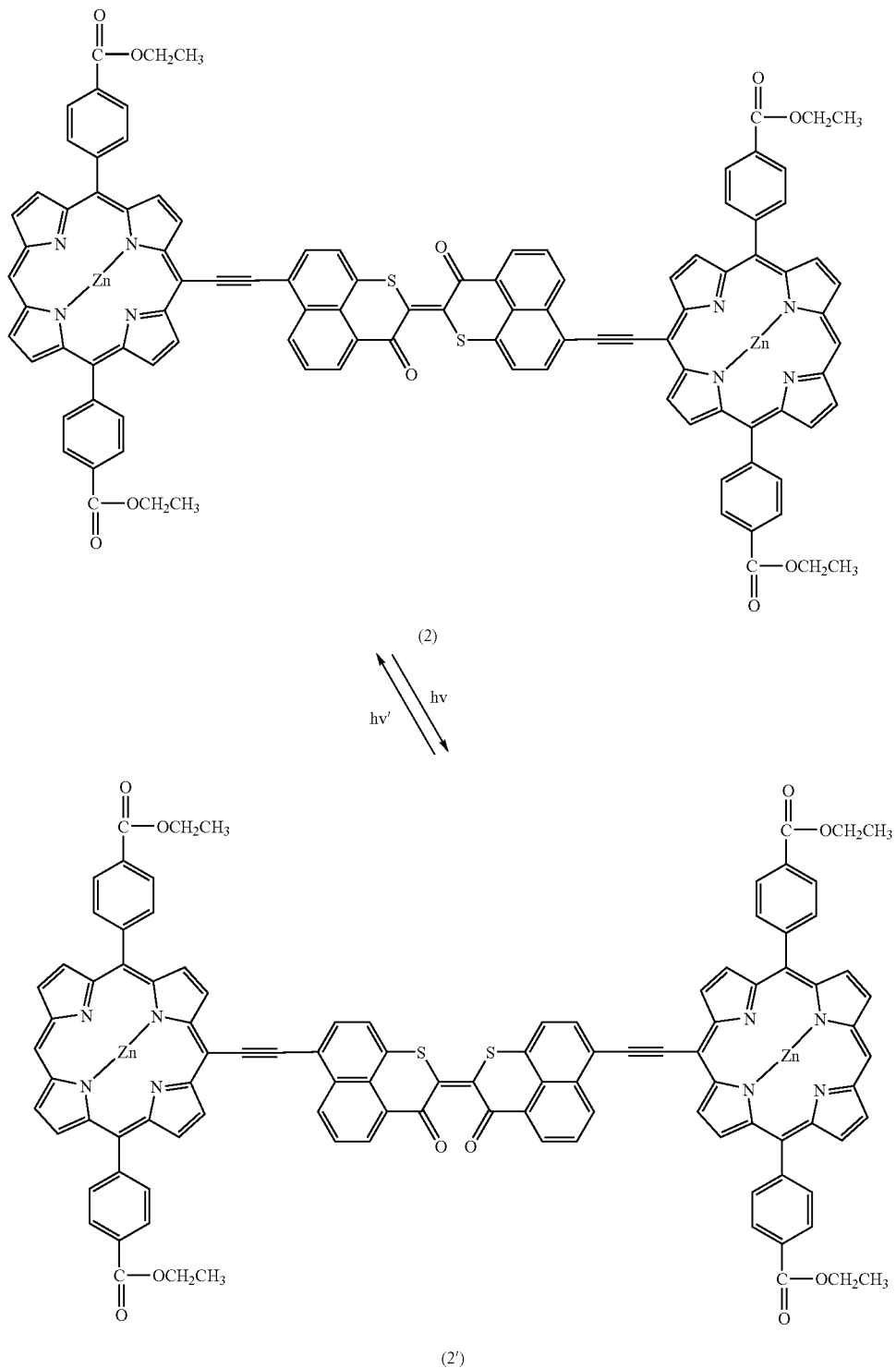

(2)

⇅ hv / hv'

(2')

A solution of the trans porphyrin compound (2) was irradiated with a laser beam at room temperature (25° C.). For the light source, a Nd:YAG-OPO laser with a pulse width of 5 ns and an irradiation wavelength of 700 nm was used. The average power was 30 mW and the irradiation time was one minute. With this laser beam irradiation, the perinaphthothio- indigo site of the trans porphyrin compound (2) was excited. In FIG. 9, the visible/ultraviolet absorption spectrum of the solution that has been excited is shown with a broken line. The black arrows shown in FIG. 9 each denote a decrease or an increase in absorption accompanying the beam irradiation (excitation). As shown in FIG. 9, the absorption in the range of 650 nm to 750 nm that originates from the perinaphthothioindigo site of the trans form (2) decreased after the excitation. On the other hand, the absorption in the range of 480 nm to 550 nm that originates from the perinaphthothioindigo site of the cis porphyrin compound (2') increased.

Figure 10:
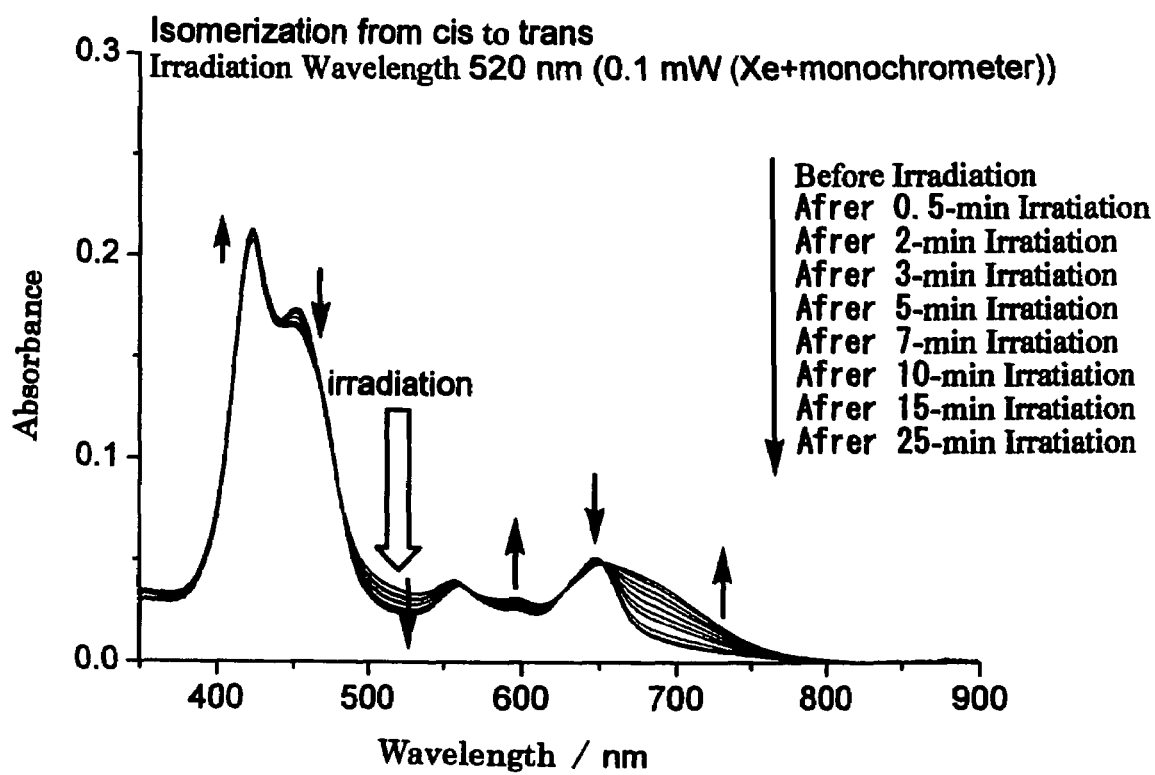
FIG. 10 is a graph showing the change in visible/ultraviolet absorption spectrum that is caused when the compound (2') of the example undergoes a photoisomerization reaction from a cis form to a trans form (in the THF solution).

The cis form (2') solution that has been excited was irradiated with light at room temperature (25° C.), and thereby the perinaphthothioindigo site was excited. The light irradiation was carried out at an average power of 0.1 mW, with a monochromator being connected to a 150 W Xe lamp with an irradiation wavelength of 520 nm. FIG. 10 shows the change with time in the visible/ultraviolet absorption spectrum that was caused when the cis body (2') solution was subjected to light irradiation (excitation). In FIG. 10, the vertical axis indicates the absorbance, while the horizontal axis indicates the wavelength. The black arrows shown in FIG. 10 each denote a decrease or an increase in absorption accompanying the light irradiation (excitation). The spectra are those obtained before the irradiation and 0.5, 2, 3, 5, 7, 10, 15, and 25 minutes after the start of irradiation. As shown in FIG. 10, the absorption in the range of 650 nm to 750 nm that originates from the perinaphthothioindigo site of the trans form (2) increased with light irradiation. On the other hand, the absorption in the range of 480 nm to 550 nm that originates from the perinaphthothioindigo site of the cis form (2) decreased. The change in spectrum almost stopped after 25 minutes of irradiation.

As described above, the trans porphyrin compound (2) was isomerized and thereby the cis porphyrin compound (2') was produced. At the same time, the photochromism of the trans form (2) and the cis form (2') also was confirmed.

Example 4

Three-dimensional Optical Recording Material

With respect to the porphyrin compounds (2) and (3) produced in Example 1, their performance as three-dimensional optical recording materials were evaluated.
<Fluorescence Spectrum Measurement>

As described above, the fluorescence spectrum was measured using a fluorescence spectrometer F-4500 (trade name) manufactured by Hitachi, Ltd. A Xe lamp with which the fluorescence spectrometer was equipped standardly was used as the excitation light source.

Figure 4:
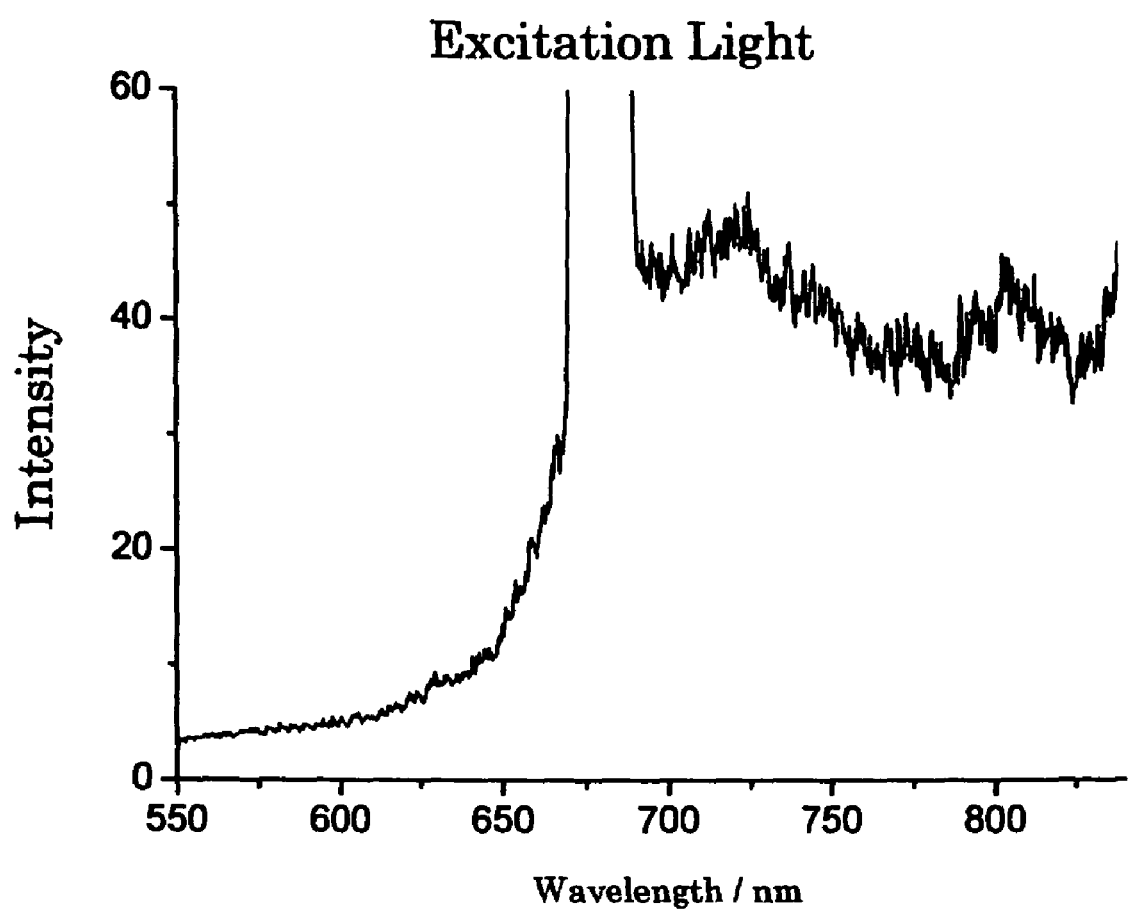
FIG. 4 is a graph showing a fluorescence spectrum of a trans compound (3) in the example (in the THF solution, with an excitation wavelength of 680 nm).

First, under the same conditions as those employed in Example 2, the trans porphyrin compound (3) solution was irradiated with excitation light and thereby the perinaphthothioindigo site was excited. Then the fluorescence spectrum of the solution that had been excited was measured. The concentration of the trans form (3) solution and the solvent used herein were the same as those used in Example 2. The irradiation wavelength was 680 nm. The fluorescence spectrum is shown in the graph in FIG. 4. In FIG. 4, the vertical axis indicates the fluorescence intensity, while the horizontal axis indicates the wavelength. The term "excitation light" indicated in FIG. 4 denotes that the excitation light used for the irradiation was observed at a wavelength of 680 nm. As shown in FIG. 4, fluorescence was observed in the range of 700 nm to 800 nm.

Figure 5:
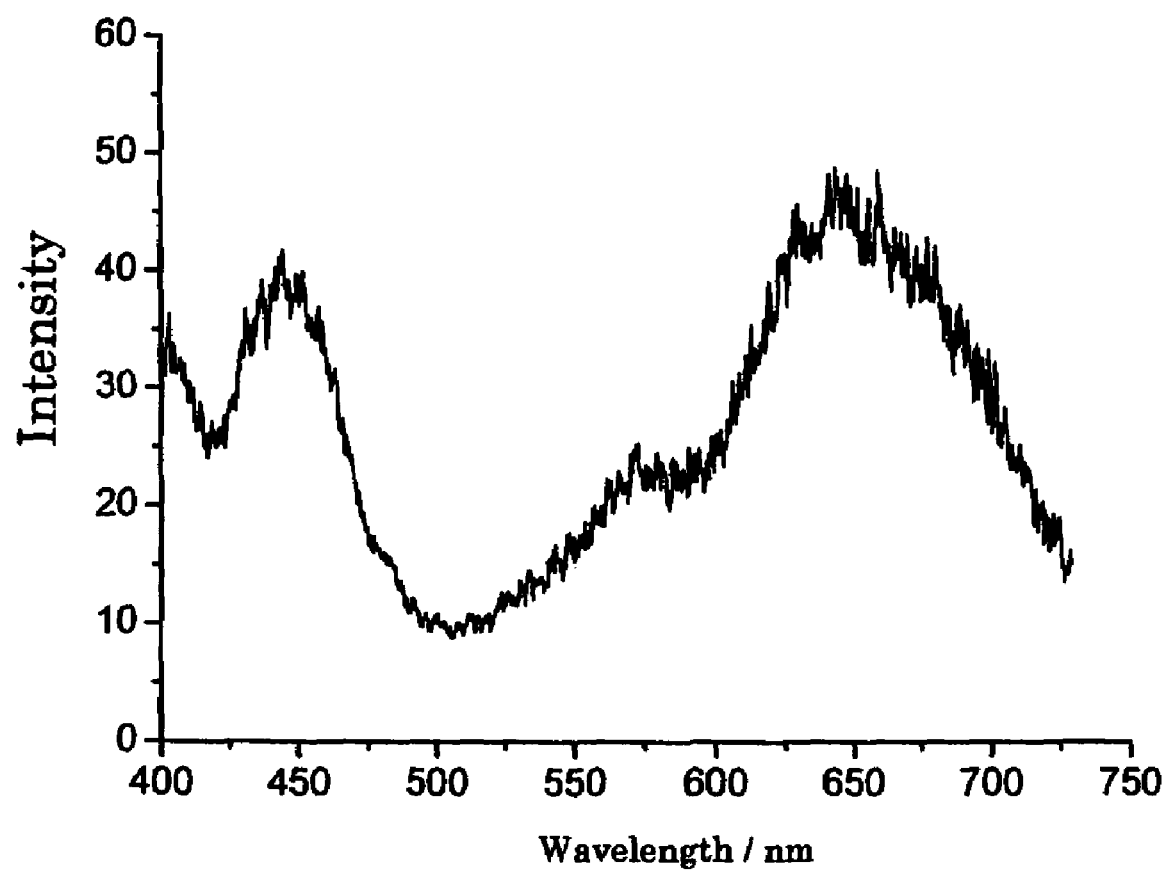
FIG. 5 is a graph showing an excitation spectrum of the trans compound (3) in the example (in the THF solution, with a fluorescence wavelength of 800 nm).

Furthermore, with the fluorescence observation wavelength being set at 800 nm, the change in fluorescence intensity at 800 nm that was caused when the irradiation wavelength was varied from 400 nm to 725 nm was measured (excitation spectrum). Then the fluorescence spectrum of the solution that had been excited was measured. The fluorescence spectrum is shown in the graph in FIG. 5. In FIG. 5, the vertical axis indicates the fluorescence intensity at 800 nm, while the horizontal axis indicates the excitation wavelength. As shown in FIG. 5, the excitation spectrum corresponding to the spectrum of absorption that originates from the perinaphthothioindigo site of the trans form (3) was obtained in the range of 600 nm to 750 nm. In addition, a spectrum originating from the Soret band of the porphyrin was obtained around 440 nm. This spectrum originating from the Soret band indicates that excitation energy concentrates at the perinaphthothioindigo site due to energy transfer even when the porphyrin site is excited with light. This result indicates that a trans form can be isomerized into a cis form by two-photon excitation of the Soret band region of porphyrin.

Figure 6:
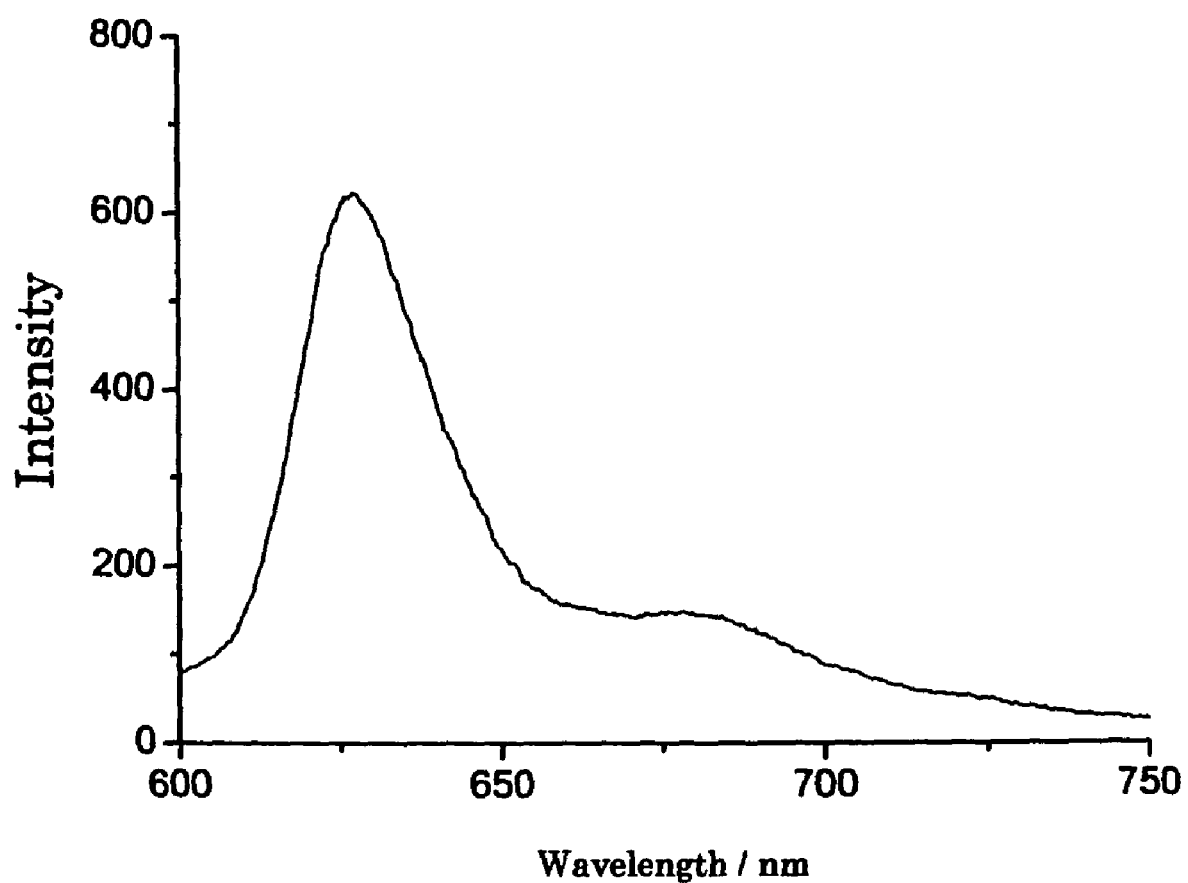
FIG. 6 is a graph showing a fluorescence spectrum of a cis compound (3') in the example (in the THF solution, with an excitation wavelength of 570 nm).

Any wavelength of 400 to 650 nm used for exciting the cis form (3') allowed it to emit light from the porphyrin site. Specifically, the fluorescence spectrum was measured using the same cis form (3') solution as that used in Example 2. FIG. 6 shows the fluorescence spectrum obtained when it was excited at an irradiation wavelength of 570 nm. In FIG. 6, the vertical axis indicates the fluorescence intensity, while the horizontal axis indicates the wavelength. As shown in FIG. 6, the emission intensity of the cis form (3') was higher than that of the trans form (3) by at least one order of magnitude.
<Isomerization (Photochromism) by Two-photon Absorption>

As described above, in the porphyrin compound (3), the absorption band of the one-photon absorption in the Soret band of porphyrin is around 440 nm. Accordingly, the wavelength at which the two-photon absorption occurs is approximately twice the wavelength of 440 nm. Hence, as described below, isomerization (photochromism) of the porphyrin compound (3) was carried out by two-photon absorption and thereby the performance thereof as a three-dimensional recording material was evaluated.

Figure 7:
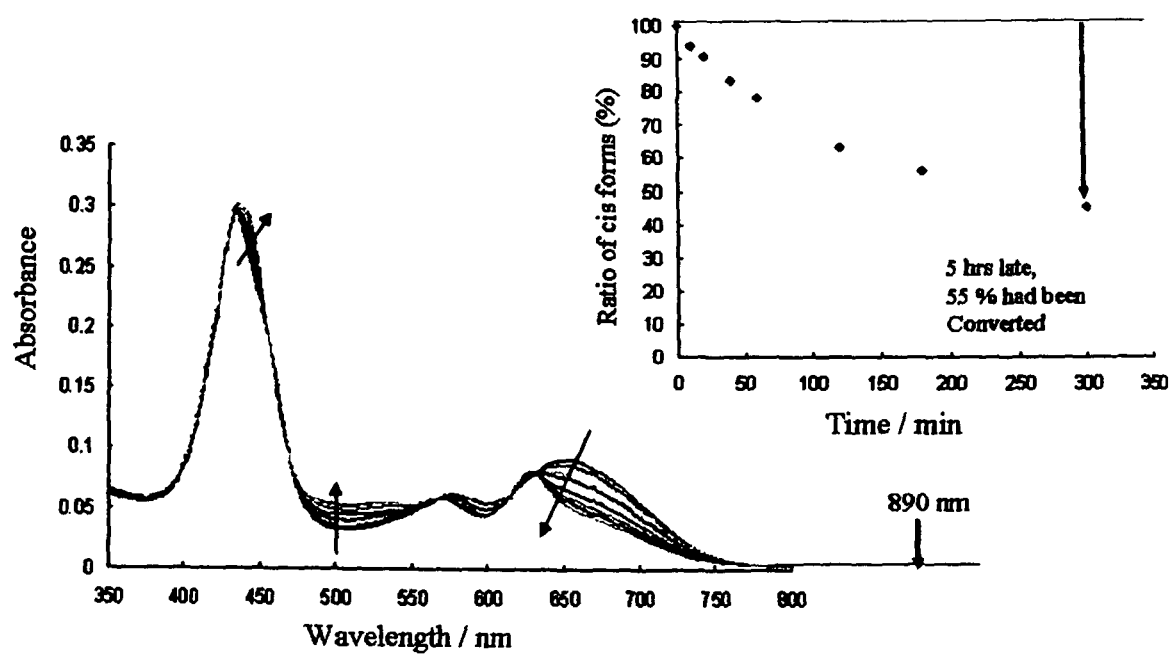
FIG. 7 is a graph showing a photoisomerization reaction from a trans form to a cis form by two-photon absorption of the trans compound (3) in the example (in the THF solution, with an excitation wavelength of 890 nm).

The conversion from a trans form (3) to a cis form (3') was carried out as follows. That is, first, the trans porphyrin compound (3) synthesized in Example 1 was dissolved in THF and thereby a 2.4 µM solution was prepared. This solution was subjected to two-photon excitation by laser beam irradiation at room temperature (25° C.) and thereby the change with time in the visible/ultraviolet absorption spectrum was measured. The irradiation wavelength was 890 nm. The laser beam used herein was a titanium:sapphire laser with a pulse width of 200 fs. The peak intensity was 0.53 GW/cm2. The change with time in the visible/ultraviolet absorption spectrum is shown in the graph in FIG. 7. In FIG. 7, the vertical axis indicates the absorbance, while the horizontal axis indicates the wavelength. The spectra are those obtained before the irradiation as well as 10, 20, 40, 60, 120, 180, and 300 minutes after the start of irradiation. In FIG. 7, the black arrows (→) attached to the respective absorption bands each denote an increase or a decrease in absorption accompanying the laser beam irradiation in the respective absorption bands. As shown in FIG. 7, the absorption in the range of 650 nm to 750 nm that originates from the perinaphthothioindigo site of the trans form (3) decreased with light irradiation. At the same time, the absorption in the range of 480 nm to 550 nm that originates from the perinaphthothioindigo site of the cis form (3') increased. The ratio of the cis form (3') that was calculated from the spectra shown in FIG. 7 is indicated in the graph of an inset shown in FIG. 7 (at the upper right-hand side of FIG. 7). In the inset, the vertical axis denotes the ratio (%) of the cis form (3'), while the horizontal axis indicates the irradiation time (min). As shown in the inset, 55% of the trans forms (3) that were present before the irradiation were converted to cis forms (3') after the irradiation for 300 minutes (five hours).

Figure 8:
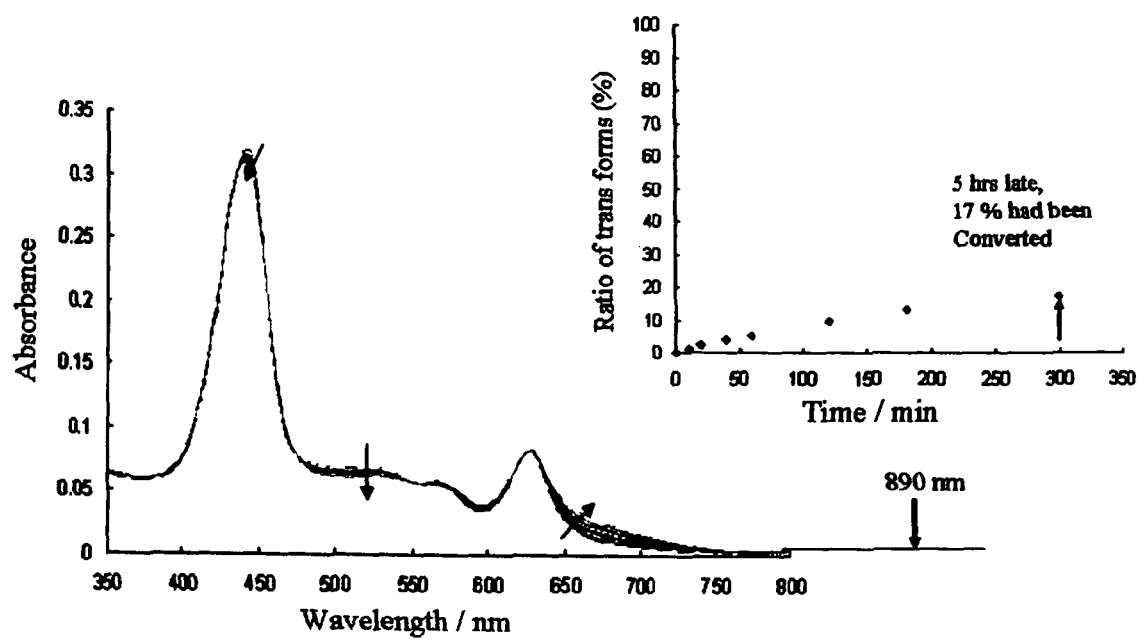
FIG. 8 is a graph showing a photoisomerization reaction from a cis form to a trans form by two-photon absorption of the cis compound (3') in the example (in the THF solution, with an excitation wavelength of 890 nm).

The conversion from the cis form (3') to the trans form (3) was carried out as follows. That is, first, under the same conditions as those employed in Example 2, a solution of the trans porphyrin compound (3) was irradiated with a laser beam whose wavelength was 680 nm and thereby the trans form (3) in the solution was converted to the cis form (3') completely. Then, the cis form (3') solution was irradiated with a laser beam at room temperature (25° C.) and thereby the cis form (3') was subjected to two-photon excitation. The change with time in the visible/ultraviolet absorption spectrum was measured. The irradiation wavelength was 890 nm. The laser beam used herein was a titanium:sapphire laser with a pulse width of 200 fs. The peak intensity was 0.53 GW/cm2. The change with time in the visible/ultraviolet absorption spectrum is shown in the graph in FIG. 8. In FIG. 8, the vertical axis indicates the absorbance, while the horizontal axis indicates the wavelength. The spectra are those obtained before the irradiation as well as 10, 20, 40, 60, 120, 180, and 300 minutes after the start of irradiation. In FIG. 8, the black arrows (→) attached to the respective absorption bands each denote an increase or a decrease in absorption accompanying the laser beam irradiation in the respective absorption bands. As shown in FIG. 8, the absorption in the range of 650 nm to 750 nm that originates from the perinaphthothioindigo site of the trans form (3) increased with light irradiation. At the same time, the absorption in the range of 480 nm to 550 nm that originates from the perinaphthothioindigo site of the cis form (3') decreased. The ratio of the trans form (3) that was calculated from the spectra shown in FIG. 8 is indicated in the graph of an inset shown in FIG. 8 (at the upper right-hand side of FIG. 8). In the inset, the vertical axis denotes the ratio (%) of the trans form (3), while the horizontal axis indicates the irradiation time (min). As shown in the inset, 17% of the cis forms (3') that were present before the irradiation were converted to trans forms (3) after the irradiation for 300 minutes (five hours).

As describe above, the irradiation with a laser beam whose wavelength was 890 nm caused photochromism phenomena, i.e. isomerization from a trans form (3) to a cis form (3') and isomerization from a cis form (3') to a trans form (3). That is, the photochromism caused by the two-photon absorption made it possible to confirm the usefulness of the porphyrin compound (3) as a three-dimensional optical recording material.

Similarly, with respect to the porphyrin compound (2), the photochromism phenomena, i.e. isomerization from a trans form (2) to a cis form (2') and isomerization from a cis form (2') to a trans form (2) were confirmed by the same method as described above. That is, the photochromism caused by the two-photon absorption made it possible to confirm the usefulness of the porphyrin compound (2) as a three-dimensional optical recording material.

<Measurement of Two-photon Absorption Cross Section>

The two-photon absorption cross sections of the compounds (2) and (3) were measured as follows. In the following, measurement carried out by the open Z-scan and analysis of the measurement result were carried out by the method described in a reference, K. Ogawa, A. Ohashi, Y. Kobuke, K. Kamada, and K. Ohta, J. Phys. Chem. B, 109, 22003-22012 (2005).

Figure 11:
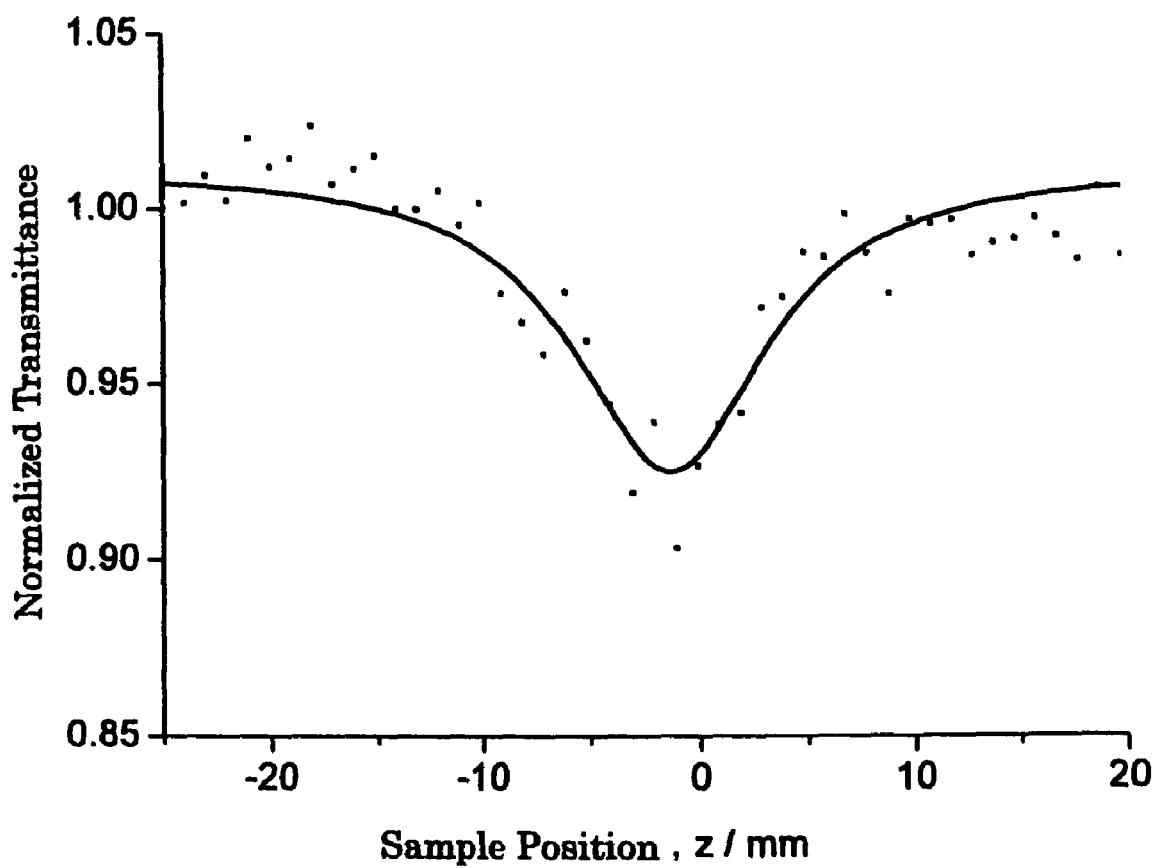
FIG. 11 is a graph obtained by subjecting the trans compound (3) to Z-scan in the example (THF solution, 5 ns pulse, 10 Hz, and 23 mW).
Figure 12:
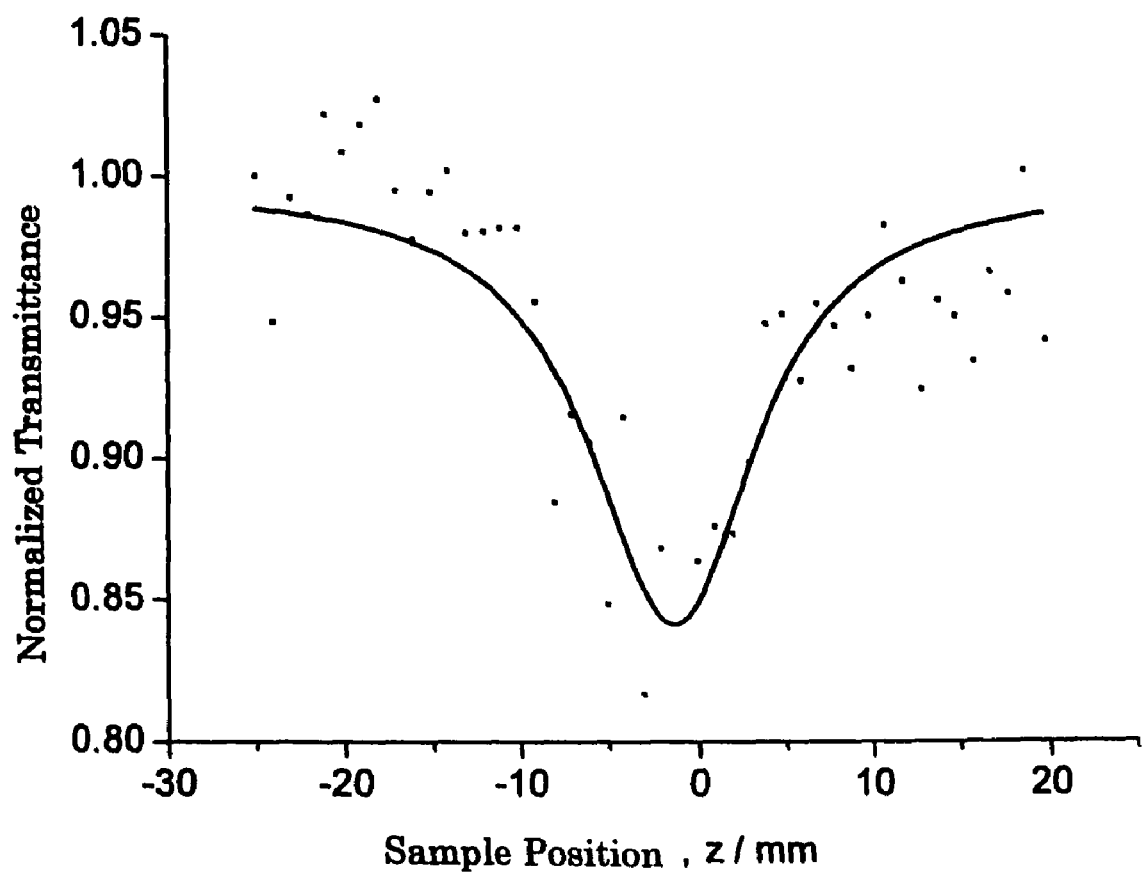
FIG. 12 is a graph obtained by subjecting the trans compound (2) to Z-scan in the example (THF solution, 5 ns pulse, 10 Hz, and 25 mW).

A THF solution ($2.4 \times 10^{-4}$ mol/L) of each of the compounds (2) and (3) was prepared. Then each solution was subjected to the measurement of two-photon absorption cross section at room temperature (25° C.). The measurement was carried out by the open Z-scan using a YAG:Nd laser with a pulse width of five nanoseconds. The wavelength of the laser beam was set at 890 nm using an optical parametric oscillator (OPO). The measurement was carried out by scanning the region 45 mm before and after the focal point of incident beam, using 2-mm cells. The laser beam output power was 25 mW with respect to the compound (2) solution while being 23 mW with respect to the compound (3) solution. The pulse repetition frequency was set at 10 Hz with respect to both the solutions. FIG. 11 shows the result of the open Z-scan measurement of the trans porphyrin compound (3). FIG. 12 shows the result of the open Z-scan measurement of the trans porphyrin compound (2). In FIGS. 11 and 12, the horizontal axis indicates the sample position, while the vertical axis indicates the normalized transmittance. The transmittance T is defined as $T=I_f/I_i$. In this formula, $I_f$ denotes the intensity of a laser beam that has passed through a sample, while $I_i$ denotes the intensity of a laser beam that has not passed through a sample yet. The normalization of transmittance (normalized transmittance) was carried out in the analysis described below. The results shown in FIGS. 11 and 12 were analyzed according to the method described in the aforementioned reference. Specifically, curve fitting was performed using the following formula (1).

$$T(\zeta) = \frac{(1-R)^2 e^{(-a^{(1)}L)}}{\sqrt{\pi}\, q(\zeta)} \int_{-\infty}^{\infty} \ln\!\left[1 + q(\zeta)e^{(-x^2)}\right] dx \qquad (1)$$

$$q(\zeta) = \frac{q_0}{1+\zeta^2} \qquad (2)$$

$$q_0 = \alpha^{(2)}(1-R)I_0 L_{\text{eff}} \qquad (3)$$

$$\sigma^{(2)} = \hbar\omega\alpha^{(2)}/N \qquad (4)$$

In the above-mentioned formulae, $\zeta=(z-z_0)/Z_R$, and $z_0$ and $z_R$ denote a focal position and a Rayleigh range, respectively. $T(\zeta)$ is normalized to 1 at a position that is far apart from the focal point (i.e. $T(\zeta \to \pm\infty)=1$). R indicates Fresnel reflectance, L denotes cell length, and a(2) indicates a two-photon absorption coefficient. $L_{\text{eff}}$ denotes effective length of a cell. However, since one-photon absorption does not occur, $L=L_{\text{eff}}$. $I_0$ indicates the peak intensity at the focal point, N denotes molecular density, and hω indicates photon energy of an incident beam. Finally, the two-photon absorption cross section $\sigma^{(2)}$ was calculated from the formula (4). As a result of the analysis described above, the two-photon absorption cross section of the trans porphyrin compound (2) was 22000 GM. On the other hand, the two-photon absorption cross section of the trans porphyrin compound (3) was 15000 GM. Thus both the compounds showed very large values of two-photon absorption cross section. This proved that the compounds (2) and (3) each were able to provide a very large recording capacity as a three-dimensional recording material.

In this example, the compounds (2) and (3) were produced. However, as described above, any person skilled in the art of the present invention can produce compounds of the present invention having structures other than those of the compounds (2) and (3), i.e. porphyrin compounds represented by the following formula (1) and containing one or a plurality of porphyrin rings and one or a plurality of perinaphthothioindigo rings, tautomers or stereoisomers thereof, or salts thereof, based on the description of the present specification (in consideration of common knowledge in the art in some cases) without carrying out an excessive amount of trial and error as well as complicated and sophisticated experiments. Furthermore, in this example, the usefulness of the porphyrin compounds (2) and (3) as three-dimensional optical recording materials was confirmed by photochromism caused by two-photon absorption. However, it is obvious for persons skilled in the art that the similar effects also can be obtained with respect to compounds of the present invention having other structures. Specifically, this can be described as follows. As described above, in the compounds of the present invention, a porphyrin ring and a perinaphthothioindigo ring are linked to each other with a straight-chain atomic group. In addition, pi-electron conjugation between the porphyrin ring and the perinaphthothioindigo ring can be achieved. Since the compounds of the present invention each have the aforementioned porphyrin ring, they can cause two-photon absorption as in the examples. The aforementioned perinaphthothioindigo ring can receive the two-photon absorption energy through the pi-electron conjugation. Accordingly, the perinaphthothioindigo ring is isomerized and thereby the photochromism occurs. That is, the photochromism can be caused by the two-photon absorption as long as the compounds of the present invention each have the structure of the formula (1). Furthermore, as described above, when photochromism is caused by two-photon absorption, the compounds can be used for three-dimensional recording. In addition, the use of the compounds according to the present invention is not limited to three-dimensional optical recording materials and three-dimensional optical recording media. They can be used for other applications.

INDUSTRIAL APPLICABILITY

As described above, since the compounds of the present invention have high two-photon absorption efficiency and can undergo photochromism effectively by optical absorption, they are suitable to be used for three-dimensional optical recording materials, etc. The three-dimensional optical recording materials of the present invention each contain a compound of the present invention and thereby allow three-dimensional recording to be carried out. In addition, the three-dimensional optical recording media of the present invention each have the aforementioned structure and therefore allow large-volume recording to be carried out. For instance, the present invention can provide media for rewritable three-dimensional optical memories. Moreover, in case the compounds of the present invention have a two-photon absorption cross section as large as 10000 GM or more as described above, for instance, it is possible to record information with a high density, specifically 1 terabit per 1 $cm^3$ (equivalent to 100,000 Floppy Disks®). Since the three-dimensional optical recording media of the present invention have such a large recording capacity, they can be expected to become the next-generation memory media. Moreover, the use of the compounds according to the present invention is not limited to the three-dimensional optical recording materials and three-dimensional optical recording media. They can be used for any applications.

What is claimed is:
1. A compound, a tautomer or a stereoisomer, or a salt thereof represented by the following formula (1),

wherein in the formula (1), $P^1$ denotes an atomic group represented by the following formula ($a^1$),

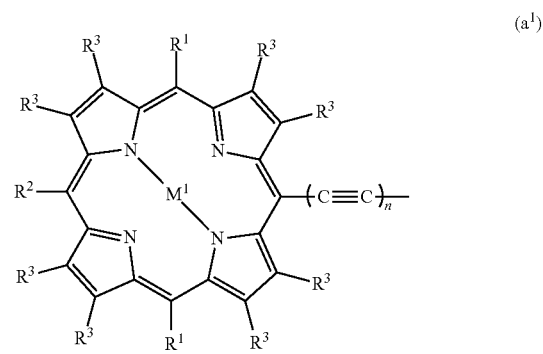

[Y] denotes an atomic group represented by the following formula ($c^2$),

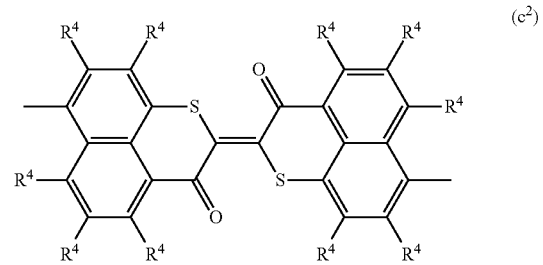

$P^2$ denotes a hydrogen atom or a halogen,
in the formula ($a^1$),
$R^1$s each indicate a hydrogen atom, a substituted or non-substituted alkyl group, or a substituted or non-substituted aryl group, the substituted or non-substituted alkyl group can be of a straight-chain or a branched-chain or can be cyclic (a substituted or non-substituted cycloalkyl group), the substituted alkyl group can contain one or a plurality of substituents, in the case of the plurality of substituents, they can be identical to or different from each other, the substituted or non-substituted aryl group can be of a monocycle or a condensed ring, the substituted aryl group can contain one or a plurality of substituents, in the case of the plurality of substituents, they can be identical to or different from each other, and the respective $R^1$s can be identical to or different from each other, and $R^3$s each indicate a hydrogen atom, a substituted or non-substituted alkyl group, or a substituted or non-substituted aryl group, the substituted or non-substituted alkyl group can be of a straight-chain or a branched-chain or can be cyclic (a substituted or non-substituted cycloalkyl group), the substituted alkyl group can contain one or a plurality of substituents, in the case of the plurality of substituents, they can be identical to or different from each other, the substituted or non-substituted aryl group can be of a monocycle or a condensed ring, the substituted aryl group can contain one or a plurality of substituents, in the case of the plurality of substituents, they can be identical to or different from each other, and the respective $R^3$s can be identical to or different from each other, in the formula ($a^1$), n denotes an integer of 1 to 3, in the formula ($a^1$), $R^2$ indicates a hydrogen atom, a substituted or non-substituted alkyl group, a substituted or non-substituted aryl group, a five- or six-membered nitrogen-containing coordinating heteroaromatic ring, or a halogen, the substituted or non-substituted alkyl group can be of a straight-chain or a branched-chain or can be cyclic (a substituted or non-substituted cycloalkyl group), the substituted alkyl group can contain one or a plurality of substituents, in the case of the plurality of substituents, they can be identical to or different from each other, the substituted or non-substituted aryl group can be of a monocycle or a condensed ring, the substituted aryl group can contain one or a plurality of substituents, in the case of the plurality of substituents, they can be identical to or different from each other, and $M^1$ indicates metal, metal halide, metal oxide, metal hydroxide, Si, Ge, or P, or two hydrogen atoms, and in the formulae ($c^2$), $R^4$s each denote a hydrogen atom or a halogen, and the respective $R^4$s can be identical to or different from each other.

2. The compound, the tautomer or stereoisomer thereof, or the salt thereof according to claim 1, wherein in the formula (1), in the formula ($a^1$), in $R^1$, the substituted alkyl group is at least one selected from the group consisting of an alkoxycarbonylalkyl group, an alkoxyalkyl group, an alkenoxyalkyl group, an alkenoxycarbonylalkyl group, and a carboxyalkyl group, the substituted aryl group is at least one selected from the group consisting of an alkylaryl group, alkoxyaryl group, alkoxycarbonylaryl group, alkenoxyaryl group, a carboxyaryl group, and alkenoxycarbonylaryl group, and the respective $R^1$s can be identical to or different from each other, in the formula ($a^1$), in $R^2$, the substituted alkyl group is at least one selected from the group consisting of an alkoxycarbonylalkyl group, an alkoxyalkyl group, an alkenoxyalkyl group, an alkenoxycarbonylalkyl group, and a carboxyalkyl group, the substituted aryl group is at least one selected from the group consisting of an alkylaryl group, alkoxyaryl group, alkoxycarbonylaryl group, alkenoxyaryl group, a carboxyaryl group, and alkenoxycarbonylaryl group, the five- or six-membered nitrogen-containing coordinating heteroaromatic ring is at least one selected from the group consisting of imidazole, N-methylimidazole, pyridine, pyrazole, and pyrimidine, and in the formula ($c^2$), $R^4$s each denote a hydrogen atom or a halogen, and the respective $R^4$s can be identical to or different from each other.

3. The compound, the tautomer or stereoisomer thereof, or the salt thereof according to claim 1, wherein n is 1.

4. The compound, the tautomer or stereoisomer thereof, or the salt thereof according to claim 1, wherein in the formula (1), in the formula ($a^1$), $M^1$ denotes an of zinc, iron, cobalt, ruthenium, or gallium, or two hydrogen atoms.

5. The compound, the tautomer or stereoisomer thereof, or the salt thereof according to claim 1, wherein in the formula (1), in the formula ($a^1$), in $R^1$, the substituted or non-substituted alkyl group has a total number of carbon atoms of 1 to 24, while the substituted or non-substituted aryl group has a total number of carbon atoms of 6 to 24, and in the formula ($a^1$), in $R^2$, the substituted or non-substituted alkyl group has a total number of carbon atoms of 1 to 24, while the substituted or non-substituted aryl group has a total number of carbon atoms of 6 to 24.

6. The compound, the tautomer or stereoisomer thereof, or the salt thereof according to claim 1, wherein the compound represented by the formula (1) is a compound that is represented by the following formula (xi) in which

[Y] is represented by the formula ($c^2$), $P^1$ is represented by the formula ($a^1$), $P^2$ is a hydrogen atom, in the formula ($a^1$) and $R^3$s are hydrogen atoms, n is 1, and in the formula ($c^2$), $R^4$s are all hydrogen atoms,

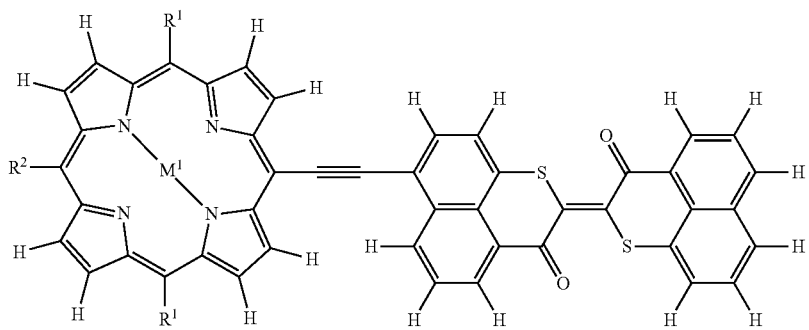

(xi)

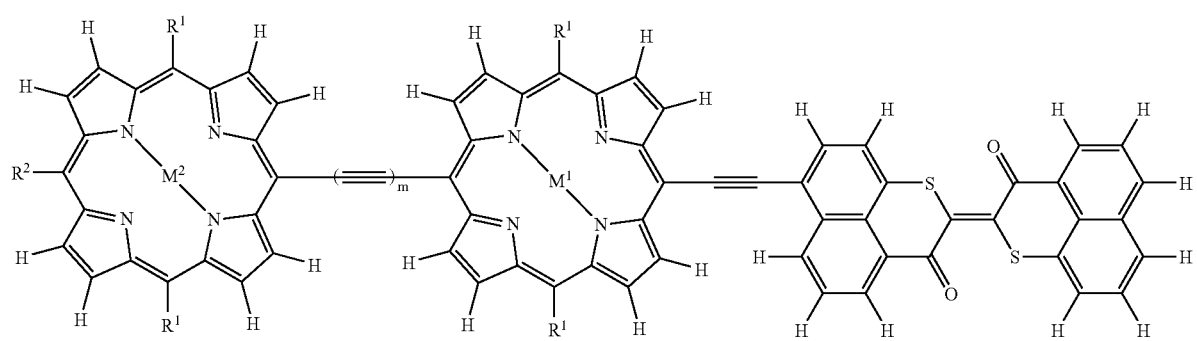

(xii)

in the formula (xi),
$M^1$ denotes a metal or two hydrogen atoms.

7. The compound, the tautomer or stereoisomer thereof, or the salt thereof according to claim 1, wherein in the formula (1),
the compound represented by the formula (1) is a compound that is represented by the following formula (xxi) in which
[Y] is represented by the formula ($c^2$),
$P^1$ is represented by the formula ($a^1$),
$P^2$ is a hydrogen atom,
in the formula ($a^1$)
n is 1,
$R^2$ is a hydrogen atom, and
$R^3$s are all hydrogen atoms, and
in the formula ($c^2$),
$R^4$s are all hydrogen atoms, in the formula (xxi),
$R^1$s each are at least one selected from the group consisting of a hydrogen atom, a methyl group, an ethyl group, an n-propyl group, an isopropyl group, an n-butyl group, a sec-butyl group, an isobutyl group, a tert-butyl group, a pentyl group, a hexyl group, a phenyl group, a 4-methoxycarbonylphenyl group, a 3,5-bis(methoxycarbonyl)phenyl group, a 4-ethoxycarbonylphenyl group, and a 3,5-bis(ethoxycarbonyl)phenyl group, and the respective $R^1$s can be identical to or different from each other, and
$M^1$ denotes Zn(II), Ga(III), Fe(II), Fe(III), Co(II), Co(III), Ru(II), Ru(III), or two hydrogen atoms.

8. The compound, the tautomer or stereoisomer thereof, or the salt thereof according to claim 1, wherein the compound represented by the formula (1) is a compound represented by the following formula (3):

(xxi)

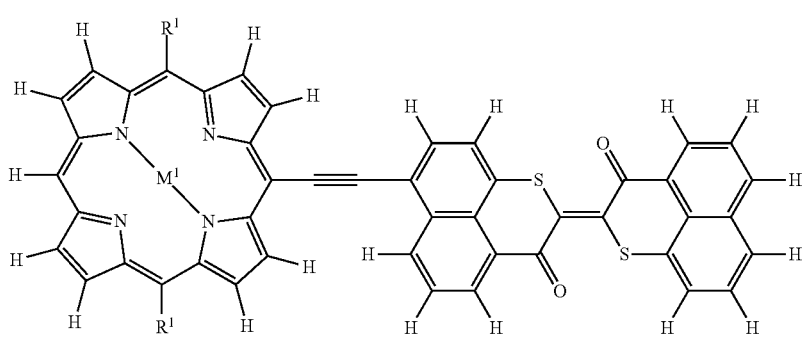

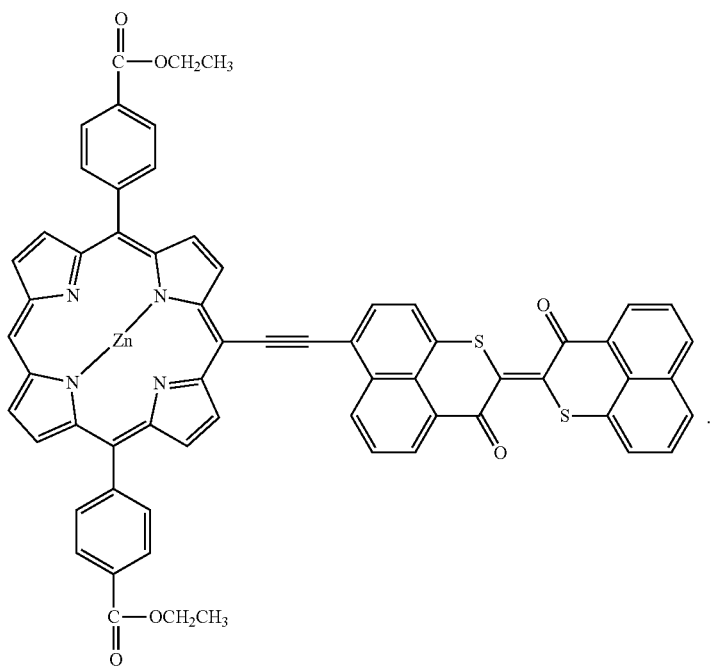
(3)